US011545234B2

(12) United States Patent
Patel et al.

(10) Patent No.: US 11,545,234 B2
(45) Date of Patent: Jan. 3, 2023

(54) DECODING APPROACHES FOR PROTEIN IDENTIFICATION

(71) Applicant: Nautilus Biotechnology, Inc., Seattle, WA (US)

(72) Inventors: Sujal M. Patel, Seattle, WA (US); Parag Mallick, San Mateo, CA (US); Jarrett D. Egertson, San Carlos, CA (US)

(73) Assignee: Nautilus Biotechnology, Inc., Seattle, WA (US)

( * ) Notice: Subject to any disclaimer, the term of this patent is extended or adjusted under 35 U.S.C. 154(b) by 0 days.

(21) Appl. No.: 17/221,431

(22) Filed: Apr. 2, 2021

(65) Prior Publication Data

US 2021/0304839 A1    Sep. 30, 2021

Related U.S. Application Data

(63) Continuation of application No. 16/534,174, filed on Aug. 7, 2019, which is a continuation of application
(Continued)

(51) Int. Cl.
*G16B 5/20* (2019.01)
*G01N 27/26* (2006.01)
(Continued)

(52) U.S. Cl.
CPC .............. *G16B 5/20* (2019.02); *G01N 27/26* (2013.01); *G01N 27/60* (2013.01); *G01N 27/72* (2013.01)

(58) Field of Classification Search
CPC .......... G16B 5/20; G01N 27/26; G01N 27/60; G01N 27/72
See application file for complete search history.

(56) References Cited

U.S. PATENT DOCUMENTS 5,445,934 A    8/1995   Fodor et al.
6,762,056 B1   7/2004   Peeters
(Continued)

FOREIGN PATENT DOCUMENTS

EP    1047107 A2    10/2000
EP    1047107 B1    10/2006
(Continued)

OTHER PUBLICATIONS

Palma, P. Nuno, et al. "BiGGER: a new (soft) docking algorithm for predicting protein interactions." Proteins: Structure, Function, and Bioinformatics 39.4 (2000): 372-384. (Year: 2000).*
(Continued)

*Primary Examiner* — Robert J Eom
(74) *Attorney, Agent, or Firm* — Knobbe Martens Olson & Bear, LLP

(57) ABSTRACT

Methods and systems are provided for accurate and efficient identification and quantification of proteins. In an aspect, disclosed herein is a method for identifying a protein in a sample of unknown proteins, comprising receiving information of a plurality of empirical measurements performed on the unknown proteins; comparing the information of empirical measurements against a database comprising a plurality of protein sequences, each protein sequence corresponding to a candidate protein among a plurality of candidate proteins; and for each of one or more of the plurality of candidate proteins, generating a probability that the candidate protein generates the information of empirical measurements, a probability that the plurality of empirical measurements is not observed given that the candidate protein is present in the sample, or a probability that the candidate protein is present in the sample; based on the comparison of the information of empirical measurements against the database.

26 Claims, 24 Drawing Sheets

Related U.S. Application Data

No. PCT/US2018/067985, filed on Dec. 28, 2018, which is a continuation-in-part of application No. PCT/US2018/056807, filed on Oct. 20, 2018.

(60) Provisional application No. 62/611,979, filed on Dec. 29, 2017.

(51) Int. Cl.
    *G01N 27/60*      (2006.01)
    *G01N 27/72*      (2006.01)

(56) References Cited

U.S. PATENT DOCUMENTS

| | | | |
|---|---|---|---|
| 7,252,954 B2 | 8/2007 | Wang et al. | |
| 7,955,837 B2 | 6/2011 | Pawlak | |
| 9,528,984 B2 | 12/2016 | Mitra | |
| 9,880,175 B2 | 1/2018 | Mitra | |
| 10,175,248 B2 | 1/2019 | Mitra | |
| 10,571,473 B2 | 2/2020 | Mitra | |
| 10,829,816 B2 | 11/2020 | Staker et al. | |
| 10,921,317 B2 | 2/2021 | Mallick | |
| 2003/0054408 A1 | 3/2003 | Ravi et al. | |
| 2004/0166106 A1 | 8/2004 | Wang et al. | |
| 2005/0074809 A1 | 4/2005 | Brusic | |
| 2005/0131647 A1 | 6/2005 | Maroto | |
| 2011/0177107 A1 | 7/2011 | Howard | |
| 2013/0053541 A1 | 2/2013 | Shankar et al. | |
| 2013/0178372 A1 | 7/2013 | Geiss et al. | |
| 2015/0330974 A1 | 11/2015 | Staker et al. | |
| 2018/0101643 A1* | 4/2018 | Spahn | G16C 20/60 |
| 2020/0082914 A1 | 3/2020 | Patel et al. | |
| 2020/0090785 A1 | 3/2020 | Patel et al. | |
| 2020/0232994 A1 | 7/2020 | Mitra | |
| 2020/0286584 A9 | 9/2020 | Patel et al. | |
| 2020/0318101 A1 | 10/2020 | Mallick et al. | |
| 2021/0358562 A1 | 11/2021 | Patel et al. | |
| 2021/0358563 A1 | 11/2021 | Patel et al. | |

FOREIGN PATENT DOCUMENTS

| | | |
|---|---|---|
| WO | WO-0073787 A1 | 12/2000 |
| WO | WO2000073787 A1 | 12/2000 |
| WO | WO-02086081 A2 | 10/2002 |
| WO | WO2002086081 A2 | 10/2002 |
| WO | WO-03083441 A2 | 10/2003 |
| WO | WO-2014078855 A1 | 5/2014 |
| WO | WO-2018102759 A1 | 6/2018 |
| WO | WO-2019083856 A1 | 5/2019 |
| WO | WO-2019133892 A1 | 7/2019 |
| WO | WO-2021003470 | 1/2021 |

OTHER PUBLICATIONS

Lu, Long, Hui Lu, and Jeffrey Skolnick. "Multiprospector: an algorithm for the prediction of protein-protein interactions by multimeric threading." Proteins: Structure, Function, and Bioinformatics 49.3 (2002): 350-364. (Year: 2002).*

Mallick, Parag, et al. "Computational prediction of proteotypic peptides for quantitative proteomics." Nature biotechnology 25.1 (2007): 125-131. (Year: 2007).*

Zingaretti, Chiara, et al. "Identification of new autoantigens by protein array indicates a role for IL4 neutralization in autoimmune hepatitis." Molecular & Cellular Proteomics 11.12 (2012): 1885-1897. (Year: 2012).*

Mendoza, Vanessa Leah, and Richard W. Vachet. "Probing protein structure by amino acid-specific covalent labeling and mass spectrometry." Mass spectrometry reviews 28.5 (2009): 785-815. (Year: 2009).*

Audain, et al. Accurate estimation of isoelectric point of protein and peptide based on amino acid sequences. Bioinformatics. Mar. 15, 2016; 32(6): 821-827.

Co-pending U.S. Appl. No. 16/760,032, inventors Chee; Mark S. et al., filed Apr. 28, 2020.

Co-pending U.S. Appl. No. 17/221,405, inventors Patel; Sujal M. et al., filed Apr. 2, 2021.

Fodor, et al. Light-Directed, Spatially Addressable Parallel Chemical Synthesis. Science , vol. 251, 767-773, 1991.

Frato, et al. A DNA-Assisted Binding Assay for Weak Protein-Protein Interactions. J Mol Biol. Dec. 18, 2009; 394(5): 805-814.

Hosseinzadeh, et al. Comprehensive computational design of ordered peptide macrocycles. Science. Dec. 15, 2017; 358(6369): 1461-1466.

Kyte et al. A simple method for displaying the hydropathic character of a protein. J. Mol. Biol. 157:105-132 (1982).

PCT/US18/56807 International Search Report dated Feb. 27, 2019.
PCT/US18/67985 International Search Report dated Mar. 5, 2019.
PCT/US20/40829 International Search Report dated Nov. 9, 2020.

Tabb, D. An algorithm for isoelectric point estimation. Created Jul. 10, 2001; Updated Jun. 28, 2003. Available at http://fields.scripps.edu/DTASelect/20010710-pl-Algorithm.pdf.

U.S. Appl. No. 16/534,174 Office Action dated Dec. 18, 2020.
U.S. Appl. No. 16/534,174 Office Action dated Jun. 8, 2020.
U.S. Appl. No. 17/221,405 Office Action dated Jun. 16, 2021.
U.S. Appl. No. 17/221,431 Office Action dated Jun. 16, 2021.

Yates, et al. SuSPect: enhanced prediction of single amino acid variant (SAV) phenotype using network features. Journal of molecular biology 426.14 (2014): 2692-2701.

Buus, et al. High-resolution mapping of linear antibody epitopes using ultrahigh-density peptide microarrays. Molecular & Cellular Proteomics 11.12 (2012): 1790-1800.

EP18871210 Extended European Search Report dated Jul. 8, 2021.
EP18896481 Extended European Search Report dated Aug. 10, 2021.

Forsstrom, B. et al. Proteome-wide epitope mapping of antibodies using ultra-dense peptide arrays. Molecular & cellular proteomics: MCP vol. 13,6 (2014): 1585-97.

Frato, et al. A DNA-assisted binding assay for weak protein-protein interactions. Journal of molecular biology vol. 394,5 (2009): 805-14.

Huntley, et al. Information capacity of specific interactions. PNAS 113.21 (2016): 5841-5846.

Ohmura, et al. An immunoassay for small analytes with theoretical detection limits. Analytical chemistry 73.14(2001): 3392-3399.

U.S. Appl. No. 16/534,174 Office Action dated Sep. 13, 2021.
U.S. Appl. No. 16/534,257 Office Action dated Oct. 27, 2021.
U.S. Appl. No. 17/221,405 Final Office Action dated Oct. 12, 2021.
U.S. Appl. No. 17/387,665 Office Action dated Dec. 7, 2021.
U.S. Appl. No. 17/387,670 Office Action dated Dec. 7, 2021.

Sauer M. Journal of Cell Science 126, 3505-3513, 2013.
Kiuchi, et al. Nature Methods 12, 743-746, 2015.

Plückthun, Andreas, and Peter Pack. "New protein engineering approaches to multivalent and bispecific antibody fragments." Immunotechnology 3.2 (1997): 83-105.

\* cited by examiner

DECODING APPROACHES FOR PROTEIN IDENTIFICATION

CROSS-REFERENCE

This application is a continuation of U.S. patent application Ser. No. 16/534,174, filed Aug. 7, 2019, which is a continuation of International Application No. PCT/US2018/067985, filed Dec. 28, 2018, which claims the benefit of U.S. Provisional Patent Application No. 62/611,979, filed Dec. 29, 2017; International Application No. PCT/US2018/067985 is a continuation-in-part of International Application No. PCT/US2018/056807, filed Oct. 20, 2018, each of which is entirely incorporated by reference herein in its entirety.

BACKGROUND

Current techniques for protein identification typically rely upon either the binding and subsequent readout of highly specific and sensitive affinity reagents (such as antibodies) or upon peptide-read data (typically on the order of 12-30 amino acids long) from a mass spectrometer. Such techniques may be applied to unknown proteins in a sample to determine the presence, absence, or quantity of candidate proteins based on analysis of binding measurements of the highly specific and sensitive affinity reagents to the protein of interest.

SUMMARY

Recognized herein is a need for improved identification and quantification of proteins within a sample of unknown proteins. Methods and systems provided herein can significantly reduce or eliminate errors in identifying proteins in a sample and thereby improve the quantification of said proteins. Such methods and systems may achieve accurate and efficient identification of candidate proteins within a sample of unknown proteins. Such identification may be based on calculations using information such as binding measurements of affinity reagent probes configured to selectively bind to one or more candidate proteins, protein length, protein hydrophobicity, and isoelectric point. In some embodiments, a sample of unknown proteins may be exposed to individual affinity reagent probes, pooled affinity reagent probes, or a combination of individual affinity reagent probes and pooled affinity reagent probes. The identification may comprise estimation of a confidence level that each of one or more candidate proteins is present in the sample.

Methods and systems provided herein may comprise algorithms for identifying proteins based on a sequence of experiments performed on fully-intact proteins or protein fragments. Each experiment may be an empirical measurement performed on a protein and may provide information which may be useful for identifying the protein. Examples of experiments include measurement of the binding of an affinity reagent (e.g., antibody or aptamer), protein length, protein hydrophobicity, and isoelectric point. Information about experimental outcomes may be used to calculate probabilities or likelihoods of protein candidates and/or to infer protein identity by selecting the protein from a list of protein candidates that maximizes the likelihood of the observed experimental outcomes. Methods and systems provided herein may also comprise a collection of protein candidates, and algorithms to calculate the probability of experimental outcomes from each of these protein candidates.

In an aspect, the present disclosure provides a computer-implemented method for identifying a protein in a sample of unknown proteins, the method comprising: (a) receiving, by said computer, information of a plurality of empirical measurements performed on said unknown proteins in said sample; (b) comparing, by said computer, at least a portion of said information of said plurality of said empirical measurements against a database comprising a plurality of protein sequences, each protein sequence corresponding to a candidate protein among a plurality of candidate proteins; and (c) for each of one or more candidate proteins in said plurality of candidate proteins, generating, by said computer, one or more of: (i) a probability that said candidate protein generates said information of said plurality of empirical measurements, (ii) a probability that said plurality of empirical measurements is not observed given that said candidate protein is present in said sample, and (iii) a probability that said candidate protein is present in said sample; based on said comparison of said at least a portion of said information of said plurality of said empirical measurements against said database comprising said plurality of protein sequences.

In some embodiments, two or more of said plurality of empirical measurements are selected from the group consisting of: (i) binding measurements of each of one or more affinity reagent probes to said unknown proteins in said sample, each affinity reagent probe configured to selectively bind to one or more candidate proteins among said plurality of candidate proteins; (ii) length of one or more of said unknown proteins in said sample; (iii) hydrophobicity of one or more of said unknown proteins in said sample; and (iv) isoelectric point of one or more of said unknown proteins in said sample.

In some embodiments, generating said plurality of probabilities further comprises receiving additional information of binding measurements of each of a plurality of additional affinity reagent probes, each additional affinity reagent probe configured to selectively bind to one or more candidate proteins among said plurality of candidate proteins. In some embodiments, the method further comprises generating, for said each of one or more candidate proteins, a confidence level that said candidate protein matches one of said unknown proteins in said sample.

In some embodiments, said plurality of affinity reagent probes comprises no more than 50 affinity reagent probes. In some embodiments, said plurality of affinity reagent probes comprises no more than 100 affinity reagent probes. In some embodiments, said plurality of affinity reagent probes comprises no more than 200 affinity reagent probes. In some embodiments, said plurality of affinity reagent probes comprises no more than 300 affinity reagent probes. In some embodiments, said plurality of affinity reagent probes comprises no more than 500 affinity reagent probes. In some embodiments, said plurality of affinity reagent probes comprises more than 500 affinity reagent probes. In some embodiments, the method further comprises generating a paper or electronic report identifying said proteins in said sample.

In some embodiments, said sample comprises a biological sample. In some embodiments, said biological sample is obtained from a subject. In some embodiments, the method further comprises identifying a disease state in said subject based at least on said plurality of probabilities.

In some embodiments, (c) comprises, for each of one or more candidate proteins in said plurality of candidate proteins, generating, by said computer, (i) said probability that said candidate protein generates said information of said plurality of empirical measurements. In some embodiments, (c) comprises, for each of one or more candidate proteins in said plurality of candidate proteins, generating, by said computer, (ii) said probability that said plurality of empirical measurements is not observed given that said candidate protein is present in said sample. In some embodiments, (c) comprises, for each of one or more candidate proteins in said plurality of candidate proteins, generating, by said computer, (iii) said probability that said candidate protein is present in said sample. In some embodiments, said measurement outcome comprises binding of affinity reagent probes. In some embodiments, said measurement outcome comprises non-specific binding of affinity reagent probes. In some embodiments, said measurement outcome comprises binding of affinity reagent probes. In some embodiments, said measurement outcome comprises non-specific binding of affinity reagent probes. In some embodiments, said empirical measurements comprise binding of affinity reagent probes. In some embodiments, said empirical measurements comprise non-specific binding of affinity reagent probes.

In some embodiments, the method further comprises generating a sensitivity of protein identification with a pre-determined threshold. In some embodiments, said pre-determined threshold is less than 1% of being incorrect. In some embodiments, said protein in said sample is truncated or degraded. In some embodiments, said protein in said sample does not originate from a protein terminus.

In some embodiments, said empirical measurements comprise length of one or more of said unknown proteins in said sample. In some embodiments, said empirical measurements comprise hydrophobicity of one or more of said unknown proteins in said sample. In some embodiments, said empirical measurements comprise isoelectric point of one or more of said unknown proteins in said sample. In some embodiments, said empirical measurements comprise measurements performed on mixtures of antibodies. In some embodiments, said empirical measurements comprise measurements performed on samples obtained from a plurality of species. In some embodiments, said empirical measurements comprise measurements performed on samples in the presence of single amino acid variants (SAVs) caused by non-synonymous single-nucleotide polymorphisms (SNPs).

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
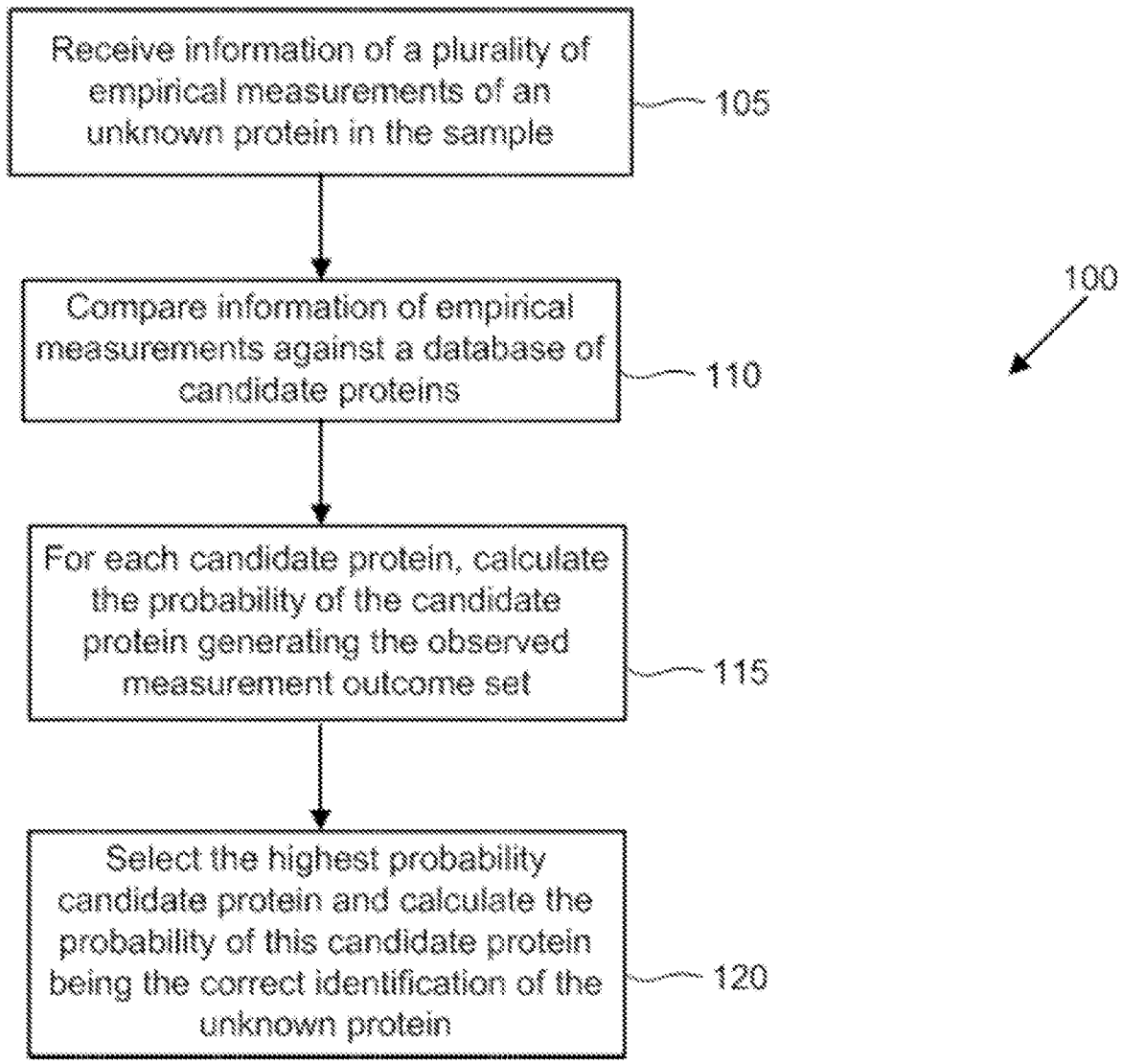
FIG. 1 illustrates an example flowchart of protein identification of unknown proteins in a biological sample, in accordance with disclosed embodiments.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "sample," as used herein, generally refers to a biological sample (e.g., a sample containing protein). The samples may be taken from tissue or cells or from the environment of tissue or cells. In some examples, the sample may comprise, or be derived from, a tissue biopsy, blood, blood plasma, extracellular fluid, dried blood spots, cultured cells, culture media, discarded tissue, plant matter, synthetic proteins, bacterial and/or viral samples, fungal tissue, archaea, or protozoans. The sample may have been isolated from the source prior to collection. Samples may comprise forensic evidence. Non-limiting examples include a fingerprint, saliva, urine, blood, stool, semen, or other bodily fluids isolated from the primary source prior to collection. In some examples, the protein is isolated from its primary source (cells, tissue, bodily fluids such as blood, environmental samples, etc.) during sample preparation. The sample may be derived from an extinct species including, but not limited to, samples derived from fossils. The protein may or may not be purified or otherwise enriched from its primary source. In some cases, the primary source is homogenized prior to further processing. In some cases, cells are lysed using a buffer such as RIPA buffer. Denaturing buffers may also be used at this stage. The sample may be filtered or centrifuged to remove lipids and particulate matter. The sample may also be purified to remove nucleic acids, or may be treated with RNases and DNases. The sample may contain intact proteins, denatured proteins, protein fragments, or partially degraded proteins.

The sample may be taken from a subject with a disease or disorder. The disease or disorder may be an infectious disease, an immune disorder or disease, a cancer, a genetic disease, a degenerative disease, a lifestyle disease, an injury, a rare disease, or an age related disease. The infectious disease may be caused by bacteria, viruses, fungi, and/or parasites. Non-limiting examples of cancers include Bladder cancer, Lung cancer, Brain cancer, Melanoma, Breast cancer, Non-Hodgkin lymphoma, Cervical cancer, Ovarian cancer, Colorectal cancer, Pancreatic cancer, Esophageal cancer, Prostate cancer, Kidney cancer, Skin cancer, Leukemia, Thyroid cancer, Liver cancer, and Uterine cancer. Some examples of genetic diseases or disorders include, but are not limited to, multiple sclerosis (MS), cystic fibrosis, Charcot-Marie-Tooth disease, Huntington's disease, Peutz-Jeghers syndrome, Down syndrome, Rheumatoid arthritis, and Tay-Sachs disease. Non-limiting examples of lifestyle diseases include obesity, diabetes, arteriosclerosis, heart disease, stroke, hypertension, liver cirrhosis, nephritis, cancer, chronic obstructive pulmonary disease (COPD), hearing problems, and chronic backache. Some examples of injuries include, but are not limited to, abrasion, brain injuries, bruising, burns, concussions, congestive heart failure, construction injuries, dislocation, flail chest, fracture, hemothorax, herniated disc, hip pointer, hypothermia, lacerations, pinched nerve, pneumothorax, rib fracture, sciatica, spinal cord injury, tendons ligaments fascia injury, traumatic brain injury, and whiplash. The sample may be taken before and/or after treatment of a subject with a disease or disorder. Samples may be taken before and/or after a treatment. Samples may be taken during a treatment or a treatment regime. Multiple samples may be taken from a subject to monitor the effects of the treatment over time. The sample may be taken from a subject known or suspected of having an infectious disease for which diagnostic antibodies are not available.

The sample may be taken from a subject suspected of having a disease or a disorder. The sample may be taken from a subject experiencing unexplained symptoms, such as fatigue, nausea, weight loss, aches and pains, weakness, or memory loss. The sample may be taken from a subject having explained symptoms. The sample may be taken from a subject at risk of developing a disease or disorder due to factors such as familial history, age, environmental exposure, lifestyle risk factors, or presence of other known risk factors.

The sample may be taken from an embryo, fetus, or pregnant woman. In some examples, the sample may comprise of proteins isolated from the mother's blood plasma. In some examples, proteins isolated from circulating fetal cells in the mother's blood.

The sample may be taken from a healthy individual. In some cases, samples may be taken longitudinally from the same individual. In some cases, samples acquired longitudinally may be analyzed with the goal of monitoring individual health and early detection of health issues. In some embodiments, the sample may be collected at a home setting or at a point-of-care setting and subsequently transported by a mail delivery, courier delivery, or other transport method prior to analysis. For example, a home user may collect a blood spot sample through a finger prick, which blood spot sample may be dried and subsequently transported by mail delivery prior to analysis. In some cases, samples acquired longitudinally may be used to monitor response to stimuli expected to impact healthy, athletic performance, or cognitive performance. Non-limiting examples include response to medication, dieting, or an exercise regimen.

Proteins of the sample may be treated to remove modifications that may interfere with epitope binding. For example, the protein may be enzymatically treated. For example, the protein may be glycosidase treated to remove post-translational glycosylation. The protein may be treated with a reducing agent to reduce disulfide binds within the protein. The protein may be treated with a phosphatase to remove phosphate groups. Other non-limiting examples of post-translational modifications that may be removed include acetate, amide groups, methyl groups, lipids, ubiquitin, myristoylation, palmitoylation, isoprenylation or prenylation (e.g., farnesol and geranylgeraniol), farnesylation, geranylgeranylation, glypiation, lipoylation, flavin moiety attachment, phosphopantetheinylation, and retinylidene Schiff base formation.

Proteins of the sample may be treated by modifying one or more residues to make them more amenable to being bound by or detected by an affinity reagent. In some cases, proteins of the sample may be treated to retain post-translational protein modifications that may facilitate or enhance epitope binding. In some examples, phosphatase inhibitors may be added to the sample. In some examples, oxidizing agents may be added to protect disulfide bonds.

Proteins of the sample may be denatured in full or in part. In some embodiments, proteins can be fully denatured. Proteins may be denatured by application of an external stress such as a detergent, a strong acid or base, a concentrated inorganic salt, an organic solvent (e.g., alcohol or chloroform), radiation, or heat. Proteins may be denatured by addition of a denaturing buffer. Proteins may also be precipitated, lyophilized, and suspended in denaturing buffer. Proteins may be denatured by heating. Methods of denaturing that are unlikely to cause chemical modifications to the proteins may be preferred.

Proteins of the sample may be treated to produce shorter polypeptides, either before or after conjugation. Remaining proteins may be partially digested with an enzyme such as ProteinaseK to generate fragments or may be left intact. In further examples the proteins may be exposed to proteases such as trypsin. Additional examples of proteases may include serine proteases, cysteine proteases, threonine proteases, aspartic proteases, glutamic proteases, metalloproteases, and asparagine peptide lyases.

In some cases, it may be useful to remove extremely large and small proteins (e.g., Titin), e.g., such proteins may be removed by filtration or other appropriate methods. In some examples, extremely large proteins may include proteins that are at least about 400 kilodalton (kD), 450 kD, 500 kD, 600 kD, 650 kD, 700 kD, 750 kD, 800 kD, or 850 kD. In some examples, extremely large proteins may include proteins that are at least about 8,000 amino acids, about 8,500 amino acids, about 9,000 amino acids, about 9,500 amino acids, about 10,000 amino acids, about 10,500 amino acids, about 11,000 amino acids, or about 15,000 amino acids. In some examples, small proteins may include proteins that are less than about 10 kD, 9 kD, 8 kD, 7 kD, 6 kD, 5 kD, 4 kD, 3 kD, 2 kD, or 1 kD. In some examples, small proteins may include proteins that are less than about 50 amino acids, 45 amino acids, 40 amino acids, 35 amino acids, or about 30 amino acids. Extremely large or small proteins can be removed by size exclusion chromatography. Extremely large proteins may be isolated by size exclusion chromatography, treated with proteases to produce moderately sized polypeptides, and recombined with the moderately size proteins of the sample.

Proteins of the sample may be tagged, e.g., with identifiable tags, to allow for multiplexing of samples. Some non-limiting examples of identifiable tags include: fluorophores, fluorescent nanoparticles, quantum dots, magnetic nanoparticles, or DNA barcoded base linkers. Fluorophores used may include fluorescent proteins such as GFP, YFP, RFP, eGFP, mCherry, tdtomato, FITC, Alexa Fluor 350, Alexa Fluor 405, Alexa Fluor 488, Alexa Fluor 532, Alexa Fluor 546, Alexa Fluor 555, Alexa Fluor 568, Alexa Fluor 594, Alexa Fluor 647, Alexa Fluor 680, Alexa Fluor 750, Pacific Blue, Coumarin, BODIPY FL, Pacific Green, Oregon Green, Cy3, Cy5, Pacific Orange, TRITC, Texas Red, Phycoerythrin, and Allophcocyanin.

Any number of protein samples may be multiplexed. For example, a multiplexed reaction may contain proteins from 2, 3, 4, 5, 6, 7, 8, 9, 10, 11, 12, 13, 14, 15, 16, 17, 18, 19, about 20, about 25, about 30, about 35, about 40, about 45, about 50, about 55, about 60, about 65, about 70, about 75, about 80, about 85, about 90, about 95, about 100, or more than about 100 initial samples. The identifiable tags may provide a way to interrogate each protein as to its sample of origin, or may direct proteins from different samples to segregate to different areas or a solid support. In some embodiments, the proteins are then applied to a functionalized substrate to chemically attach proteins to the substrate.

Any number of protein samples may be mixed prior to analysis without tagging or multiplexing. For example, a multiplexed reaction may contain proteins from 2, 3, 4, 5, 6, 7, 8, 9, 10, 11, 12, 13, 14, 15, 16, 17, 18, 19, about 20, about 25, about 30, about 35, about 40, about 45, about 50, about 55, about 60, about 65, about 70, about 75, about 80, about 85, about 90, about 95, about 100, or more than about 100 initial samples. For example, diagnostics for rare conditions may be performed on pooled samples. Analysis of individual samples may then be performed only from samples in a pool that tested positive for the diagnostic. Samples may be multiplexed without tagging using a combinatorial pooling design in which samples are mixed into pools in a manner that allows signal from individual samples to be resolved from the analyzed pools using computational demultiplexing.

The term "substrate," as used herein, generally refers to a substrate capable of forming a solid support. Substrates, or solid substrates, can refer to any solid surface to which proteins can be covalently or non-covalently attached. Non-limiting examples of solid substrates include particles, beads, slides, surfaces of elements of devices, membranes, flow cells, wells, chambers, macrofluidic chambers, microfluidic chambers, channels, microfluidic channels, or any other surfaces. Substrate surfaces can be flat or curved, or can have other shapes, and can be smooth or textured. Substrate surfaces may contain microwells. In some embodiments, the substrate can be composed of glass, carbohydrates such as dextrans, plastics such as polystyrene or polypropylene, polyacrylamide, latex, silicon, metals such as gold, or cellulose, and may be further modified to allow or enhance covalent or non-covalent attachment of the proteins. For example, the substrate surface may be functionalized by modification with specific functional groups, such as maleic or succinic moieties, or derivatized by modification with a chemically reactive group, such as amino, thiol, or acrylate groups, such as by silanization. Suitable silane reagents include aminopropyltrimethoxysilane, aminopropyltriethoxysilane and 4-aminobutyltriethoxysilane. The substrate may be functionalized with N-Hydroxysuccinimide (NHS) functional groups. Glass surfaces can also be derivatized with other reactive groups, such as acrylate or epoxy, using, e.g., epoxysilane, acrylatesilane or acrylamidesilane. The substrate and process for protein attachment are preferably stable for repeated binding, washing, imaging and eluting steps. In some examples, the substrate may be a slide, a flow cell, or a microscaled or nanoscaled structure (e.g., an ordered structure such as microwells, micropillars, single molecule arrays, nanoballs, nanopillars, or nanowires).

The spacing of the functional groups on the substrate may be ordered or random. An ordered array of functional groups may be created by, for example, photolithography, Dip-Pen nanolithography, nanoimprint lithography, nanosphere lithography, nanoball lithography, nanopillar arrays, nanowire lithography, scanning probe lithography, thermochemical lithography, thermal scanning probe lithography, local oxidation nanolithography, molecular self-assembly, stencil lithography, or electron-beam lithography. Functional groups in an ordered array may be located such that each functional group is less than 200 nanometers (nm), or about 200 nm, about 225 nm, about 250 nm, about 275 nm, about 300 nm, about 325 nm, about 350 nm, about 375 nm, about 400 nm, about 425 nm, about 450 nm, about 475 nm, about 500 nm, about 525 nm, about 550 nm, about 575 nm, about 600 nm, about 625 nm, about 650 nm, about 675 nm, about 700 nm, about 725 nm, about 750 nm, about 775 nm, about 800 nm, about 825 nm, about 850 nm, about 875 nm, about 900 nm, about 925 nm, about 950 nm, about 975 nm, about 1000 nm, about 1025 nm, about 1050 nm, about 1075 nm, about 1100 nm, about 1125 nm, about 1150 nm, about 1175 nm, about 1200 nm, about 1225 nm, about 1250 nm, about 1275 nm, about 1300 nm, about 1325 nm, about 1350 nm, about 1375 nm, about 1400 nm, about 1425 nm, about 1450 nm, about 1475 nm, about 1500 nm, about 1525 nm, about 1550 nm, about 1575 nm, about 1600 nm, about 1625 nm, about 1650 nm, about 1675 nm, about 1700 nm, about 1725 nm, about 1750 nm, about 1775 nm, about 1800 nm, about 1825 nm, about 1850 nm, about 1875 nm, about 1900 nm, about 1925 nm, about 1950 nm, about 1975 nm, about 2000 nm, or more than 2000 nm from any other functional group. Functional groups in a random spacing may be provided at a concentration such that functional groups are on average at least about 50 nm, about 100 nm, about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, about 1000 nm, or more than 100 nm from any other functional group.

The substrate may be indirectly functionalized. For example, the substrate may be PEGylated and a functional group may be applied to all or a subset of the PEG molecules. The substrate may be functionalized using techniques suitable for microscaled or nanoscaled structures (e.g., an ordered structure such as microwells, micropillars, single molecular arrays, nanoballs, nanopillars, or nanowires).

The substrate may comprise any material, including metals, glass, plastics, ceramics or combinations thereof. In some preferred embodiments, the solid substrate can be a flow cell. The flow cell can be composed of a single layer or multiple layers. For example, a flow cell can comprise a base layer (e.g., of boro silicate glass), a channel layer (e.g., of etched silicon) overlaid upon the base layer, and a cover, or top, layer. When the layers are assembled together, enclosed channels can be formed having inlet/outlets at either end through the cover. The thickness of each layer can vary, but is preferably less than about 1700 m. Layers can be composed of suitable materials such as photosensitive glasses, borosilicate glass, fused silicate, PDMS, or silicon. Different layers can be composed of the same material or different materials.

In some embodiments, flow cells can comprise openings for channels on the bottom of the flow cell. A flow cell can comprise millions of attached target conjugation sites in locations that can be discretely visualized. In some embodiments, various flow cells of use with embodiments of the invention can comprise different numbers of channels (e.g., 1 channel, 2 or more channels, 3 or more channels, 4 or more channels, 6 or more channels, 8 or more channels, 10 or more channels, 12 or more channels, 16 or more channels, or more than 16 channels). Various flow cells can comprise channels of different depths or widths, which may be different between channels within a single flow cell, or different between channels of different flow cells. A single channel can also vary in depth and/or width. For example, a channel can be less than about 50 m deep, about 50 m deep, less than about 100 m deep, about 100 m deep, about 100 m about 500 m deep, about 500 m deep, or more than about 500 m deep at one or more points within the channel. Channels can have any cross sectional shape, including but not limited to a circular, a semi-circular, a rectangular, a trapezoidal, a triangular, or an ovoid cross-section.

The proteins may be spotted, dropped, pipetted, flowed, washed or otherwise applied to the substrate. In the case of a substrate that has been functionalized with a moiety such as an NHS ester, no modification of the protein is required. In the case of a substrate that has been functionalized with alternate moieties (e.g., a sulfhydryl, amine, or linker nucleic acid), a crosslinking reagent (e.g., disuccinimidyl suberate, NHS, sulphonamides) may be used. In the case of a substrate that has been functionalized with linker nucleic acid, the proteins of the sample may be modified with complementary nucleic acid tags.

Photo-activatable cross linkers may be used to direct cross linking of a sample to a specific area on the substrate. Photo-activatable cross linkers may be used to allow multiplexing of protein samples by attaching each sample in a known region of the substrate. Photo-activatable cross linkers may allow the specific attachment of proteins which have been successfully tagged, for example, by detecting a fluorescent tag before cross linking a protein. Examples of photo-activatable cross linkers include, but are not limited to, N-5-azido-2-nitrobenzoyloxysuccinimide, sulfosuccinimidyl 6-(4'-azido-2'-nitrophenylamino)hexanoate, succinimidyl 4,4'-azipentanoate, sulfosuccinimidyl 4,4'-azipentanoate, succinimidyl 6-(4,4'-azipentanamido)hexanoate, sulfosuccinimidyl 6-(4,4'-azipentanamido)hexanoate, succinimidyl 2-((4,4'-azipentanamido)ethyl)-1,3'-dithiopropionate, and sulfosuccinimidyl 2-((4,4'-azipentanamido)ethyl)-1,3'-dithiopropionate.

The polypeptides may be attached to the substrate by one or more residues. In some examples, the polypeptides may be attached via the N terminal, C terminal, both terminals, or via an internal residue.

In addition to permanent crosslinkers, it may be appropriate for some applications to use photo-cleavable linkers and that doing so enables proteins to be selectively extracted from the substrate following analysis. In some cases photo-cleavable cross linkers may be used for several different multiplexed samples. In some cases photo-cleavable cross linkers may be used from one or more samples within a multiplexed reaction. In some cases a multiplexed reaction may comprise control samples cross linked to the substrate via permanent crosslinkers and experimental samples cross linked to the substrate via photo-cleavable crosslinkers.

Each conjugated protein may be spatially separated from each other conjugated protein such that each conjugated protein is optically resolvable. Proteins may thus be individually labeled with a unique spatial address. In some embodiments, this can be accomplished by conjugation using low concentrations of protein and low density of attachment sites on the substrate so that each protein molecule is spatially separated from each other protein molecule. In examples where photo-activatable crosslinkers are used a light pattern may be used such that proteins are affixed to predetermined locations.

In some embodiments, each protein may be associated with a unique spatial address. For example, once the proteins are attached to the substrate in spatially separated locations, each protein can be assigned an indexed address, such as by coordinates. In some examples, a grid of pre-assigned unique spatial addresses may be predetermined. In some embodiments the substrate may contain easily identifiable fixed marks such that placement of each protein can be determined relative to the fixed marks of the substrate. In some examples, the substrate may have grid lines and/or and "origin" or other fiducials permanently marked on the surface. In some examples, the surface of the substrate may be permanently or semi-permanently marked to provide a reference by which to locate cross linked proteins. The shape of the patterning itself, such as the exterior border of the conjugated polypeptides, may also be used as fiducials for determining the unique location of each spot.

The substrate may also contain conjugated protein standards and controls. Conjugated protein standards and controls may be peptides or proteins of known sequence which have been conjugated in known locations. In some examples, conjugated protein standards and controls may serve as internal controls in an assay. The proteins may be applied to the substrate from purified protein stocks, or may be synthesized on the substrate through a process such as Nucleic Acid-Programmable Protein Array (NAPPA).

In some examples, the substrate may comprise fluorescent standards. These fluorescent standards may be used to calibrate the intensity of the fluorescent signals from assay to assay. These fluorescent standards may also be used to correlate the intensity of a fluorescent signal with the number of fluorophores present in an area. Fluorescent standards may comprise some or all of the different types of fluorophores used in the assay.

Once the substrate has been conjugated with the proteins from the sample, multi-affinity reagent measurements can be performed. The measurement processes described herein may utilize various affinity reagents. In some embodiments, multiple affinity reagents may be mixed together and measurements may be performed on the binding of the affinity reagent mixture to the protein-substrate conjugate. In some cases, measurements performed on the binding of affinity reagent mixtures may vary across different solvent conditions and/or protein folding conditions; therefore, repeated measurements may be performed on the same affinity reagent or set of affinity reagents, under such varying solvent conditions and/or protein folding conditions, in order to obtain different sets of binding measurements. In some cases, different sets of binding measurements may be obtained by performing repeated measurements on samples in which proteins have been enzymatically treated (e.g., with glycosidase, phosphorylase, or phosphatase) or not enzymatically treated.

The term "affinity reagent," as used herein, generally refers to a reagent that binds proteins or peptides with reproducible specificity. For example, the affinity reagents may be antibodies, antibody fragments, aptamers, mini-protein binders, or peptides. In some embodiments, mini-protein binders may comprise protein binders that may be between 30-210 amino acids in length. In some embodiments, mini-protein binders may be designed. For example, protein binders may include peptide macrocycles, (e.g., as described in [Hosseinzadeh et al., "Comprehensive computational design of ordered peptide macrocycles," *Science*, 2017 Dec. 15; 358(6369): 1461-1466], which is incorporated herein by reference in its entirety). In some embodiments, monoclonal antibodies may be preferred. In some embodiments, antibody fragments such as Fab fragments may be preferred. In some embodiments, the affinity reagents may be commercially available affinity reagents, such as commercially available antibodies. In some embodiments, the desired affinity reagents may be selected by screening commercially available affinity reagents to identify those with useful characteristics.

The affinity reagents may have high, moderate, or low specificity. In some examples, the affinity reagents may recognize several different epitopes. In some examples, the affinity reagents may recognize epitopes present in two or more different proteins. In some examples, the affinity reagents may recognize epitopes present in many different proteins. In some cases, an affinity reagent used in the methods of this disclosure may be highly specific for a single epitope. In some cases, an affinity reagent used in the methods of this disclosure may be highly specific for a single epitope containing a post-translational modification. In some cases, affinity reagents may have highly similar epitope specificity. In some cases, affinity reagents with highly similar epitope specificity may be designed specifically to resolve highly similar protein candidate sequences (e.g. candidates with single amino acid variants or isoforms). In some cases, affinity reagents may have highly diverse epitope specificity to maximize protein sequence coverage. In some embodiments, experiments may be performed in replicate with the same affinity probe with the expectation that the results may differ, and thus provide additional information for protein identification, due to the stochastic nature of probe binding to the protein-substrate.

In some cases, the specific epitope or epitopes recognized by an affinity reagent may not be fully known. For example, affinity reagents may be designed or selected for binding specifically to one or more whole proteins, protein complexes, or protein fragments without knowledge of a specific binding epitope. Through a qualification process, the binding profile of this reagent may have been elaborated. Even though the specific binding epitope(s) are unknown, binding measurements using said affinity reagent may be used to determine protein identity. For example, a commercially-available antibody or aptamer designed for binding to a protein target may be used as an affinity reagent. Following qualification under assay conditions (e.g., fully folded, partially denaturing, or fully denaturing), binding of this affinity reagent to an unknown protein may provide information about the identity of the unknown protein. In some cases, a collection of protein-specific affinity reagents (e.g., commercially-available antibodies or aptamers) may be used to generate protein identifications, either with or without knowledge of the specific epitopes they target. In some cases, the collection of protein-specific affinity reagents may comprise about 50, 100, 200, 300, 400, 500, 600, 700, 800, 900, 1000, 2000, 3000, 4000, 5000, 10000, 20000, or more than 20000 affinity reagents. In some cases, the collection of affinity reagents may comprise all commercially-available affinity reagents demonstrating target-reactivity in a specific organism. For example, a collection of protein-specific affinity reagents may be assayed in series, with binding measurements for each affinity reagent made individually. In some cases, subsets of the protein-specific affinity reagents may be mixed prior to binding measurement. For example, for each binding measurement pass, a new mixture of affinity reagents may be selected comprising a subset of the affinity reagents selected at random from the complete set. For example, each subsequent mixture may be generated in the same random manner, with the expectation that many of the affinity reagents will be present in more than one of the mixtures. In some cases, protein identifications may be generated more rapidly using mixtures of protein-specific affinity reagents. In some cases, such mixtures of protein-specific affinity reagents may increase the percentage of unknown proteins for which an affinity reagent binds in any individual pass. Mixtures of affinity reagents may comprise about 1%, 5%, 10%, 20%, 30%, 40%, 50%, 60%, 70%, 80%, 90%, or more than 90% of all available affinity reagents. Mixtures of affinity reagents assessed in a single experiment may or may not share individual affinity reagents in common. In some cases, there may be multiple different affinity reagents within a collection that bind to the same protein. In some cases, each affinity reagent in the collection may bind to a different protein. In cases where multiple affinity reagents with affinity for the same protein bind to a single unknown protein, confidence in the identity of the unknown protein being the common target of said affinity reagents may increase. In some cases, using multiple protein affinity reagents targeting the same protein may provide redundancy in cases where the multiple affinity reagents bind different epitopes on the same protein, and binding of only a subset of the affinity reagents targeting that protein may be interfered with by post-translational modifications or other steric hinderance of a binding epitope. In some cases, binding of affinity reagents for which the binding epitope is unknown may be used in conjunction with binding measurements of affinity reagents for which the binding epitope is known to generate protein identifications.

In some examples, one or more affinity reagents may be chosen to bind amino acid motifs of a given length, such as 2, 3, 4, 5, 6, 7, 8, 9, 10, or more than 10 amino acids. In some examples, one or more affinity reagents may be chosen to bind amino acid motifs of a range of different lengths from 2 amino acids to 40 amino acids.

In some cases, the affinity reagents may be labeled with nucleic acid barcodes. In some examples, nucleic acid barcodes may be used to purify affinity reagents after use. In some examples, nucleic acid barcodes may be used to sort the affinity reagents for repeated uses. In some cases, the affinity reagents may be labeled with fluorophores which may be used to sort the affinity reagents after use.

The family of affinity reagents may comprise one or more types of affinity reagents. For example, the methods of the present disclosure may use a family of affinity reagents comprising one or more of antibodies, antibody fragments, Fab fragments, aptamers, peptides, and proteins.

The affinity reagents may be modified. Examples of modifications include, but are not limited to, attachment of a detection moiety. Detection moieties may be directly or indirectly attached. For example, the detection moiety may be directly covalently attached to the affinity reagent, or may be attached through a linker, or may be attached through an affinity reaction such as complementary nucleic acid tags or a biotin streptavidin pair. Attachment methods that are able to withstand gentle washing and elution of the affinity reagent may be preferred.

Affinity reagents may be tagged, e.g., with identifiable tags, to allow for identification or quantification of binding events (e.g., with fluorescence detection of binding events). Some non-limiting examples of identifiable tags include: fluorophores, magnetic nanoparticles, or nucleic acid barcoded base linkers. Fluorophores used may include fluorescent proteins such as GFP, YFP, RFP, eGFP, mCherry, tdtomato, FITC, Alexa Fluor 350, Alexa Fluor 405, Alexa Fluor 488, Alexa Fluor 532, Alexa Fluor 546, Alexa Fluor 555, Alexa Fluor 568, Alexa Fluor 594, Alexa Fluor 647, Alexa Fluor 680, Alexa Fluor 750, Pacific Blue, Coumarin, BODIPY FL, Pacific Green, Oregon Green, Cy3, Cy5, Pacific Orange, TRITC, Texas Red, Phycoerythrin, and Allophcocyanin. Alternatively, affinity reagents may be untagged, such as when binding events are directly detected, e.g., with surface plasmon resonance (SPR) detection of binding events.

Examples of detection moieties include, but are not limited to, fluorophores, bioluminescent proteins, nucleic acid segments including a constant region and barcode region, or chemical tethers for linking to a nanoparticle such as a magnetic particle. For example, affinity reagents may be tagged with DNA barcodes, which can then be explicitly sequenced at their locations. As another example, sets of different fluorophores may be used as detection moieties by fluorescence resonance energy transfer (FRET) detection methods. Detection moieties may include several different fluorophores with different patterns of excitation or emission.

The detection moiety may be cleavable from the affinity reagent. This can allow for a step in which the detection moieties are removed from affinity reagents that are no longer of interest to reduce signal contamination.

In some cases, the affinity reagents are unmodified. For example, if the affinity reagent is an antibody then the presence of the antibody may be detected by atomic force microscopy. The affinity reagents may be unmodified and may be detected, for example, by having antibodies specific to one or more of the affinity reagents. For example, if the affinity reagent is a mouse antibody, then the mouse antibody may be detected by using an anti-mouse secondary antibody. Alternatively, the affinity reagent may be an aptamer which is detected by an antibody specific for the aptamer. The secondary antibody may be modified with a detection moiety as described above. In some cases, the presence of the secondary antibody may be detected by atomic force microscopy.

In some examples, the affinity reagents may comprise the same modification, for example, a conjugated green fluorescent protein, or may comprise two or more different types of modification. For example, each affinity reagent may be conjugated to one of several different fluorescent moieties, each with a different wavelength of excitation or emission. This may allow multiplexing of the affinity reagents as several different affinity reagents may be combined and/or distinguished. In one example, a first affinity reagent may be conjugated to a green fluorescent protein, a second affinity reagent may be conjugated to a yellow fluorescent protein and a third affinity reagent may be conjugated to a red fluorescent protein, thus the three affinity reagents can be multiplexed and identified by their fluorescence. In a further example a first, fourth, and seventh affinity reagent may be conjugated to a green fluorescent protein, a second, fifth, and eighth affinity reagent may be conjugated to a yellow fluorescent protein, and a third, sixth, and ninth affinity reagent may be conjugated to a red fluorescent protein; in this case, the first, second, and third affinity reagents may be multiplexed together while the second, fourth, and seventh affinity reagents and the third, sixth, and ninth affinity reagents form two further multiplexing reactions. The number of affinity reagents which can be multiplexed together may depend on the detection moieties used to differentiate them. For example, the multiplexing of affinity reagents labeled with fluorophores may be limited by the number of unique fluorophores available. For further example, the multiplexing of affinity reagents labeled with nucleic acid tags may be determined by the length of the nucleic acid bar code. Nucleic acids may be deoxyribonucleic acid (DNA) or ribonucleic acid (RNA).

The specificity of each affinity reagent can be determined prior to use in an assay. The binding specificity of the affinity reagents can be determined in a control experiment using known proteins. Any appropriate experimental methods may be used to determine the specificity of the affinity reagent. In one example, a substrate may be loaded with known protein standards at known locations and used to assess the specificity of a plurality of affinity reagents. In another example, a substrate may contain both experimental samples and a panel of controls and standards, such that the specificity of each affinity reagent can be calculated from the binding to the controls and standards and then used to identify the experimental samples. In some cases, affinity reagents with unknown specificity may be included along with affinity reagents of known specificity, data from the known specificity affinity reagents may be used to identify proteins, and the pattern of binding of the unknown specificity affinity reagents to the identified proteins may be used to determine their binding specificity. It is also possible to reconfirm the specificity of any individual affinity reagent by using the known binding data of other affinity reagents to assess which proteins the individual affinity reagent bound. In some cases, the frequency of binding of the affinity reagent to each known protein conjugated to the substrate may be used to derive a probability of binding to any of the proteins on the substrate. In some cases, the frequency of binding to known proteins containing an epitope (e.g., an amino acid sequence or post-translational modification) may be used to determine the probability of binding of the affinity reagent to a particular epitope. Thus with multiple uses of an affinity reagent panel, the specificities of the affinity reagents may be increasingly refined with each iteration. While affinity reagents that are uniquely specific to particular proteins may be used, methods described herein may not require them. Additionally, methods may be effective on a range of specificities. In some examples, methods described herein may be particularly efficient when affinity reagents are not specific to any particular protein, but are instead specific to amino acid motifs (e.g., the tri-peptide AAA).

In some examples, the affinity reagents may be chosen to have high, moderate, or low binding affinities. In some cases, affinity reagents with low or moderate binding affinities may be preferred. In some cases, the affinity reagents may have dissociation constants of about $10^{-3}$ M, $10^{-4}$ M, $10^{-5}$ M, $10^{-6}$ M, $10^{-7}$ M, $10^{-8}$ M, $10^{-9}$ M, $10^{-10}$M, or less than about $10^{-10}$M. In some cases the affinity reagents may have dissociation constants of greater than about $10^{-10}$M, $10^{-9}$ M, $10^{-8}$ M, $10^{-7}$ M, $10^{-6}$ M, $10^{-5}$ M, $10^{-4}$ M, $10^{-3}$ M, $10^{-2}$ M, or greater than $10^{-2}$ M. In some cases, affinity reagents with low or moderate $k_{off}$ rates or moderate or high $k_{on}$ rates may be preferred.

Some of the affinity reagents may be chosen to bind modified amino acid sequences, such as phosphorylated or ubiquitinated amino acid sequences. In some examples, one or more affinity reagents may be chosen to be broadly specific for a family of epitopes that may be contained by one or more proteins. In some examples, one or more affinity reagents may bind two or more different proteins. In some examples, one or more affinity reagents may bind weakly to their target or targets. For example, affinity reagents may bind less than 10%, less than 10%, less than 15%, less than 20%, less than 25%, less than 30%, or less than 35% to their target or targets. In some examples, one or more affinity reagents may bind moderately or strongly to their target or targets. For example, affinity reagents may bind more than 35%, more than 40%, more than 45%, more than 60%, more than 65%, more than 70%, more than 75%, more than 80%, more than 85%, more than 90%, more than 91%, more than 92%, more than 93%, more than 94%, more than 95%, more than 96%, more than 97%, more than 98%, or more than 99% to their target or targets.

To compensate for weak binding, an excess of the affinity reagent may be applied to the substrate. The affinity reagent may be applied at about a 1:1, 2:1, 3:1, 4:1, 5:1, 6:1, 7:1, 8:1, 9:1, or 10:1 excess relative to the sample proteins. The affinity reagent may be applied at about a 1:1, 2:1, 3:1, 4:1, 5:1, 6:1, 7:1, 8:1, 9:1, or 10:1 excess relative to the expected incidence of the epitope in the sample proteins.

To compensate for high affinity reagent dissociation rates, a linker moiety may be attached to each affinity reagent and used to reversibly link bound affinity reagents to the substrate or unknown protein to which it binds. For example, a DNA tag may be attached to the end of each affinity reagent and a different DNA tag attached to the substrate or each unknown protein. After the affinity reagent is hybridized with the unknown proteins, a linker DNA complementary to the affinity reagent-associated DNA tag on one end and the substrate-associated tag on the other may be washed over the chip to bind the affinity reagent to the substrate and prevent the affinity reagent from dissociating prior to measurement. After binding, the linked affinity reagent may be released by washing in the presence of heat or high salt concentration to disrupt the DNA linker bond.

Figure 21:
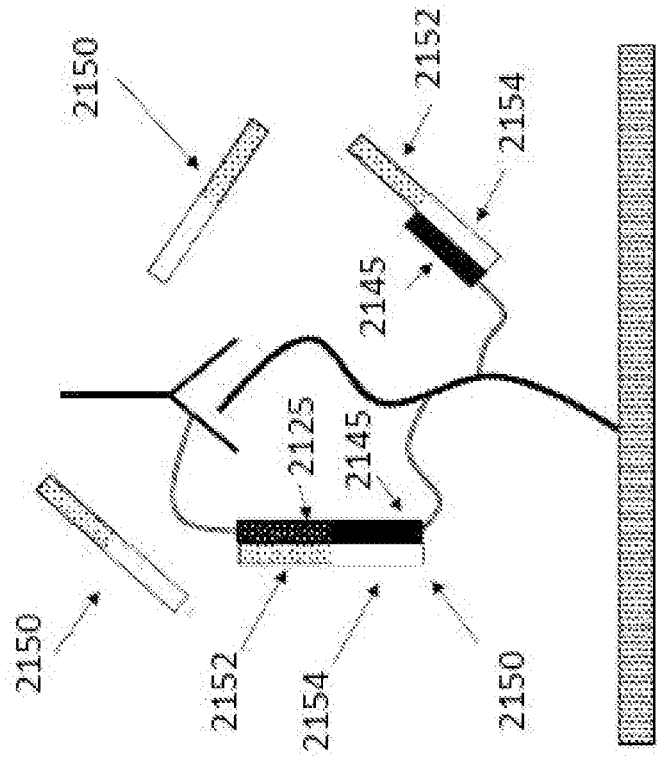
FIG. 21 illustrates two hybridization steps in reinforcing a binding between an affinity reagent and a protein, in accordance with some embodiments.
Figure 21:
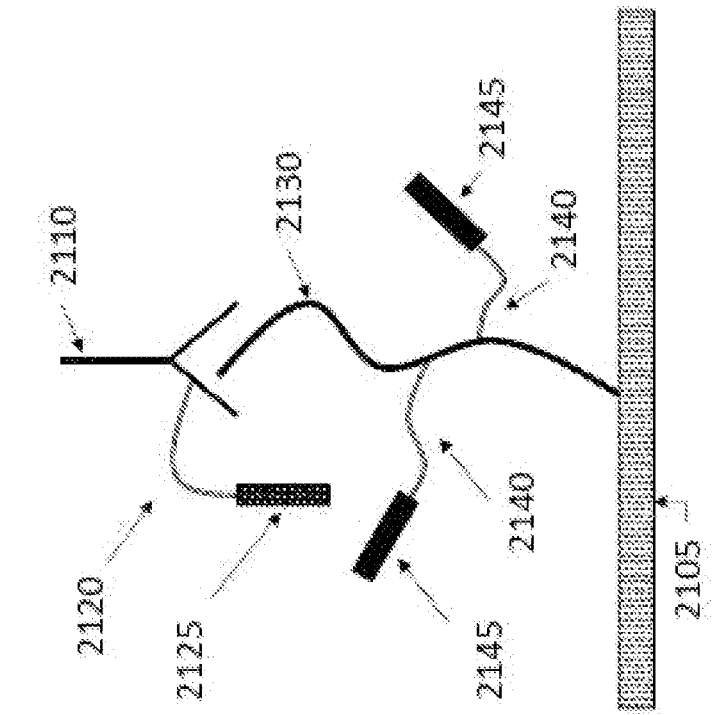

FIG. 21 illustrates two hybridization steps in reinforcing a binding between an affinity reagent and a protein, in accordance with some embodiments. In particular, step 1 of FIG. 21 illustrates an affinity reagent hybridization. As seen in step 1, affinity reagent 2110 hybridizes to protein 2130. Protein 2130 is bound to a slide 2105. As seen in step 1, affinity reagent 2110 has a DNA tag 2120 attached. In some embodiments, an affinity reagent may have more than one DNA tag attached. In some embodiments, an affinity reagent may have 1, 2, 3, 4, 5, 6, 7, 8, 9, 10, 11, 12, 13, 14, 15, 16, 17, 18, 19, 20, or more than 20 DNA tags attached. DNA tag 2120 comprises a single-stranded DNA (ssDNA) tag having a recognition sequence 2125. Additionally, protein 2130 comprises two DNA tags 2140. In some embodiments, DNA tags may be added using chemistry that reacts with cysteines in a protein. In some embodiments, a protein may have more than one DNA tag attached. In some embodiments, a protein may have 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, or more than 100 DNA tags attached. Each DNA tag 2140 comprises an ssDNA tag having a recognition sequence 2145.

As seen in step 2, DNA linker 2150 hybridizes to DNA tags 2120 and 2140 attached to affinity reagent 2110 and protein 2130, respectively. DNA linker 2150 comprises ssDNA having complementary sequences to recognition sequences 2125 and 2145, respectively. Further, recognition sequences 2125 and 2145 are situated on DNA linker 2150 so as to allow for DNA linker 2150 to bind to both DNA tags 2120 and 2140 at the same time, as illustrated in step 2. In particular, a first region 2152 of DNA linker 2150 selectively hybridizes to recognition sequence 2125, and a second region 2154 of DNA linker 2150 selectively hybridizes to recognition sequence 2145. In some embodiments, first region 2152 and second region 2154 may be spaced apart from each other on the DNA linker. In particular, in some embodiments, a first region of a DNA linker and a second region of a DNA linker may be spaced apart with a non-hybridizing spacer sequence between the first region and the second region. Further, in some embodiments, a sequence of recognition sequence may be less than fully complementary to a DNA linker and may still bind to the DNA linker sequence. In some embodiments, a length of a recognition sequence may be less than 5 nucleotides, 5 nucleotides, 6 nucleotides, 7 nucleotides, 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, or 30 nucleotides, or more than 30 nucleotides. In some embodiments, a recognition sequence may have one or more mismatches to a complementary DNA tag sequence. In some embodiments, approximately 1 in 10 nucleotides of a recognition sequence may be mismatched with a complementary DNA tag sequence and may still hybridize with the complementary DNA tag sequence. In some embodiments, less than 1 in 10 nucleotides of a recognition sequence may be mismatched with a complementary DNA tag sequence and may still hybridize with the complementary DNA tag sequence. In some embodiments, approximately 2 in 10 nucleotides of a recognition sequence may be mismatched with a complementary DNA tag sequence and may still hybridize with the complementary DNA tag sequence. In some embodiments, more than 2 in 10 nucleotides of a recognition sequence may be mismatched with a complementary DNA tag sequence and may still hybridize with the complementary DNA tag sequence.

The affinity reagents may also comprise a magnetic component. The magnetic component may be useful for manipulating some or all bound affinity reagents into the same imaging plane or z stack. Manipulating some or all affinity reagents into the same imaging plane may improve the quality of the imaging data and reduce noise in the system.

The term "detector," as used herein, generally refers to a device that is capable of detecting a signal, including a signal indicative of the presence or absence of a binding event of an affinity reagent to a protein. The signal may be a direct signal indicative of the presence or absence of a binding event, such as a surface plasmon resonance (SPR) signal. The signal may be an indirect signal indicative of the presence or absence of a binding event, such as a fluorescent signal. In some cases, a detector can include optical and/or electronic components that can detect signals. The term "detector" may be used in detection methods. Non-limiting examples of detection methods include optical detection, spectroscopic detection, electrostatic detection, electrochemical detection, magnetic detection, fluorescence detection, surface plasmon resonance (SPR), and the like. Examples of optical detection methods include, but are not limited to, fluorimetry and UV-vis light absorbance. Examples of spectroscopic detection methods include, but are not limited to, mass spectrometry, nuclear magnetic resonance (NMR) spectroscopy, and infrared spectroscopy. Examples of electrostatic detection methods include, but are not limited to, gel based techniques, such as, gel electrophoresis. Examples of electrochemical detection methods include, but are not limited to, electrochemical detection of amplified product after high-performance liquid chromatography separation of the amplified products.

Protein Identification in a Sample

Proteins are vital building blocks of cells and tissues of living organisms. A given organism produces a large set of different proteins, typically referred to as the proteome. The proteome may vary with time and as a function of various stages (e.g., cell cycle stages or disease states) that a cell or organism undergoes. A large-scale study or measurement (e.g., experimental analysis) of proteomes may be referred to as proteomics. In proteomics, multiple methods exist to identify proteins, including immunoassays (e.g., enzyme-linked immunosorbent assay (ELISA) and Western blot), mass spectroscopy-based methods (e.g., matrix-assisted laser desorption/ionization (MALDI) and electrospray ionization (ESI)), hybrid methods (e.g., mass spectrometric immunoassay (MSIA)), and protein microarrays. For example, single-molecule proteomics methods may attempt to infer the identity of protein molecules in a sample by diverse approaches, ranging from direct functionalization of amino acids to using affinity reagents. The information or measurements gathered from such approaches are typically analyzed by suitable algorithms to identify the proteins present in the sample.

Accurate quantification of proteins may also encounter challenges owing to lack of sensitivity, lack of specificity, and detector noise. In particular, accurate quantification of proteins in a sample may encounter challenges owing to random and unpredictable systematic variations in signal level of detectors, which can cause errors in identifying and quantifying proteins. In some cases, instrument and detection systematics can be calibrated and removed by monitoring instrument diagnostics and common-mode behavior. However, binding of proteins (e.g., by affinity reagent probes) is inherently a probabilistic process which may have less than ideal sensitivity and specificity of binding.

The present disclosure provides methods and systems for accurate and efficient identification of proteins. Methods and systems provided herein can significantly reduce or eliminate errors in identifying proteins in a sample. Such methods and systems may achieve accurate and efficient identification of candidate proteins within a sample of unknown proteins. The protein identification may be based on calculations using information of empirical measurements of the unknown proteins in the sample. For example, empirical measurements may include binding information of affinity reagent probes which are configured to selectively bind to one or more candidate proteins, protein length, protein hydrophobicity, and/or isoelectric point. The protein identification may be optimized to be computable within a minimal memory footprint. The protein identification may comprise estimation of a confidence level that each of one or more candidate proteins is present in the sample.

In an aspect, disclosed herein is a computer-implemented method 100 for identifying a protein within a sample of unknown proteins (e.g., as illustrated in FIG. 1). The method may be applied independently to each unknown protein in the sample, to generate a collection of proteins identified in the sample. Protein quantities may be calculated by counting the number of identifications for each candidate protein. The method for identifying a protein may comprise receiving, by the computer, information of a plurality of empirical measurements of the unknown protein in the sample (e.g., step 105). The empirical measurements may comprise (i) binding measurements of each of one or more affinity reagent probes to one or more of the unknown proteins in the sample, (ii) length of one or more of the unknown proteins; (iii) hydrophobicity of one or more of the unknown proteins; and/or (iv) isoelectric point of one or more of the unknown proteins. In some embodiments, a plurality of affinity reagent probes may comprise a pool of a plurality of individual affinity reagent probes. For example, a pool of affinity reagent probes may comprise 2, 3, 4, 5, 6, 7, 8, 9, 10, or more than 10 types of affinity reagent probes. In some embodiments, a pool of affinity reagent probes may comprise 2 types of affinity reagent probes that combined make up a majority of the composition of the affinity reagent probes in the pool of affinity reagent probes. In some embodiments, a pool of affinity reagent probes may comprise 3 types of affinity reagent probes that combined make up a majority of the composition of the affinity reagent probes in the pool of affinity reagent probes. In some embodiments, a pool of affinity reagent probes may comprise 4 types of affinity reagent probes that combined make up a majority of the composition of the affinity reagent probes in the pool of affinity reagent probes. In some embodiments, a pool of affinity reagent probes may comprise 5 types of affinity reagent probes that combined make up a majority of the composition of the affinity reagent probes in the pool of affinity reagent probes. In some embodiments, a pool of affinity reagent probes may comprise more than 5 types of affinity reagent probes that combined make up a majority of the composition of the affinity reagent probes in the pool of affinity reagent probes. Each of the affinity reagent probes may be configured to selectively bind to one or more candidate proteins among the plurality of candidate proteins. The affinity reagent probes may be k-mer affinity reagent probes. In some embodiments, each k-mer affinity reagent probe is configured to selectively bind to one or more candidate proteins among a plurality of candidate proteins. The information of empirical measurements may comprise binding measurements of a set of probes that are believed to have bound to an unknown protein.

Next, at least a portion of the information of empirical measurements of an unknown protein may be compared, by the computer, against a database comprising a plurality of protein sequences (e.g., step 110). Each of the protein sequences may correspond to a candidate protein among the plurality of candidate proteins. The plurality of candidate proteins may comprise at least 10, at least 20, at least 30, at least 40, at least 50, at least 60, at least 70, at least 80, at least 90, at least 100, at least 150, at least 200, at least 250, at least 300, at least 350, at least 400, at least 450, at least 500, at least 600, at least 700, at least 800, at least 900, at least 1000, or more than 1000 different candidate proteins.

Next, for each of one or more candidate proteins in the plurality of candidate proteins, a probability that an empirical measurement on the candidate protein would generate an observed measurement outcome may be calculated or generated, by the computer (e.g., in step 115). The term "measurement outcome," as used herein, refers to the information observed on performing a measurement. For example, the measurement outcome of an affinity reagent binding experiment may be a positive or negative outcome, such as either binding or non-binding of the reagent. As another example, the measurement outcome of an experiment measuring the length of a protein may be 417 amino acids. Additionally, or alternatively, for each of one or more candidate proteins in the plurality of candidate proteins, a probability that an empirical measurement on the candidate protein would not generate an observed measurement outcome, may be calculated or generated, by the computer. Additionally, or alternatively, a probability that an empirical measurement on the candidate protein would generate an unobserved measurement outcome, may be calculated or generated by the computer. Additionally, or alternatively, a probability that a series of empirical measurements on the candidate protein would generate an outcome set may be calculated or generated, by the computer.

"Outcome set," as used herein, refers to a plurality of independent measurement outcomes for a protein. For example, a series of empirical affinity reagent binding measurements may be performed on a unknown protein. The binding measurement of each individual affinity reagent comprises a measurement outcome, and the set of all measurement outcomes is the outcome set. In some cases, the outcome set may be a subset of all observed outcomes. In some cases, the outcome set may consist of measurement outcomes that were not empirically observed. Additionally or alternatively, for each of one or more candidate proteins in the plurality of candidate proteins, a probability that the unknown protein is the candidate protein, may be calculated or generated, by the computer. The calculation or generation of steps 115 and/or 120 may be performed iteratively or non-iteratively. The probabilities in step 115 may be generated based on the comparison of the empirical measurement outcomes of the unknown proteins against the database comprising the plurality of protein sequences for all candidate proteins. Thus, the input to the algorithm may comprise a database of candidate protein sequences and a set of empirical measurements (e.g., probes that are believed to have bound to an unknown protein, length of the unknown protein, hydrophobicity of the unknown protein, and/or isoelectric point of the unknown protein) for the unknown protein. In some cases, the input to the algorithm may comprise parameters relevant to estimating the probability of any of the affinity reagents generating any binding measurement for any of the candidate proteins (e.g. trimer-level binding probabilities for each affinity reagent). The output of the algorithm may comprise (i) a probability that a measurement outcome or outcome set is observed given a hypothesized candidate protein identity, (ii) the most probable identity, selected from the set of candidate proteins, for the unknown protein and the probability of that identification being correct given a measurement outcome or outcome set (e.g., in step 120), and/or (iii) a group of high-probability candidate protein identities and an associated probability that the unknown protein is one of the proteins in the group. The probability that the measurement outcome is observed given that a candidate protein is the protein being measured may be expressed as:

$$P(\text{measurement outcome}|\text{protein}).$$

In some embodiments, P(measurement outcome|protein) is calculated completely in silico. In some embodiments, P(measurement outcome|protein) is calculated based on, or derived from, features of the amino acid sequence of the protein. In some embodiments, P(measurement outcome|protein) is calculated independent of knowledge of the amino acid sequence of the protein. For example, P(measurement outcome|protein) may be determined empirically by acquiring the measurement in replicate experiments on an isolate of the protein candidate, and calculating the P(measurement outcome|protein) from the frequency: (number of measurements with outcome/total number of measurements). In some embodiments, P(measurement outcome|protein) is derived from a database of past measurements on the protein. In some embodiments P(measurement outcome|protein) is calculated by generating a set of confident protein identifications from a collection of unknown proteins with the results of the measurement censored, and then calculating the frequency of the measurement outcome among the set of unknown proteins that were confidently identified as the candidate protein. In some embodiments, a collection of unknown proteins may be identified using a seed value of P(measurement outcome|protein), and the seed value refined based on the frequency of the measurement outcome among unknown proteins confidently matched to the candidate protein. In some embodiments, this process is repeated, with new identifications generated based on updated measurement outcome probabilities, and then new measurement outcome probabilities generated from the updated set of confident identifications.

The probability that the measurement outcome is not observed given that a candidate protein is the protein being measured, may be expressed as:

$$P(\text{not measurement outcome}|\text{protein})=1-P(\text{measurement outcome}|\text{protein}).$$

The probability that a measurement outcome set consisting of N individual measurement outcomes is observed given that a candidate protein is the protein being measured, may be expressed as a product of the probabilities for each individual measurement outcome:

$$P(\text{outcome set}|\text{protein})=P(\text{measurement outcome 1}|\text{protein})*P(\text{measurement outcome 2}|\text{protein})* \ldots *P(\text{measurement outcome } N|\text{protein})$$

The probability of the unknown protein being a candidate protein (protein$_i$), may be calculated based on the probability of the outcome set for each possible candidate protein.

In some embodiments, the measurement outcome set comprises binding of affinity reagent probes. In some embodiments, the measurement outcome set comprises non-specific binding of affinity reagent probes.

In some embodiments, the protein in the sample is truncated or degraded. In some embodiments, the protein in the sample does not contain the C-terminus of the original protein. In some embodiments, the protein in the sample does not contain the N-terminus of the original protein. In some embodiments, the protein in the sample does not contain the N-terminus and does not contain the C-terminus of the original protein.

In some embodiments, the empirical measurements comprise measurements performed on mixtures of antibodies. In some embodiments, the empirical measurements comprise measurements performed on samples containing proteins from a plurality of species. In some embodiments, the empirical measurements comprise measurements performed on a sample derived from humans. In some embodiments, the empirical measurements comprise measurements performed on a sample derived from a different species than human. In some embodiments, the empirical measurements comprise measurements performed on samples in the presence of single amino acid variants (SAVs) caused by non-synonymous single-nucleotide polymorphisms (SNPs). In some embodiments, the empirical measurements comprise measurements on samples in the presence of genomic structural variation, such as insertions, deletions, translocations, inversions, segmental duplications, or copy number variation (CNV) affecting the sequence of the proteins in the sample.

In some embodiments, the method further comprises applying the method to all unknown proteins measured in the sample. In some embodiments, the method further comprises generating, for each of the one or more candidate proteins, a confidence level that the candidate protein matches the unknown protein being measured in the sample. The confidence level may comprise a probability value. Alternatively, the confidence level may comprise a probability value with an error. Alternatively, the confidence level may comprise a range of probability values, optionally with a confidence (e.g., about 90%, about 95%, about 96%, about 97%, about 98%, about 99%, about 99.9%, about 99.99%, about 99.999%, about 99.9999%, about 99.99999%, about 99.999999%, about 99.9999999%, about 99.99999999%, about 99.999999999%, about 99.9999999999%, about 99.99999999999%, about 99.999999999999%, about 99.9999999999999% confidence, or above 99.9999999999999% confidence).

In some embodiments, the method further comprises generating a probability that a candidate protein is present in the sample.

In some embodiments, the method further comprises generating protein identifications, and associated probabilities, independently for each unknown protein in the sample, and generating a list of all unique proteins identified in the sample. In some embodiments, the method further comprises counting the number of identifications generated for each unique candidate protein to determine the quantity of each candidate protein in the sample. In some embodiments, a collection of protein identifications and associated probabilities may be filtered to only contain identifications of a high score, high confidence, and/or low false discovery rate.

In some embodiments, binding probabilities may be generated for affinity reagents to full-length candidate proteins. In some embodiments, binding probabilities may be generated for affinity reagents to protein fragments (e.g., a subsequence of the complete protein sequence). For example, if unknown proteins were processed and conjugated to the substrate in a manner such that only the first 100 amino acids of each unknown protein were conjugated, binding probabilities may be generated for each protein candidate such that all binding probabilities for epitope binding beyond the first 100 amino acids are set to zero, or alternatively to a very low probability representing an error rate. A similar approach may be used if the first 10, 20, 50, 100, 150, 200, 300, 400, or more than 400 amino acids of each protein are conjugated to the substrate. A similar approach may be used if the last 10, 20, 50, 100, 150, 200, 300, 400, or more than 400 amino acids are conjugated to the substrate.

In some embodiments, in cases where a single protein candidate match cannot be assigned to an unknown protein, a group of potential protein candidate matches may be assigned to the unknown protein. A confidence level may be assigned to the unknown protein being one of any of the protein candidates in the group. The confidence level may comprise a probability value. Alternatively, the confidence level may comprise a probability value with an error. Alternatively, the confidence level may comprise a range of probability values, optionally with a confidence (e.g., about 90%, about 95%, about 96%, about 97%, about 98%, about 99%, about 99.9%, about 99.99%, about 99.999%, about 99.9999%, about 99.99999%, about 99.999999%, about 99.9999999%, about 99.99999990%, about 99.999999999%, about 99.9999999999%, about 99.99999999999%, about 99.999999999990%, about 99.9999999999999% confidence, or above 99.9999999999999% confidence). For example, an unknown protein may match strongly with two protein candidates. The two protein candidates may have high sequence similarity to each other (e.g., two protein isoforms, such as proteins with single amino acid variants compared to a canonical sequence). In these cases, no individual protein candidate may be assigned with high confidence, but a high confidence may be ascribed to the unknown protein matching to a single, but unknown, member of the "protein group" comprising the two strongly matching protein candidates.

In some embodiments, efforts may be made to detect cases where unknown proteins are not optically-resolved. For example, on rare occasion, two or more proteins may bind in the same "well" or location of a substrate despite efforts to prevent this occurrence. In some cases, the conjugated proteins may be treated with a non-specific dye and the signal from the dye measured. In cases where two or more proteins are not optically-resolved, the signal resulting from the dye may be higher than locations containing a single protein and may be used to flag locations with multiple bound proteins.

In some embodiments, the plurality of candidate proteins is generated or modified by sequencing or analyzing the DNA or RNA of the human or organism from which the sample of unknown proteins is obtained or derived.

In some embodiments, the method further comprises deriving information on post-translational modifications of the unknown protein. The information on post-translational modifications may comprise the presence of a post-translational modification without knowledge of the nature of the specific modification. The database may be considered to be an exponential product of PTMs. For example, once a protein candidate sequence has been assigned to an unknown protein, the pattern of affinity reagent binding for the assayed protein may be compared to a database containing binding measurements for the affinity reagents to the same candidate from previous experiments. For example, a database of binding measurements may be derived from binding to a Nucleic Acid Programmable Protein Array (NAPPA) containing unmodified proteins of known sequence at known locations.

Additionally or alternatively, a database of binding measurements may be derived from previous experiments in which protein candidate sequences were confidently assigned to unknown proteins. Discrepancies in binding measurements between the assayed protein and the database of existing measurements may provide information on the likelihood of post-translation modification. For example, if an affinity agent has a high frequency of binding to the candidate protein in the database, but does not bind the assayed protein, there is a higher likelihood of a post-translational modification being present somewhere on the protein. If the binding epitope is known for the affinity reagent for which there is a binding discrepancy, the location of the post translational modification may be localized to at or near the binding epitope of the affinity reagent. In some embodiments, information on specific post-translational modifications may be derived by performing repeated affinity reagent measurements before and after treatment of the protein-substrate conjugate with an enzyme that specifically removes the particular post translational modification. For example, binding measurements may be acquired for a sequence of affinity reagents prior to treatment of the substrate with a phosphatase, and then repeated after treatment with a phosphatase. Affinity reagents which bind an unknown protein prior to phosphatase treatment but not after phosphatase treatment (differential binding) may provide evidence of phosphorylation. If the epitope recognized by the differentially binding affinity reagent is known, the phosphorylation may be localized to at or near the binding epitope for the affinity reagent.

In some cases, the count of a particular post-translational modification may be determined using binding measurements with an affinity reagent against a particular post-translational modification. For example, an antibody that recognizes phosphorylation events may be used as an affinity reagent. The binding of this reagent may indicate the presence of at least one phosphorylation on the unknown protein. In some cases, the number of discrete post-translational modifications of a particular type on an unknown protein may be determined by counting the number of binding events measured for an affinity reagent specific to the particular post-translational modification. For example, a phosphorylation specific antibody may be conjugated to a fluorescent reporter. In this case, the intensity of the fluorescent signal may be used to determine the number of phosphorylation-specific affinity reagents bound to an unknown protein. The number of phosphorylation-specific affinity reagents bound to the unknown protein may in turn be used to determine the number of phosphorylation sites on the unknown protein. In some embodiments, evidence from affinity reagent binding experiments may be combined with pre-existing knowledge of amino acid sequence motifs or specific protein locations likely to be post-translationally modified (e.g., from dbPTM, PhosphoSitePlus, or UniProt) to derive more accurate count, identification, or localization of post-translational modification. For example, if the location of a post-translational modification is not exactly determined from affinity measurements alone, a location containing an amino acid sequence motif frequently associated with the post translational modification of interest may be favored.

In some embodiments, the probabilities are iteratively generated until a predetermined condition is satisfied. In some embodiments, the predetermined condition comprises generating each of the plurality of probabilities with a confidence of at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.9%, at least 99.99%, at least 99.999%, at least 99.9999%, at least 99.99999%, at least 99.9999990%, at least 99.9999999%, at least 99.99999999%, at least 99.999999999%, at least 99.9999999990%, at least 99.99999999999%, at least 99.999999999999%, at least 99.99999999999990% confidence, or above 99.9999999999999% confidence.

In some embodiments, the method further comprises generating a paper or electronic report identifying one or more unknown proteins in the sample. The paper or electronic report may further indicate, for each of the candidate proteins, a confidence level for the candidate protein being present in the sample. The confidence level may comprise a probability value. Alternatively, the confidence level may comprise a probability value with an error. Alternatively, the confidence level may comprise a range of probability values, optionally with a confidence (e.g., about 90%, about 95%, about 96%, about 97%, about 98%, about 99%, about 99.9%, about 99.99%, about 99.999%, about 99.9999%, about 99.99999%, about 99.999999%, about 99.9999999%, about 99.99999999%, about 99.999999999%, about 99.9999999999%, about 99.99999999999%, about 99.999999999999%, about 99.9999999999999% confidence, or above 99.9999999999999% confidence). The paper or electronic report may further indicate the list of protein candidates identified below an expected false discovery rate threshold (e.g., a false discovery rate below 10%, 9%, 8%, 7% 6%, 5%, 4%, 3%, 2%, 1%, 0.5%, 0.4%, 0.3%, 0.2%, or 0.1%). The false discovery rate may be estimated by first sorting the protein identifications in descending order of confidence. The estimated false discovery rate at any point in the sorted list may then be calculated as 1−avg_c_prob, where avg_c_prob is the average candidate probability for all proteins at or before (e.g., higher confidence than) the current point in the list. A list of protein identifications below a desired false discovery rate threshold may then be generated by returning all protein identifications before the earliest point in the sorted list where the false discovery rate is higher than the threshold. Alternatively, a list of protein identifications below a desired false discovery rate threshold may be generated by returning all proteins before, and including, the latest point in the sorted list where the false discovery rate is below or equal to the desired threshold.

In some embodiments, the sample comprises a biological sample. The biological sample may be obtained from a subject. In some embodiments, the method further comprises identifying a disease state or a disorder in the subject based at least on the plurality of probabilities. In some embodiments, the method further comprises quantifying proteins by counting the number of identifications generated for each protein candidate. For example, the absolute quantity (e.g., number of protein molecules) of a protein present in the sample can be calculated by counting the number of confident identifications generated from that protein candidate. In some embodiments, the quantity may be calculated as a percentage of the total number of unknown proteins assayed. In some embodiments, the raw identification counts may be calibrated to remove systematic error from the instrument and detection systems. In some embodiments, the quantity may be calibrated to remove biases in quantity caused by variation in detectability of protein candidates. Protein detectability may be assessed from empirical measurements or computer simulation.

The disease or disorder may be an infectious disease, an immune disorder or disease, a cancer, a genetic disease, a degenerative disease, a lifestyle disease, an injury, a rare disease or an age related disease. The infectious disease may be caused by bacteria, viruses, fungi and/or parasites. Non-limiting examples of cancers include Bladder cancer, Lung cancer, Brain cancer, Melanoma, Breast cancer, Non-Hodgkin lymphoma, Cervical cancer, Ovarian cancer, Colorectal cancer, Pancreatic cancer, Esophageal cancer, Prostate cancer, Kidney cancer, Skin cancer, Leukemia, Thyroid cancer, Liver cancer, and Uterine cancer. Some examples of genetic diseases or disorders include, but are not limited to, multiple sclerosis (MS), cystic fibrosis, Charcot-Marie-Tooth disease, Huntington's disease, Peutz-Jeghers syndrome, Down syndrome, Rheumatoid arthritis, and Tay-Sachs disease. Non-limiting examples of lifestyle diseases include obesity, diabetes, arteriosclerosis, heart disease, stroke, hypertension, liver cirrhosis, nephritis, cancer, chronic obstructive pulmonary disease (copd), hearing problems, and chronic backache. Some examples of injuries include, but are not limited to, abrasion, brain injuries, bruising, burns, concussions, congestive heart failure, construction injuries, dislocation, flail chest, fracture, hemothorax, herniated disc, hip pointer, hypothermia, lacerations, pinched nerve, pneumothorax, rib fracture, sciatica, spinal cord injury, tendons ligaments fascia injury, traumatic brain injury, and whiplash.

In some embodiments, the method comprises identifying and quantifying small molecules (e.g. metabolites) or glycans instead of, or in addition to, proteins. For example, affinity reagents, such as lectins or antibodies which bind to sugars or combinations of sugars with varying propensity, may be used to identify glycans. The propensity of the affinity reagents to bind various sugars or combinations of sugars may be characterized by analyzing binding to a commercially-available glycan array. For example, unknown glycans may be conjugated to a functionalized substrate using hydroxyl-reactive chemistry and binding measurements may be acquired using the glycan-binding affinity reagents. The binding measurements of the affinity reagents to the unknown glycans on the substrate may be used directly to quantify the number of glycans with a particular sugar or combination of sugars. Alternatively, one or more binding measurements may be compared to predicted binding measurements from a database of candidate glycan structures using the methods described herein to identify the structure of each unknown glycan. In some embodiments, proteins are bound to the substrate and binding measurements with glycan affinity reagents are generated to identify glycans attached to the proteins. Further, binding measurements may be made with both glycan and protein affinity reagents to generate protein backbone sequence and conjugated glycan identifications in a single experiment. As another example, metabolites may be conjugated to a functionalized substrate using chemistry targeted toward coupling groups commonly found in metabolites such as sulfhydryl, carbonyl, amine, or active hydrogen. Binding measurements may be made using affinity reagents with different propensities to particular functional groups, structural motifs, or metabolites. The resulting binding measurements may be compared to predicted binding measurements for a database of candidate small molecules, and the methods described herein may be used to identify the metabolite at each location on the substrate.

Example 1: Protein Identification by Affinity Reagent Binding

The methods described herein may be used in combination with affinity binding reagents (e.g., aptamers or antibodies) binding measurements to analyze and/or identify proteins in a sample. In this case, the measurement outcome probability to be calculated is the probability of a binding or non-binding event of an affinity binding reagent (e.g., affinity reagent or affinity probe) to a protein candidate. A binding probability may be modeled as being conditional on the presence of an epitope which is recognized by the affinity binding reagent being present in the sequence of the protein. For example, an epitope may be a "trimer" (a sequence of three amino acids). An affinity reagent may be designed to target a particular epitope (e.g., GAV). Off-target binding of an affinity reagent (e.g., binding of an affinity reagent to an epitope different from its target epitope) may be modeled by including a non-zero probability of binding to additional epitopes.

For example, an affinity reagent may be designed to bind the GAV trimer, but may have off-target binding to three additional recognition sites: CLD, TYL, and IAD. For this affinity reagent, the binding probability can be modeled as:

$P$(affinity probe binding|protein)={0.25, if $GAV$, $CLD$, $TYL$, or $IAD$ is present in the protein sequence; 0, otherwise}.

There may also be a small probability of the affinity reagent binding non-specifically to a protein, which can be expressed as:

$P$(affinity probe binding|protein)={0.25, if $GAV$, $CLD$, $TYL$, or $IAD$ is present in the protein sequence; 0.00001, otherwise}.

Here, the probability measures the outcome of the detection of antibody binding.

As an example, consider a case where proteins from a human-derived sample are analyzed. The proteins in the sample are assumed to be represented in the human "reference" proteome (for example, as found in the Uniprot database of canonical protein sequence and functional information). That is, the protein candidate list is the set of about 21 thousand proteins and associated sequences in the UniProt database. A collection of unknown proteins are derived from the sample, and each unknown protein is probed in a series of affinity reagent binding experiments with the outcome (binding or no binding) measured and recorded. For example, such experiments may comprise sequentially adding different affinity reagents and observing the binding of the affinity reagents to the unknown proteins. The affinity reagents, or "probes," are selected to target the most frequently observed trimers (out of about 800 possible trimers) in the protein candidate list. Outside of the targeted trimer, each probe has off-target binding to a number of additional trimers which are selected at random. The probability of a probe binding to a protein sequence can be expressed as:

$P$(affinity probe binding|protein)=1−[$P$(no non-specific binding)*$P$(no specific binding)].

Assuming that:
n=sequence length of a protein candidate; q=length of a recognition site (e.g., 3); s=non-specific trimer binding probability (e.g., $10^{-5}$); p=specific binding probability (e.g., 0.25); the terms P(no non-specific binding) and P(no specific binding) can be expressed as:

$$P(\text{no non-specific binding}) = (1-s)^{n-q+1} = (1-10^{-5})^{n-3+1}$$

and $P(\text{no specific binding}) = \Pi_{\text{for each recognition site}} (1-p)^{\text{number of site occurrences in protein}}$.

Finally, the probability of a probe not binding to a protein can be expressed as:

$P$(affinity probe not binding|protein)=1−$P$(affinity probe binding|protein).

Figure 2:
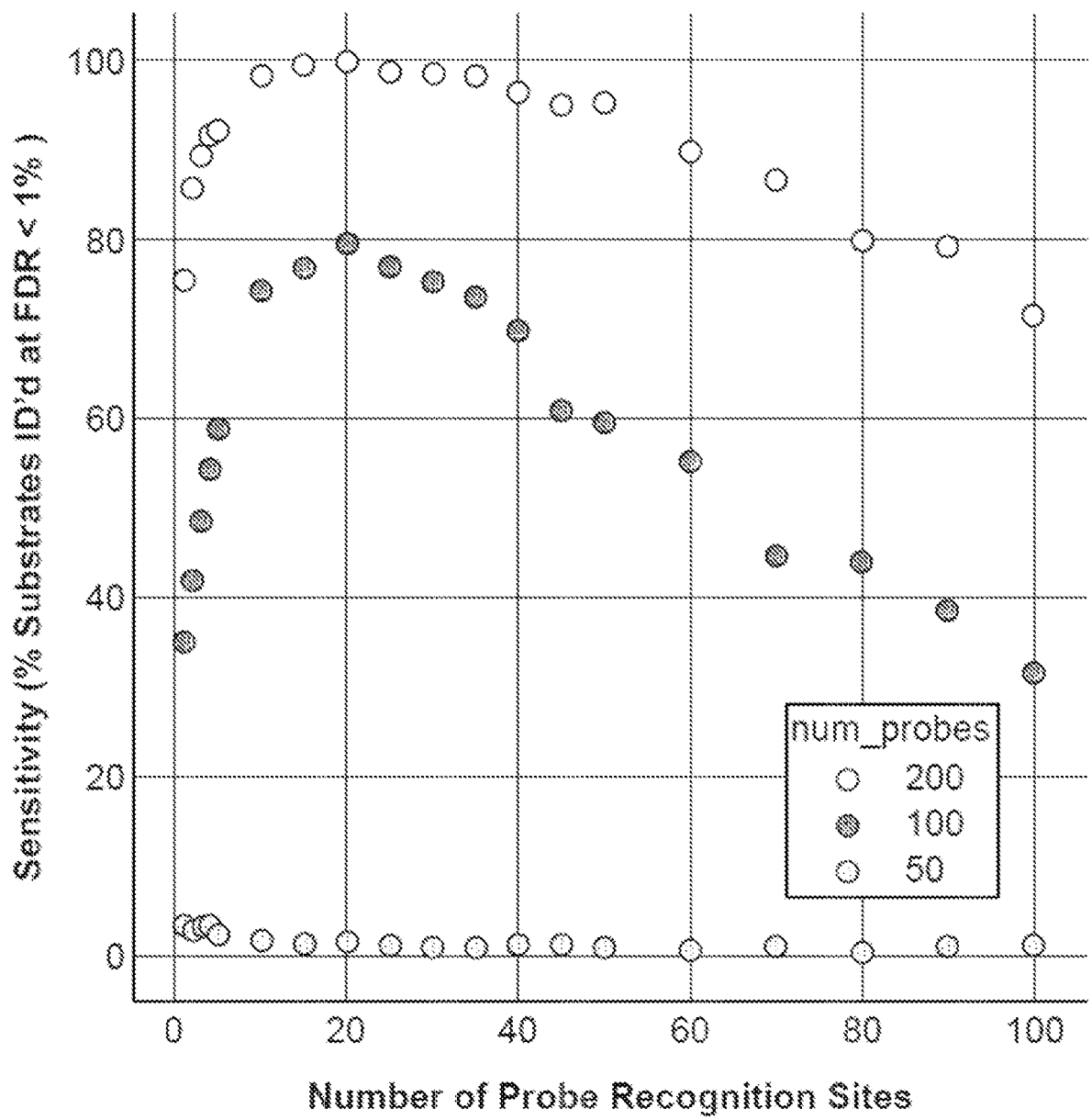
FIG. 2 illustrates the sensitivity of affinity reagent probes (e.g., the percent of substrates identified with a false detection rate (FDR) of less than 1%) plotted against the number of probe recognition sites (e.g., trimer-binding epitopes) in the affinity reagent probe (ranging up to 100 probe recognition sites or trimer-binding epitopes), for three different experimental cases (with 50, 100, and 200 probes used, as denoted by the gray, black, and white circles, respectively), in accordance with disclosed embodiments.

FIG. 2 illustrates the sensitivity of affinity reagent probes (e.g., the percent of substrates identified with a false detection rate (FDR) of less than 1%) plotted against the number of probe recognition sites (e.g., trimer-binding epitopes) in the affinity reagent probe (ranging up to 100 probe recognition sites or trimer-binding epitopes), for three different experimental cases (with 50, 100, and 200 probes used, as denoted by the gray, black, and white circles, respectively). As seen in FIG. 2, the number of probes used has a significant effect on the ability to correctly identify proteins. Plotted on the y-axis is the sensitivity, which is the percentage of the unknown proteins that are correctly identified with a threshold (e.g., upper limit) of less than 1% of the identifications being incorrect. For example, if each probe contains 5 recognition sites or trimer-binding epitopes (1 targeted site and 4 off-target sites), the sensitivity of protein identification is less than 10% when 50 probes are used, about 60% when 100 probes are used, and about 90% when 200 probes are used. In fact, when 300 probes are used, the sensitivity exceeds 95% (result not shown on plot). This protein identification approach supports probes with many off-target binding sites. Even with 60 recognition sites or trimer-binding epitopes (1 targeted site and 59 off-target sites), identification sensitivity is about 55% in a 100-probe experiment and about 90% in a 200-probe experiment.

Figure 3:
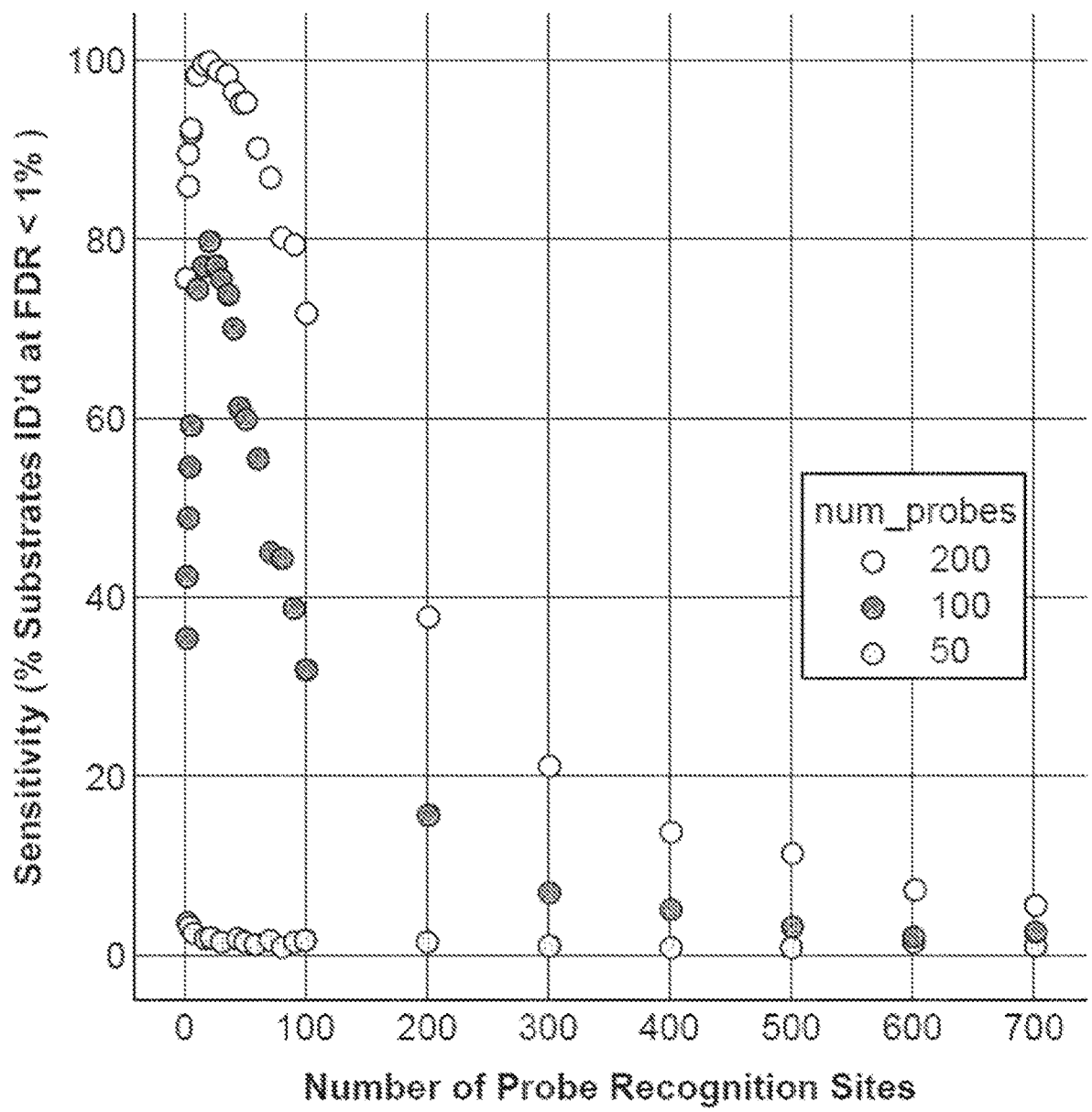
FIG. 3 illustrates the sensitivity of affinity reagent probes (e.g., the percent of substrates identified with a false detection rate (FDR) of less than 1%) plotted against the number of probe recognition sites (e.g., trimer-binding epitopes) in the affinity reagent probe (ranging up to 700 probe recognition sites or trimer-binding epitopes) for three different experimental cases (with 50, 100, and 200 probes used, as denoted by the gray, black, and white circles, respectively), in accordance with disclosed embodiments.

However, as seen in FIG. 3, the ability to identify proteins degrades rapidly when probes have more than 100 binding sites or trimer-binding epitopes. FIG. 3 illustrates the sensitivity of affinity reagent probes (e.g., the percent of substrates identified with a false detection rate (FDR) of less than 1%) plotted against the number of probe recognition sites (e.g., trimer-binding epitopes) in the affinity reagent probe (ranging up to 700 probe recognition sites or trimer-binding epitopes) for three different experimental cases (with 50, 100, and 200 probes used, as denoted by the gray, black, and white circles, respectively). For example, if each probe contains 100 recognition sites or trimer-binding epitopes (1 targeted site, 99 off-target sites), the sensitivity of protein identification is about 1% when 50 probes are used, about 30% when 100 probes are used, and about 70% when 200 probes are used. However, if each probe contains 200 recognition sites or trimer-binding epitopes (1 targeted site, 199 off-target sites), the sensitivity of protein identification is less than 1% when 50 probes are used, less than 20% when 100 probes are used, and less than 40% when 200 probes are used.

Figure 4:
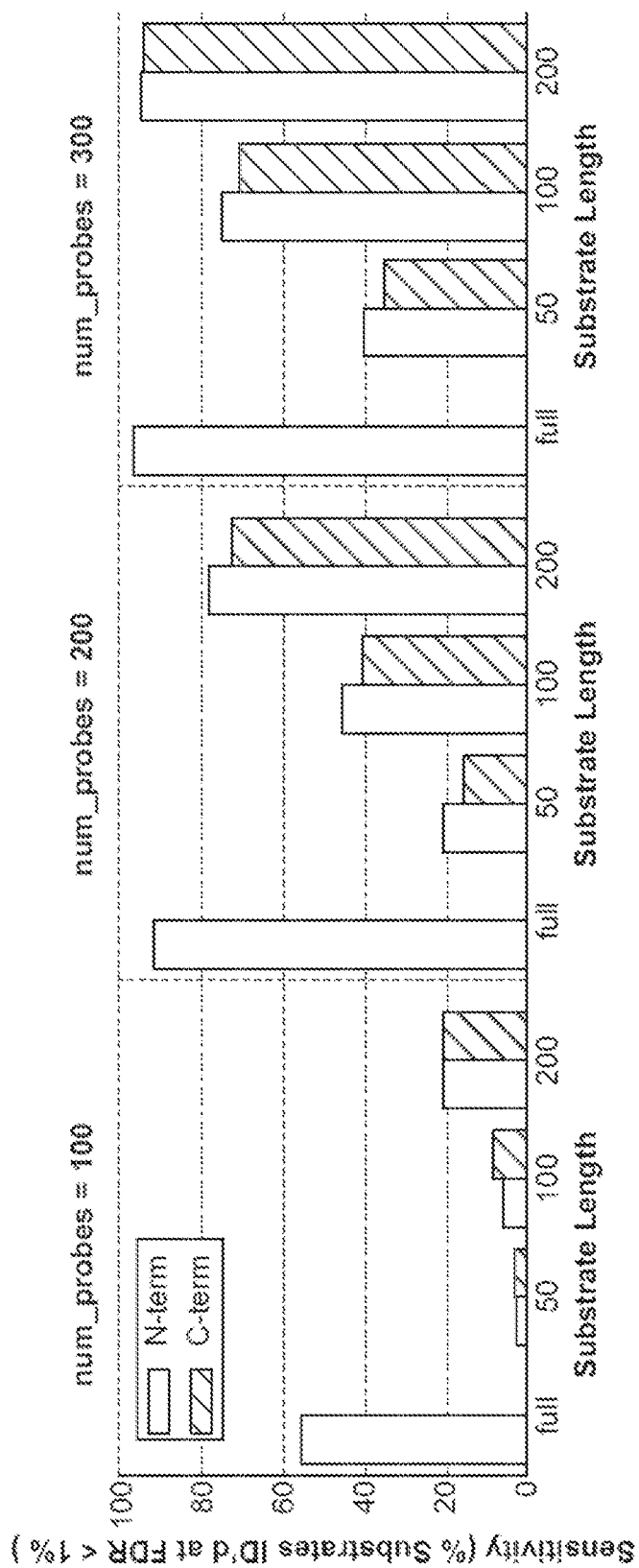
FIG. 4 illustrates plots showing the sensitivity of protein identification with experiments using 100 (left), 200 (center), or 300 probes (right), in accordance with disclosed embodiments.

Example 2: Protein Affinity Reagent Binding to Proteins that have been Truncated or Degraded The methods described herein may be applied to analyze and/or identify proteins in a sample that have been truncated. In such experiments, probability calculation of an affinity probe binding to a protein is modified to only consider binding to the truncated protein sequence, rather than the full protein sequence. For example, FIG. 4 illustrates plots showing the sensitivity of protein identification with experiments using 100 (left), 200 (center), or 300 probes (right). In each plot, sensitivity of affinity reagent probes (e.g., the percent of substrates identified with a false detection rate (FDR) of less than 1%) is determined for an experiment in which 4 substrates lengths are measured: (1) the intact (full) protein, (2) the 50-length N- or C-terminal fragment of the protein, (3) the 100-length N- or C-terminal fragment of the protein, and (4) the 200-length N- or C-terminal fragment of the protein. N- and C-terminal fragments are denoted with solid and striped bars, respectively. Each probe binds to the targeted trimer and 4 other random off-target trimers. As shown in FIG. 4, a substantial proportion of proteins (~40%) may be identified, for example, even when proteins are truncated to fragments containing only 100 amino acids and 200-probe experiments are performed.

If 300 probes are used, then about 70-75% of proteins may be identified in the case when proteins are truncated to fragments containing only 100 amino acids. FIG. 4 also shows that truncated proteins containing the N-terminal fragment are slightly easier to identify (e.g., with higher sensitivity of protein identification) than fragments containing the C-terminal fragment.

Figure 5:
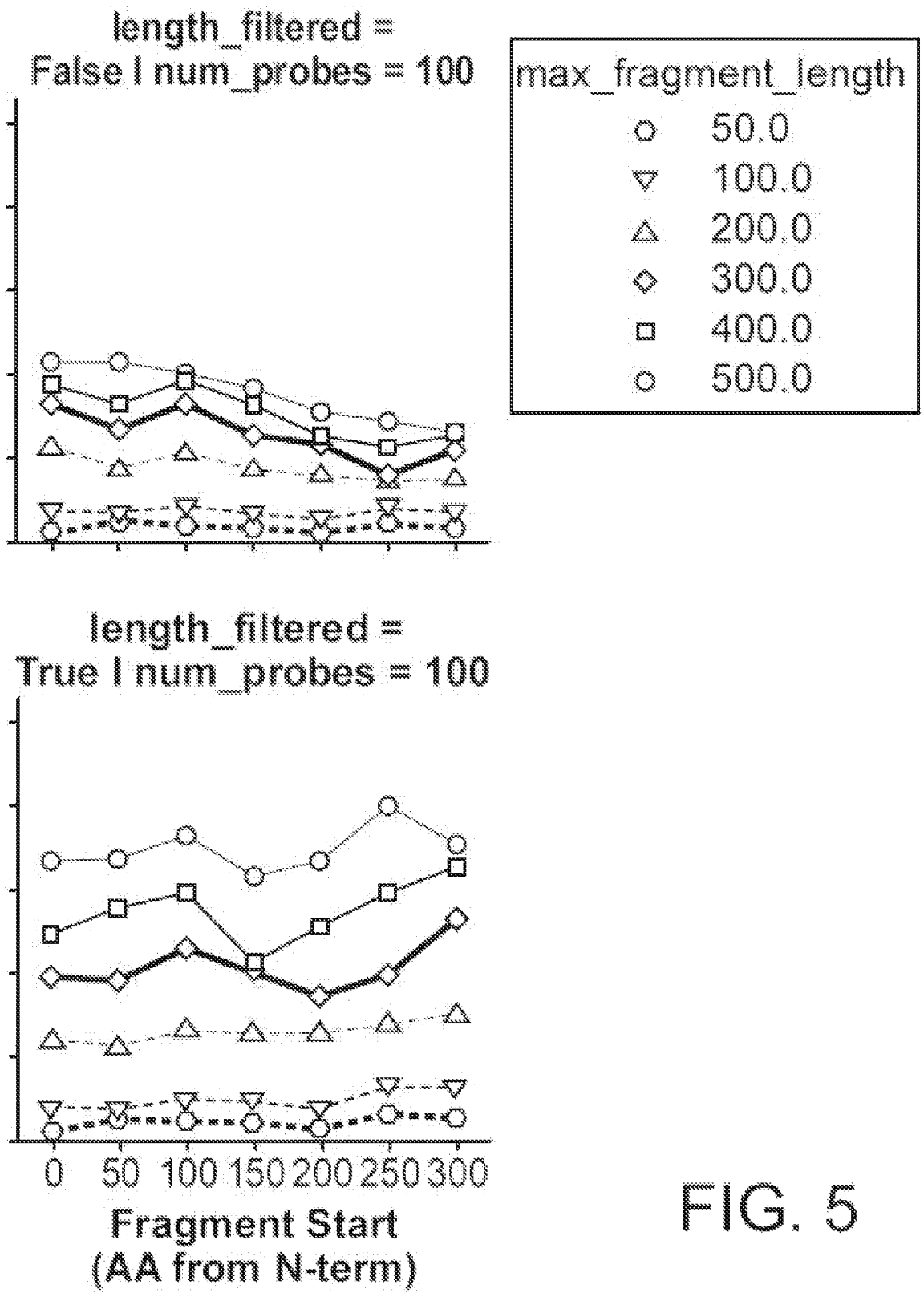
FIG. 5 illustrates plots showing the sensitivity of protein identification with experiments using various protein fragmentation approaches. In each of the top row and the bottom row, protein identification performance is shown with 50, 100, 200, and 300 affinity reagent measurements (in the 4 panels from left to right), with maximum fragment length values of 50, 100, 200, 300, 400, and 500 (as denoted by the hexagons, down-pointing triangles, up-pointing triangles, diamonds, rectangles, and circles, respectively), in accordance with disclosed embodiments.
Figure 5:
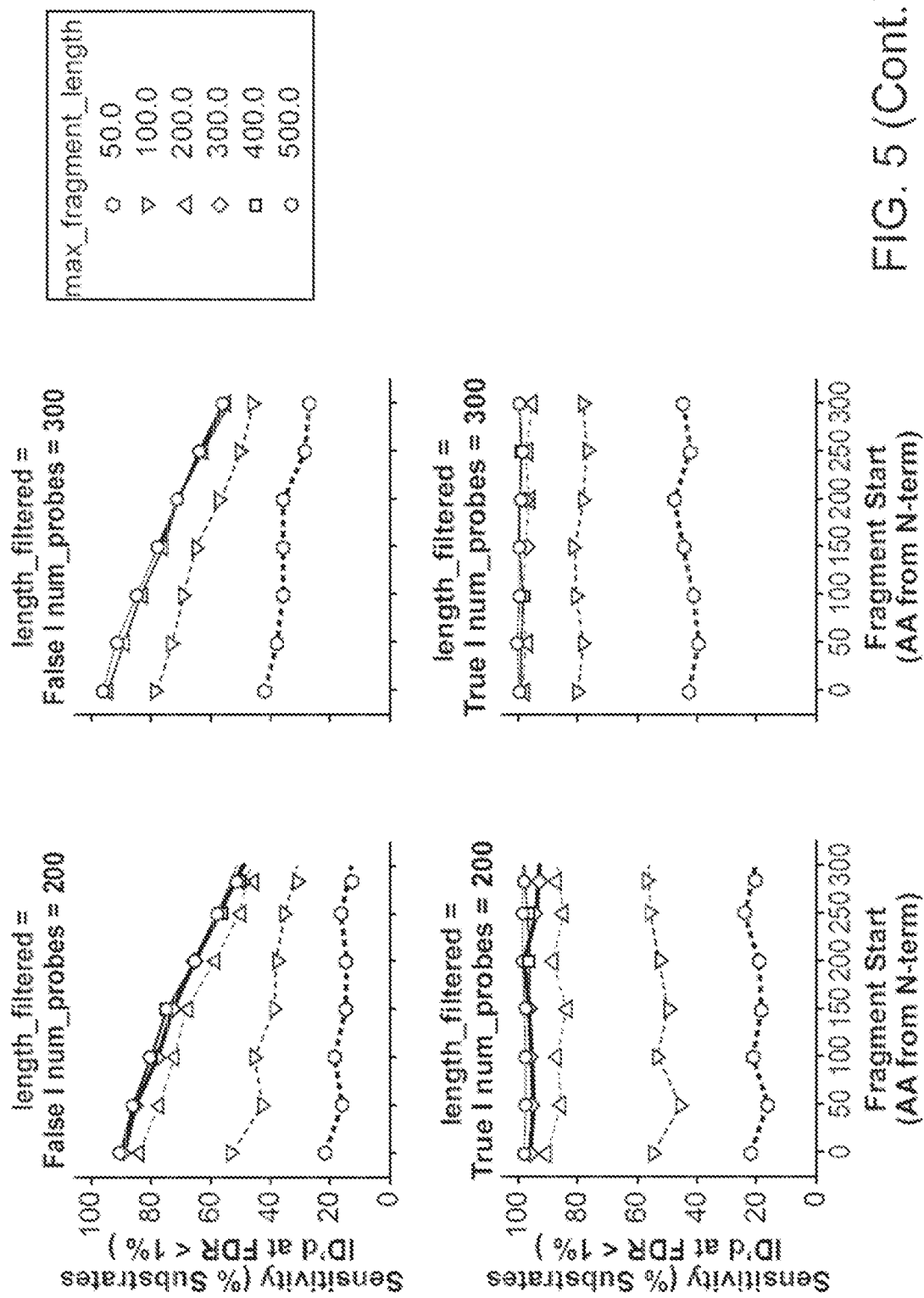

Example 3: Protein Fragments Containing Neither the C-Terminus Nor the N-Terminus of the Intact Protein from which they are Derived The methods described herein may be applied to analyze and/or identify protein fragments in a sample that contain neither of the original 2 termini of the intact protein from which the fragment is derived. The probability calculation of an affinity probe binding to a protein in such an experiment is modified to only consider binding to the truncated rather than the full protein sequence. FIG. 5 illustrates plots showing the sensitivity of protein identification with experiments using various protein fragmentation approaches. In each of the top row and the bottom row, protein identification performance is shown with 50, 100, 200, and 300 affinity reagent measurements (in the 4 panels from left to right), with maximum fragment length values of 50, 100, 200, 300, 400, and 500 (as denoted by the hexagons, down-pointing triangles, up-pointing triangles, diamonds, rectangles, and circles, respectively).

Referring to the top row of FIG. 5, each point on each subplot represents sensitivity (protein identification rate) when using a particular fragment generation approach defined by the fragment start location and fragment length. Fragments are generated at a specific starting location on each protein indexed by distance (e.g., number of amino acids (AA) away) from the N-terminus in amino acids (as plotted on the x-axis). The end of each protein fragment is selected to generate a fragment with length 50, 100, 200, 300, 400, or 500 amino acids (maximum fragment length, or max_fragment_length values), as denoted by the hexagons, down-pointing triangles, up-pointing triangles, diamonds, rectangles, and circles, respectively. If a fragment of a given designated length cannot be generated because the protein is too short, the fragment shorter than the requested length containing the C-terminus is retained. For example, when an experiment is performed with 50 affinity reagents, only a small percentage of proteins may be identified (as plotted on the y-axis). However, when an experiment is performed with 200 affinity reagent probes using fragments with a maximum length of 200 amino acids, about 50% to about 85% of proteins may be identified (as plotted on the y-axis) depending on the fragment start site (as plotted on the x-axis). There is a general trend of decrease in protein identification sensitivity as the fragment start site moves further away from the N-terminus. This trend can be explained by the fact that, as the fragment start moves farther from the N-terminus, more fragments are generated that include the C-terminus and are less than the maximum fragment length.

Referring to the bottom row of FIG. 5, the 4 subplots here show similar results as those in the top row, except that any fragments which do not match the maximum fragment length (e.g., fragments not containing the C-terminus) are discarded from analysis prior to the sensitivity and false discovery rate calculation. The sensitivity of protein identification is calculated only among those proteins that may have generated a valid fragment. As the bottom row of FIG. 5 shows, without the fragment length fixed, at the maximum fragment length, there is no statistically significant variation in protein identification sensitivity with respect to the location of the fragment start site. Fragment length is the major determinant of protein identification rate rather than the fragment location within the protein sequence.

Example 4: Protein Identification by Measurement of Length, Hydrophobicity, and/or Isoelectric Point The methods described herein may be applied to analyze and/or identify proteins in a sample using information from measurements on the proteins, including length, hydrophobicity, and/or isoelectric point (pI). The probability of measuring a particular length for a protein query candidate can be expressed by:

$$P(\text{measurement outcome} \mid \text{protein}) = \frac{1}{\sigma\sqrt{2\pi}} \exp\left(-\frac{u^2}{2}\right) \text{ where}$$

$\sigma = |CV^* \text{expected outcome value}|$ $u = (\text{measured outcome value} - \text{expected outcome value})/\sigma$ In this case, the measurement outcome is the measured length of the unknown protein, and the expected outcome value is the length of the protein query candidate. The model also uses a coefficient of variation (CV) value which describes the expected precision of the measurement approach. The probability of measuring a particular hydrophobicity for a protein is calculated using the same formula, with the expected outcome value being set to a grand average of hydropathy (gravy) score calculated from the protein candidate sequence. Such a gravy score can be calculated, for example, using a Biopython tool for computational molecular biology to perform a Kyte-Doolittle computational method (e.g., as described in [Kyte et al., "A simple method for displaying the hydropathic character of a protein," *J. Mol. Biol.*, 1982 May 5; 157(1):105-32], which is incorporated herein by reference in its entirety). Similarly, isoelectric point (pI) is modeled with an expected pI value calculated from the protein candidate sequence using Biopython to implement the methods of Bjellqvist (e.g., as described in [Audain et al., "Accurate estimation ofisoelectric point of protein and peptide based on amino acid sequences," *Bioinformatics*, 2015 Nov. 14; 32(6):821-27], which is incorporated herein by reference in its entirety), according to the methods described in [Tabb, David L., "An algorithm for isoelectric point estimation," <http://fields.s- cripps.edu/DTASelect/20010710-pI-Algorithm.pdf>, 2003 Jun. 28], which is incorporated herein by reference in its entirety. In all cases, the experimental measurement precision was set to a CV value of 0.1.

Figure 6:
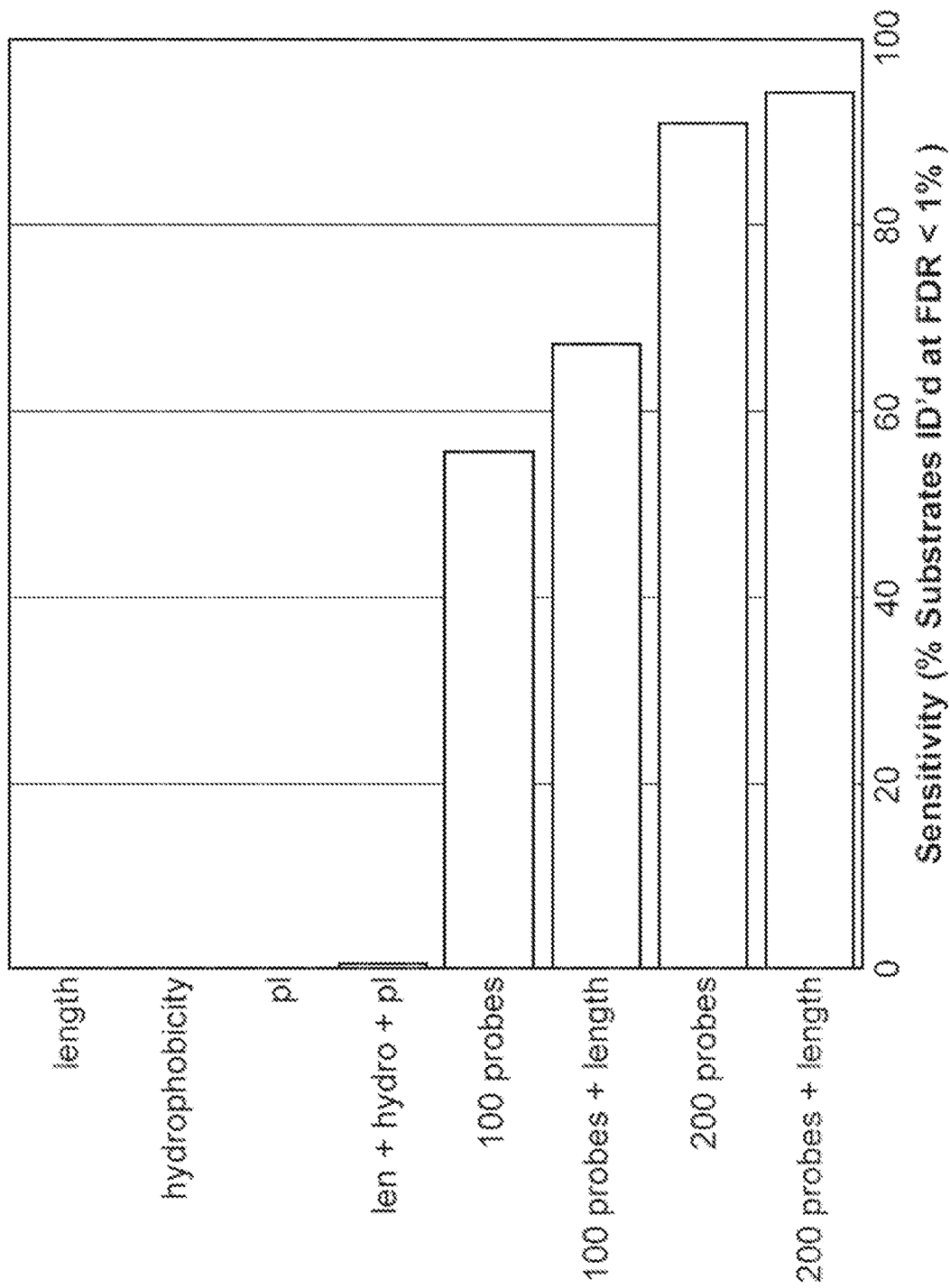
FIG. 6 illustrates plots showing the sensitivity of identification of human proteins (percent of substrates identified at an FDR of less than 1%) with experiments using various combinations of types of measurements), in accordance with disclosed embodiments.

FIG. 6 illustrates plots showing the sensitivity of identification of human proteins (percent of substrates identified at an FDR of less than 1%) with experiments using various combinations of types of measurements. Using protein length, hydrophobicity, or pI measurements alone, virtually no proteins can be identified (e.g., a sensitivity <1%). Combining all three types of measurements (len+hydro+pI) still yields virtually no identifications. However, protein length, hydrophobicity, or pI measurements may be used to augment measurements from affinity reagent probe binding experiments. For example, proteins may be fractionated based on any of these characteristics, and each fraction conjugated to a different spatial location on the substrate. Following this fractionation and conjugation, affinity reagent binding measurements may be made, and the measurement of hydrophobicity, protein length, or pI may be determined by the spatial address of the protein. Denatured proteins may be fractionated by molecular weight based on gel filtration (SDS-PAGE) or size exclusion chromatography. The length of proteins may be estimated from the molecular weight by dividing the weight by the average mass of an amino acid (111 Da). Proteins may be fractionated by hydrophobicity using hydrophobic interaction chromatography. Proteins may be fractionated by pI using ion exchange chromatography. For example, performing additional measurements of protein length by fractionation with a CV value of 0.1 improved sensitivity of identification using 100-probe (1 targeted trimer, and 4 additional off-target sites per probe) experiments from ~55% (without protein length measurements) to ~65% (with protein length measurements). Similarly, performing additional measurements of protein length with a CV value of 0.1 improved sensitivity of identification using 200-probe (1 targeted trimer, and 4 additional off-target sites per probe) experiments from ~90% (without protein length measurements) to ~95% (with protein length measurements).

Example 5: Protein Identification by Measurement with Mixtures of Antibodies

The methods described herein may be applied to analyze and/or identify proteins in a sample using information from experiments in which mixtures of affinity reagents are measured in each binding experiment. Consistent with disclosed embodiments, the identification of 1,000 unknown human proteins was benchmarked by acquiring binding measurements using pools of commercially-available antibodies from Santa Cruz Biotechnology, Inc. The 1,000 proteins were randomly selected from the Uniprot protein database, which comprises about 21,005 proteins. A list of monoclonal antibodies available from the Santa Cruz Biotechnology catalog with reactivity against human proteins was downloaded from an online antibody registry. The list contained 22,301 antibodies and was filtered to a list of 14,566 antibodies which matched to proteins in the Uniprot human protein database. The complete collection of antibodies modeled in the experiment comprised these 14,566 antibodies. Experimental assessment of binding of antibody mixtures to the 1,000 unknown protein candidates was performed as described below.

First, 50 mixtures of antibodies were modeled. To produce any single mixture, 5,000 antibodies from the total collection of antibodies were selected at random.

Next, for each mixture, a binding probability was determined for the mixture to any of the unknown proteins. Note that, although the proteins are "unknown" in the sense that the goal is to infer their identity, the algorithm is aware of the true identity of each "unknown protein." If the mixture contains an antibody against the unknown protein, a binding probability of 0.99 was assigned. If the mixture does not contain an antibody against the unknown protein, a binding probability of 0.0488 was assigned. In other words, the probability of a binding outcome for the mixture of antibodies was modeled as:

P(binding outcome|protein)={0.99, if mixture contains an antibody to the protein; 0.0488, otherwise}. The value of 0.0488 represents the probability of a non-specific (off-target) binding event occurring for this mixture against the protein. The non-specific binding probability for a mixture was modeled based on the expected probability of any individual antibody binding a protein other than its target, and the number of proteins in the mixture. The probability of a non-specific binding event for the mixture of antibodies is the probability of any single antibody in the mixture binding non-specifically. This probability is calculated based on the number of antibodies in the mixture (n), and the probability of non-specific binding (p) for any single antibody, and can be expressed by the equation:

Mixture non-specific binding probability=$1-(1-p)^n$

In this case, it was assumed that there is a probability of 0.00001 ($10^{-5}$) of a non-specific binding event where an individual antibody binding something other than its target protein. Therefore, the non-specific binding probability (p) for any single antibody is $10^{-5}$, giving: Mixture non-specific binding probability=$1-(1-10^{-5})^{5000}$=0.0488.

In addition, the probability of a non-binding outcome to a protein was calculated as:

P(non-binding outcome|protein)=1-P(binding outcome|protein).

For each unknown protein, binding was assessed for each antibody mixture measured based on the binding probability of the mixture to the unknown protein. The uniform distribution, with a minimum of 0 and a maximum of 1, was randomly sampled, and if the resulting number is less than the binding probability of the antibody mixture to the unknown protein, the experiment resulted in a binding event for that mixture. Otherwise, the experiment resulted in a non-binding event for that mixture. With all binding events assessed, protein inference is performed as follows:

For each unknown protein, the sequence of assessed binding events (50 total, 1 per mixture) was evaluated against each of the 21,005 protein candidates in the Uniprot database. More specifically, a probability of observing the sequence of binding events was calculated for each candidate. The probability was calculated by multiplying the probability of each individual mixture binding/non-binding event across all 50 mixtures measured. The binding probability was calculated in the same manner as described above, and the probability of non-binding is one minus the binding probability. The protein query candidate with the highest binding probability is the inferred identity for the unknown protein. A probability of the identification being correct for that individual protein was calculated as the probability of the top individual candidate divided by the summed probabilities of all candidates.

With the identity inferred for each of the 1,000 unknown proteins, the unknown proteins were sorted in descending order of their identification probability. An identification probability cutoff was selected such that the percentage of incorrect identifications among all identifications prior in the list was 1%. Overall, 551 of the 1,000 unknown proteins were identified with a 1% incorrect identification rate. Therefore, protein identification was performed with a sensitivity of 55.1%.

Example 6: Protein Identification in Many Species

The methods described herein may be applied to analyze and/or identify proteins in a sample obtained from many different species. For example, results from sequence of affinity reagent binding experiments may be used to identify proteins in *E. coli*, *Saccharomyces cerevisiae* (yeast), or *Homo sapiens* (humans), as denoted by the circles, triangles, and squares, respectively. To adapt analytical methods for each species, the protein candidate list must be generated from a species-specific sequence database, such as a reference proteome for the species downloaded from Uniprot.

Figure 7:
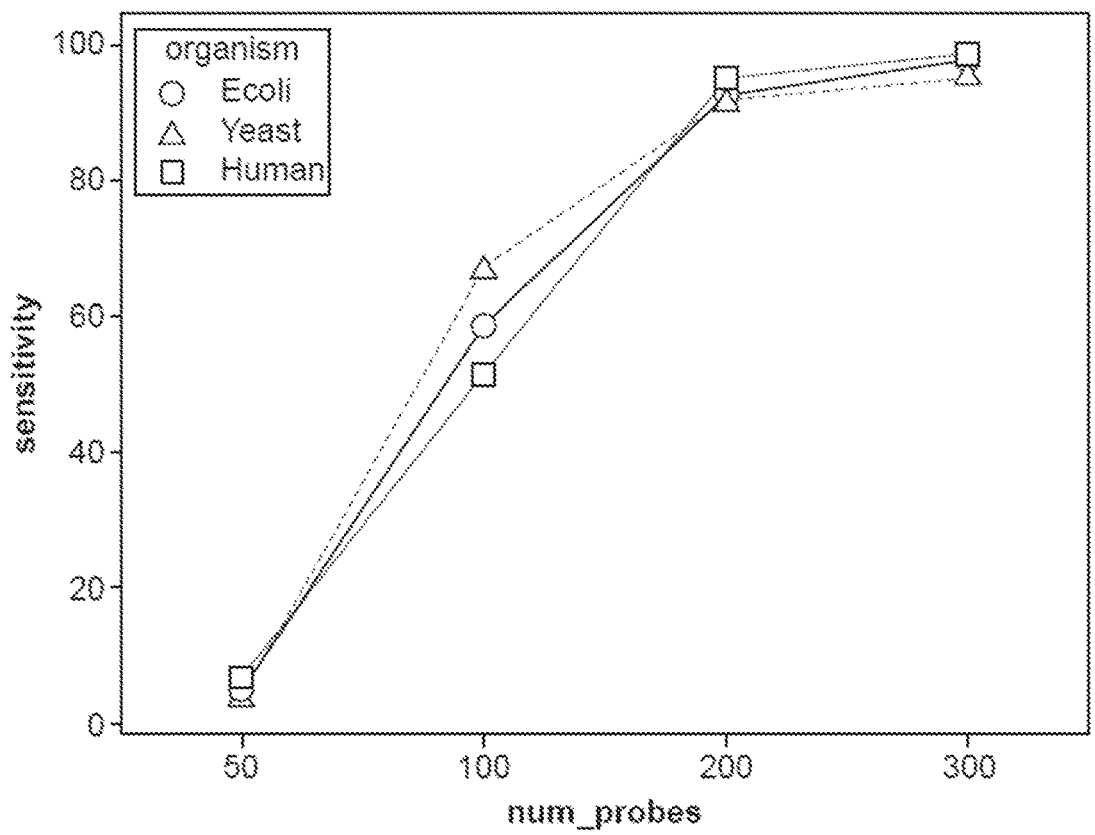
FIG. 7 illustrates plots showing the sensitivity of protein identification with experiments using 50, 100, 200, or 300 affinity reagent probe passes against unknown proteins from either *E. coli*, yeast, or human (as denoted by the circles, triangles, and squares, respectively), in accordance with disclosed embodiments.

FIG. 7 illustrates plots showing the sensitivity of protein identification with experiments using 50, 100, 200, or 300 affinity reagent probe passes against unknown proteins from either *E. coli*, yeast, or human (as denoted by the circles, triangles, and squares, respectively). Each probe binds to a targeted trimer, and 4 additional off-target sites with probability of 0.25. The sensitivity (percentage of unknown proteins identified at a false identification rate of less than 1%) for an experiment using 200 probes was about 90% for each of the three species tested.

Example 7: Protein Identification in the Presence of SNPs

The methods described herein may be applied to analyze and/or identify proteins in a sample in the presence of single amino acid variants (SAVs) caused by non-synonymous single-nucleotide polymorphisms (SNPs). Proteins that have the same sequence except for a handful of single amino acid variants (SAVs) may be difficult to distinguish. For example, in an experiment using a series of affinity reagent measurements, the canonical form of a protein may be nearly impossible to distinguish from its variant form, unless an affinity reagent which is highly-selective for the polymorphic region of the protein is included in the experiment. In cases where the polymorphic region is not distinguished by any of the affinity reagent measurements, measurements of either protein form will return similar probabilities (likelihoods) for both the canonical and variant protein query candidate (e.g., L (canonical protein|evidence)=0.8 and L (variant protein|evidence)=0.8).

In such a case, neither individual protein candidate may return a probability higher than 0.5, e.g., as expressed for the canonical protein below (where cprot=canonical protein, vprot=variant protein).

$$Pr(cprot \mid evidence) =$$

$$\frac{L(cprot \mid evidence)}{L(cprot \mid evidence) + L(vprot \mid evidence) + L_{other}} = \frac{0.8}{1.6 + L_{other}} \leq 0.5$$

where $L_{other}$ is the summed likelihood of all protein query candidates except the canonical protein and the variant protein and is a number greater than or equal to zero.

In this case, groups of potential protein identifications may be returned for an unknown protein. For example, the probability for the top two most likely protein query candidates may be expressed as:

$$Pr(cprot \text{ or } vprot \mid evidence) =$$

$$\frac{L(cprot \mid evidence) + L(vprot \mid evidence)}{L(cprot \mid evidence) + L(v \mid evidence) + L_{other}} = \frac{1.6}{1.6 + L_{other}}$$

Using this approach, a confident identification may be derived from the unknown protein, albeit one that does not resolve the canonical protein and the variant protein. In particular, cases where $L_{other}$ is near zero may be likely to result in a confident identification.

Example 8: Iterative Improvement of Probability Model from Empirical Results

A probabilistic model used in one or more methods described herein may be improved iteratively using empirical measurements during the computation of protein identifications using expectation maximization or related approaches. One such approach is described here for an affinity reagent binding experiment.

First, the binding probabilities for each affinity reagent probe are initialized with an estimate. For example, a collection of 200 probes may each target a single trimer and have an estimated binding probability of 0.5. Proteins are identified using the approaches disclosed elsewhere herein (for example, see Example 1). Next, the binding probabilities for each probe are refined iteratively based on empirical measurements, as summarized by the steps below:

(1) Use the collection of unknown proteins identified with estimated false discovery rate <0.01 to update binding probabilities:

For each probe, calculate the updated binding probability using the proportion of proteins in the collection that contain a binding site (trimer) recognized by the probe:

$$\text{updated probability} = \frac{\text{\# of proteins in collection with binding site that are bound by the probe}}{\text{\# of proteins in collection with binding site}}$$

Update the probe probability of "# of proteins in collection with binding site >20".

If the updated probability is $<10^{-5}$, set it to $10^{-5}$ (to avoid a probability of 0 being assigned).

(2) Perform another protein identification using the updated binding probabilities.

Repeat steps 1 and 2 for multiple iterations (e.g., for a total of 1, 2, 3, 4, 5, 6, 7, 8, 9, 10, or more than 10 iterations).

This iterative approach was tested using an experiment with 200 probes, each recognizing a single trimer with binding probability of 0.25. The 200 probe binding measurements were modeled against 2000 unknown proteins with the initial estimate for the probe binding probability set to 0.5. After performing 5 iterations of this iterative algorithm, the updated probe binding probabilities became more accurate (closer to 0.25) and the protein identification sensitivity increased.

Figure 8:
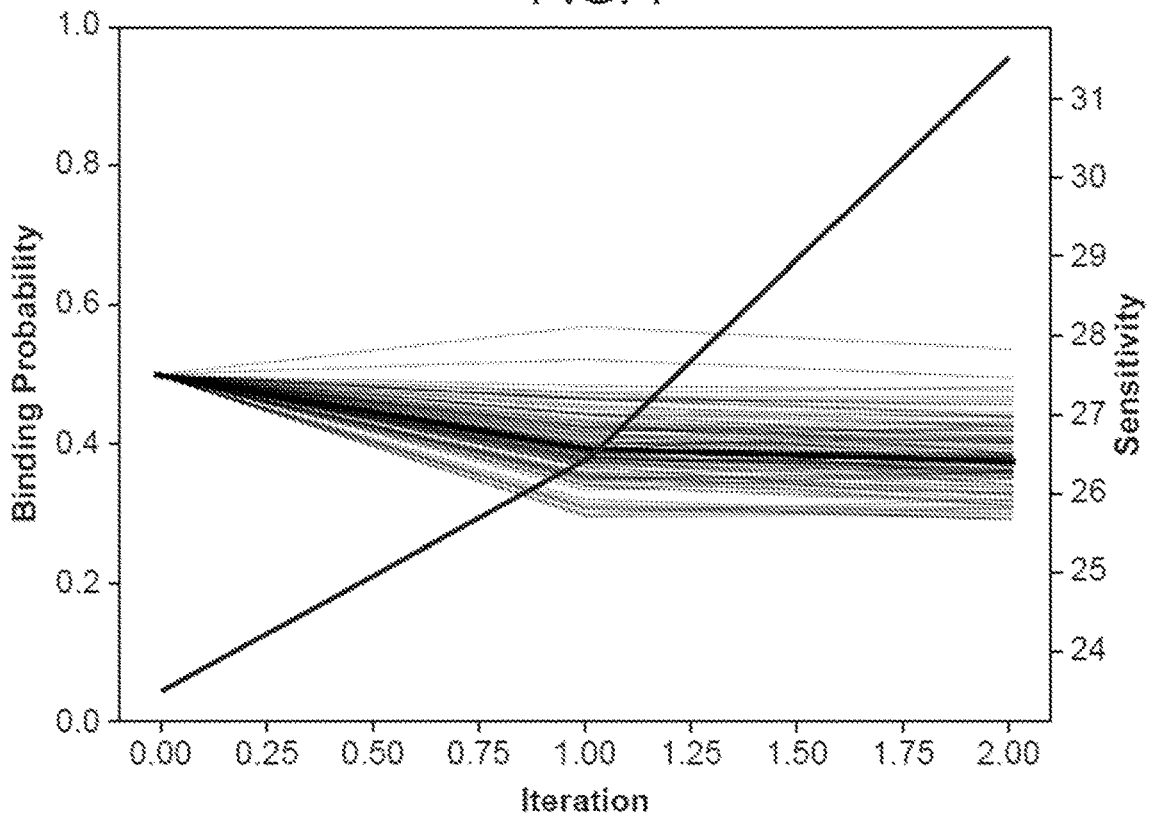
FIG. 8 illustrates a plot showing the binding probability (y-axis, left) and sensitivity of protein identification (y-axis, right) against iteration (x-axis), in accordance with disclosed embodiments.

FIG. 8 illustrates a plot showing the binding probability (y-axis, left) and sensitivity of protein identification (y-axis, right) against iteration (x-axis). As shown in FIG. 8, thin lines show the probe binding probabilities for each individual probe, the dark line among the thin lines is the median probe binding probability, and the thick line shows the protein identification sensitivity at each iteration.

Example 9: Estimating Identification False Discovery Rate from Protein Candidate Match Probabilities A probabilistic model for protein inference or identification used in one or more methods described herein yields as direct results a list of protein sequence matches for each unknown protein and an associated probability of that sequence match being correct. In many cases, only a subset of the protein identifications may be correct. Therefore, a method useful for estimating and controlling the false identification rate for a set of proteins is described below.

First, the complete set of protein identifications is sorted in descending order by the protein identification probability, as given below (where prot=protein):
prot1 probability ($p_1$): 0.99
prot2 probability ($p_2$): 0.97
prot3 probability ($p_3$): 0.92
prot4 probability ($p_4$): 0.9
prot5 probability ($p_5$): 0.8
prot6 probability ($p_6$): 0.75
prot7 probability ($p_7$): 0.6
prot8 probability ($p_8$): 0.5

Next, the expected false discovery rate at each point in the list is calculated as $1-\bar{p}$ where $\bar{p}$ is the average of all probabilities at the given point and earlier in the list (as given below):

| Protein | Probability | Estimated False ID Rate |
|---|---|---|
| prot1 | 0.990 | 0.010 |
| prot2 | 0.970 | 0.020 |
| prot3 | 0.920 | 0.040 |
| prot4 | 0.900 | 0.055 |
| prot5 | 0.800 | 0.084 |
| prot6 | 0.750 | 0.112 |
| prot7 | 0.600 | 0.153 |
| prot8 | 0.500 | 0.196 |

Figure 9:
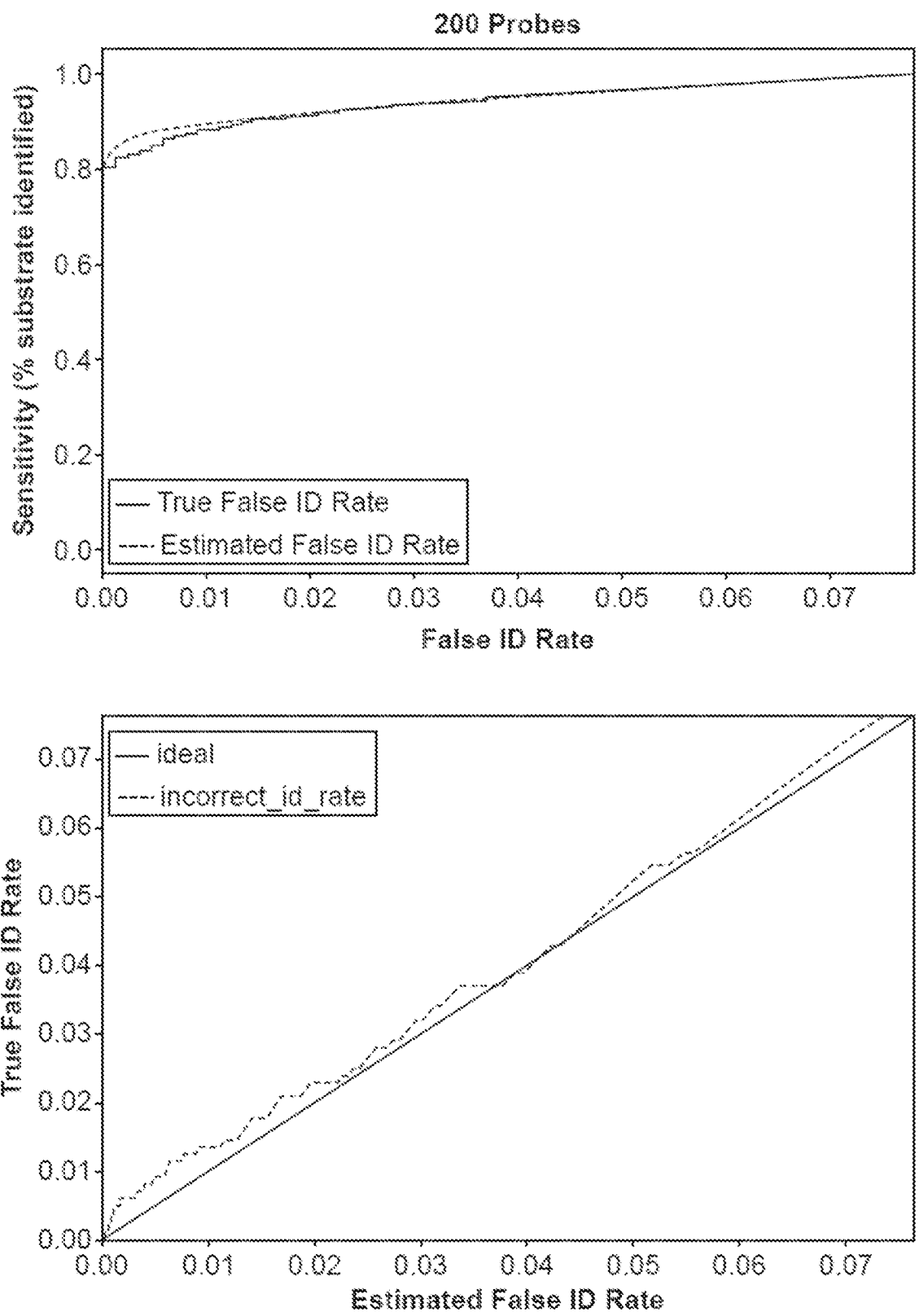
FIG. 9 shows a comparison of the estimated false identification rate to the true false identification rate for a simulated 200-probe experiment demonstrates accurate false identification rate estimation, in accordance with disclosed embodiments.

As shown in FIG. 9, a comparison of the estimated false identification rate to the true false identification rate for a simulated 200-probe experiment demonstrates accurate false identification rate estimation. Referring to the top plot of FIG. 9, identification sensitivity is compared to the true false identification rate and the estimated false identification rate. Referring to the bottom plot of FIG. 9, the estimated false identification rate is plotted against the true false identification rate (as indicated by the solid line), while the dashed line indicates an ideal perfectly accurate false identification rate estimation.

The estimated false identification (ID) rate may be used to threshold a list of protein identifications depending on a tolerance for false identifications.

Example 10: Derivation of a False Discovery Rate Estimation Approach

Consider a list of protein identifications, each protein identification comprising the most likely protein match for an unknown protein, and the associated probability of that match being correct (P(protein|evidence). For example:
prot1–MACD2, $p_1$=0.99
prot2–KCNU1, $p_2$=0.97
prot3–RGL2, $p_3$=0.92
prot4–MTLR, $p_4$=0.9

The expected number of false discoveries in this list is 1–the average matching probability for all proteins in the list. In this case:

$$1 - \frac{0.99 + 0.97 + 0.92 + 0.9}{4} = 0.055$$

The rationale behind this approach is as follows. Consider a list of N protein identifications, and each protein identification $prot_i$ to be a random variable where $prot_i=1$ if the identification is correct and $prot_i=0$ if the identification is incorrect. In this case, the number of correct identifications (correctids) in any list is the sum of these random variables:

$$correctids = \sum_{i=1}^{N} prot_i$$

The expectation value for each individual protein identification is equivalent to the probability of a correct identification:

$$E(prot_i) = 1*p_i + 0*(1-p_i) = p_i$$

By linearity of expectation, it follows that:

$$E(correctids) = \sum_{i=1}^{N} E(prot_i) = \sum_{i=1}^{N} p_i$$

The expected true discovery rate (#correct IDs/#IDs) is the average candidate probability:

$$\frac{E(correctids)}{N} = \frac{1}{N}\sum_{i=1}^{N} p_i = \bar{p}$$

The false discovery rate is 1–true discovery rate, or:

$$1-\bar{p}$$

Example 11: Protein Identification Using Binding Measurement Outcomes

The methods described herein may be applied to different subsets of data associated with the binding and/or non-binding of affinity reagents to unidentified proteins. In some embodiments, methods described herein may be applied to experiments in which a particular subset of the measured binding outcomes is not considered (e.g., non-binding measurement outcomes). These methods where a subset of the measured binding outcomes are not considered may be referred to herein as a "censored" inference approach (e.g., as described in Example 1). In the results described in FIG. 10, the protein identifications that result from the censored inference approach are based on assessing occurrences of binding events associated with the particular unidentified proteins. Accordingly, the censored inference approach does not consider non-binding outcomes in determining identities of unknown proteins.

This type of censored inference approach is in contrast to an "uncensored" approach, in which all obtained binding outcomes are considered (e.g., both binding measurement outcomes and non-binding measurement outcomes associated with the particular unidentified proteins). In some embodiments, a censored approach may be applicable in cases where there is an expectation that particular binding measurements or binding measurement outcomes are more error-prone or likely to deviate from the expected binding measurement outcome for the protein (e.g. the probability of that binding measurement outcome being generated by the protein). For example, in an affinity reagent binding experiment, probabilities of binding measurement outcomes and non-binding measurement outcomes may be calculated based on binding to denatured proteins with predominantly linear structure. In these conditions, epitopes may be easily accessible to affinity reagents. However, in some embodiments, binding measurements on the assayed protein sample may be collected under non-denaturing or partially-denaturing conditions where proteins are present in a "folded" state with significant 3-dimensional structure, which can in many cases cause affinity reagent binding epitopes on the protein that are accessible in a linearized form to be inaccessible due to steric hindrance in the folded state. If, for example, the epitopes that the affinity reagent recognizes for a protein are in structurally accessible regions of the folded protein, the expectation may be that empirical binding measurements acquired on the unknown sample will be consistent with the calculated probabilities of binding derived from linearized proteins. However, if, for example, the epitopes recognized by the affinity reagent are structurally inaccessible, the expectation may be that there will be more non-binding outcomes than expected from calculated probabilities of binding derived from linearized proteins. Further, based on the particular conditions surrounding the protein, the 3-dimensional structure may be configured in a number of different possible configurations, and each of the different possible configurations may have an unique expectation for binding a particular affinity reagent based on the degree of accessibility of the desired affinity reagent.

As such, non-binding outcomes may be expected to deviate from the calculated binding probabilities for each protein, and a censored inference approach which only considers binding outcomes may be appropriate. In the "censored" inference approach as provided in FIG. 10, only measured binding outcomes are considered (in other words, either non-binding outcomes are not measured, or measured non-binding outcomes are not considered), such that the probability of a binding outcome set only considers the M measured binding outcomes that resulted in a binding measurement, which is a subset of the N total measured binding outcomes containing both binding and non-binding measurement outcomes. This may be described by the expression:

$P(\text{outcome set}|\text{protein})=P(\text{binding event 1}|\text{protein})*P(\text{binding event 2}|\text{protein})* \ldots *P(\text{binding event }M|\text{protein})$ When applying a censored approach, it may be appropriate to apply a scaling factor to $P(\text{binding outcome set}|\text{protein})$ to correct for biases. For example, longer proteins generally have a higher probability of generating a potential binding outcome (e.g., because they contain more potential binding sites). To correct for this bias, a scaled likelihood SL may be calculated for each candidate protein by dividing the $P(\text{binding outcome set}|\text{protein})$ by the number of unique combinations of M binding sites that can be generated from the protein based on the number of potential binding sites on the protein. For a protein of length L, with trimer recognition sites, there may be L−2 potential binding sites (e.g., every possible length L subsequence of the complete protein sequence), such that:

$$SL_{Protein} = \frac{P(\text{outcome set}|\text{protein})}{\binom{L-2}{M}} = \frac{P(\text{outcome set}|\text{protein})M!(L-2-M)!}{(L-2)!}$$

The probability of any candidate protein selected from a collection of Q possible candidate proteins, given the outcome set, may be given by:

$$P(protein_i | \text{outcome set}) = \frac{SL_{Protein_i}}{\sum_{j=1}^{Q} SL_{Protein_j}}$$

Figure 10:
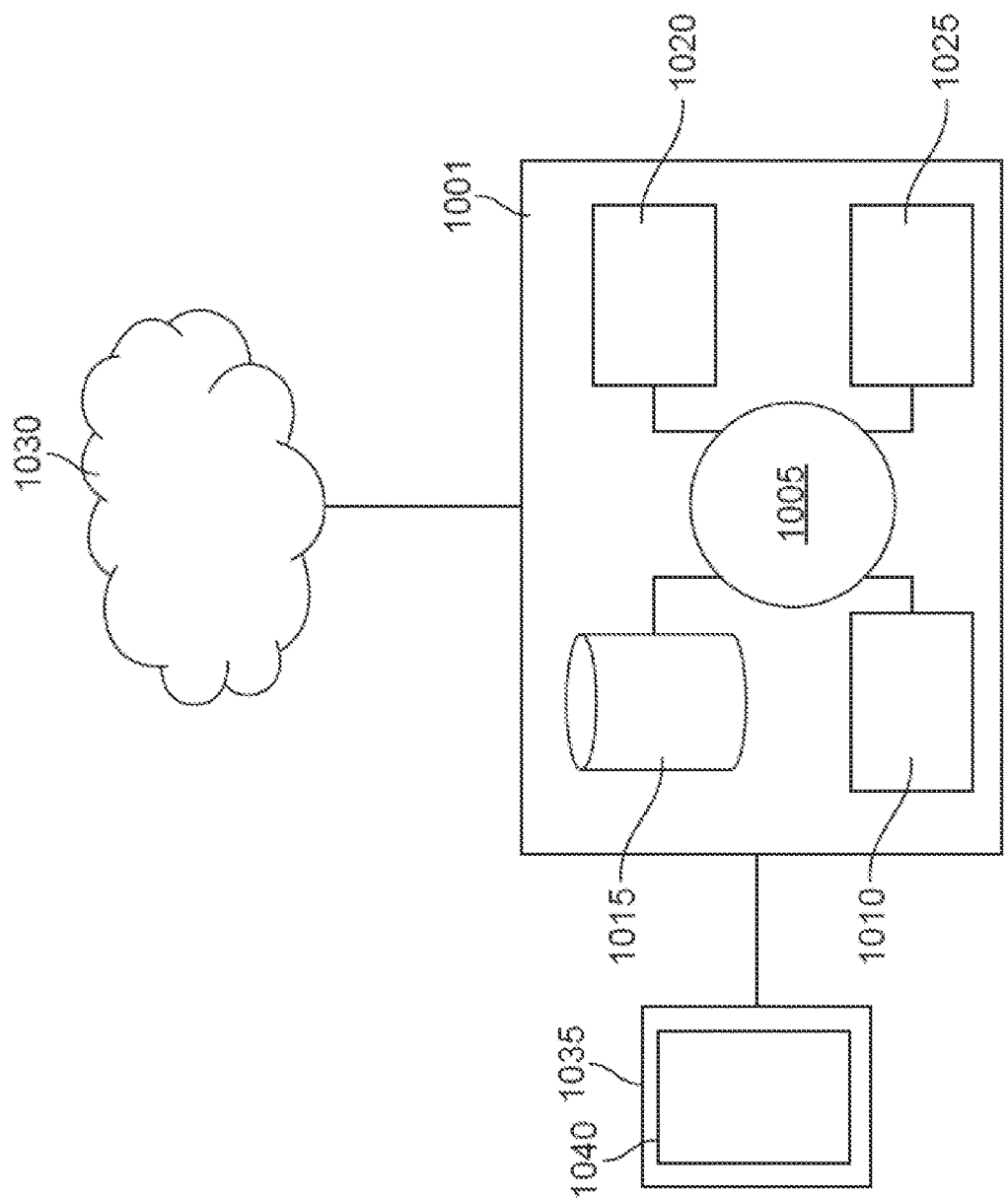
FIG. 10 illustrates a computer control system that is programmed or otherwise configured to implement methods provided herein.

The performance of an embodiment of a censored protein inference vs. uncensored protein inference approach is plotted in FIG. 10. The data plotted in FIG. 10 is provided in Table 1.

TABLE 1

| Censored | Number of Probes | Sensitivity |
|---|---|---|
| TRUE | 100 | 1.52 |
| FALSE | 100 | 56.84 |
| TRUE | 200 | 73.28 |
| FALSE | 200 | 93.18 |
| TRUE | 300 | 93.92 |
| FALSE | 300 | 98.14 |
| TRUE | 400 | 96.68 |
| FALSE | 400 | 98.84 |
| TRUE | 500 | 98.42 |
| FALSE | 500 | 99.6 |

In the comparison shown in FIG. 10, the protein identification sensitivity (e.g., percent of unique proteins identified) is plotted against the number of affinity reagent cycles measured for both censored inference and uncensored inference used on linearized protein substrates. The affinity reagents used are targeted against the top most abundant trimers in the proteome, and each affinity reagent has off-target affinity to four additional random trimers. The uncensored approach outperforms the censored approach by a greater than ten-fold margin when 100 affinity reagent cycles are used. The degree to which uncensored inference outperforms censored inference lessens when more cycles are used.

Figure 11:
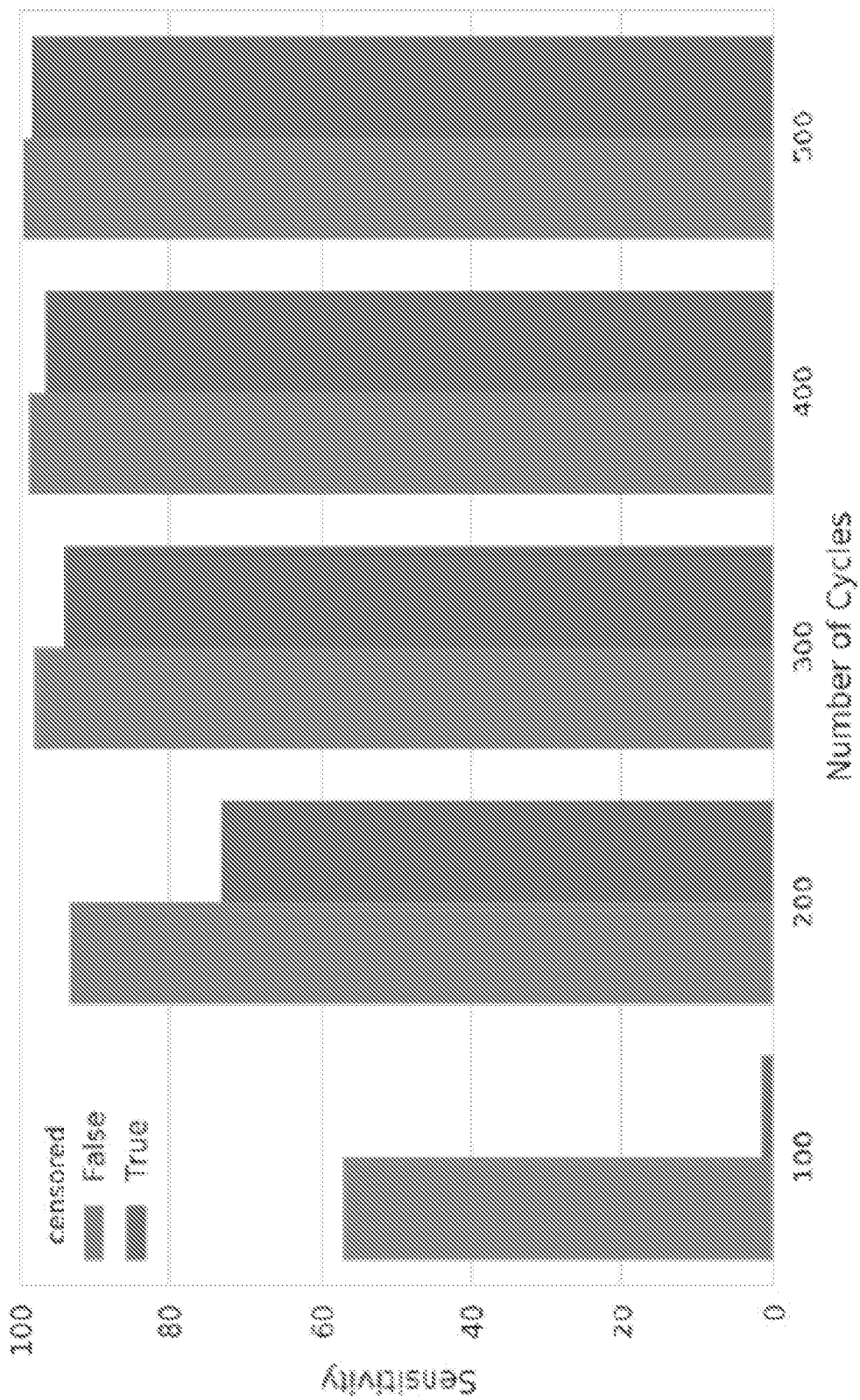
FIG. 11 illustrates the performance of a censored protein identification vs. an uncensored protein identification approach.

Example 12: Tolerance of Protein Identification to Random False Negative and False Positive Affinity Reagent Binding In some cases, there may be a high incidence of false negative binding measurement outcomes for affinity reagent binding. "False negative" binding outcomes manifest as affinity reagent binding measurements occurring less frequently than expected. Such "false negative" outcomes may arise, for example, due to issues with the binding detection method, the binding conditions (for example, temperature, buffer composition, etc.), corruption of the protein sample, or corruption of the affinity reagent stock. To determine the impact of false negative measurements on the censored protein identification and the uncensored protein identification approach, a subset of affinity reagent measurement cycles were purposely corrupted by switching either 1 in 10, 1 in 100, 1 in 1,000, 1 in 10,000, or 1 in 100,000 random observed binding events to non-binding events in silico. Either 0, 1, 50, 100, 200, or 300 of the 300 total affinity reagent cycles were corrupted in this manner. As shown by the results plotted in FIG. 11, both the censored protein identification approach and the uncensored protein identification approach are tolerant to this type of random false negative binding. The data plotted in FIG. 11 is provided in Table 2.

TABLE 2

| Censored | False Negative Rate | Number of Probes | Number of Probes Impacted | Sensitivity |
|---|---|---|---|---|
| TRUE | 0.1 | 300 | 0 | 93.32 |
| FALSE | 0.1 | 300 | 0 | 98.04 |
| TRUE | 0.1 | 300 | 1 | 93.42 |
| FALSE | 0.1 | 300 | 1 | 98.12 |
| TRUE | 0.01 | 300 | 1 | 92.98 |
| FALSE | 0.01 | 300 | 1 | 98.48 |
| TRUE | 0.001 | 300 | 1 | 92.8 |
| FALSE | 0.001 | 300 | 1 | 97.82 |
| TRUE | 0.0001 | 300 | 1 | 92.82 |
| FALSE | 0.0001 | 300 | 1 | 98.32 |
| TRUE | 0.00001 | 300 | 1 | 93.38 |
| FALSE | 0.00001 | 300 | 1 | 98.02 |
| TRUE | 0.1 | 300 | 50 | 92.26 |
| FALSE | 0.1 | 300 | 50 | 97.96 |
| TRUE | 0.01 | 300 | 50 | 92.7 |
| FALSE | 0.01 | 300 | 50 | 97.76 |
| TRUE | 0.001 | 300 | 50 | 93.72 |
| FALSE | 0.001 | 300 | 50 | 98.04 |
| TRUE | 0.0001 | 300 | 50 | 92.96 |
| FALSE | 0.0001 | 300 | 50 | 97.84 |
| TRUE | 0.00001 | 300 | 50 | 93.7 |
| FALSE | 0.00001 | 300 | 50 | 98.1 |
| TRUE | 0.1 | 300 | 100 | 92.38 |
| FALSE | 0.1 | 300 | 100 | 97.66 |
| TRUE | 0.01 | 300 | 100 | 93.02 |
| FALSE | 0.01 | 300 | 100 | 97.7 |
| TRUE | 0.001 | 300 | 100 | 92.48 |
| FALSE | 0.001 | 300 | 100 | 97.96 |
| TRUE | 0.0001 | 300 | 100 | 93.74 |
| FALSE | 0.0001 | 300 | 100 | 98.34 |
| TRUE | 0.00001 | 300 | 100 | 91.88 |
| FALSE | 0.00001 | 300 | 100 | 97.2 |
| TRUE | 0.1 | 300 | 200 | 91.42 |
| FALSE | 0.1 | 300 | 200 | 97.28 |
| TRUE | 0.01 | 300 | 200 | 93.38 |
| FALSE | 0.01 | 300 | 200 | 98.2 |
| TRUE | 0.001 | 300 | 200 | 93.3 |
| FALSE | 0.001 | 300 | 200 | 98.08 |
| TRUE | 0.0001 | 300 | 200 | 92.68 |
| FALSE | 0.0001 | 300 | 200 | 98.12 |
| TRUE | 0.00001 | 300 | 200 | 92.7 |
| FALSE | 0.00001 | 300 | 200 | 98.16 |
| TRUE | 0.1 | 300 | 300 | 90.2 |
| FALSE | 0.1 | 300 | 300 | 97.1 |
| TRUE | 0.01 | 300 | 300 | 92.96 |
| FALSE | 0.01 | 300 | 300 | 98.16 |
| TRUE | 0.001 | 300 | 300 | 93.64 |
| FALSE | 0.001 | 300 | 300 | 98.14 |
| TRUE | 0.0001 | 300 | 300 | 92.92 |
| FALSE | 0.0001 | 300 | 300 | 98.18 |
| TRUE | 0.00001 | 300 | 300 | 92.54 |
| FALSE | 0.00001 | 300 | 300 | 98.14 |

Similarly, "false positive" binding outcomes manifest as affinity reagent binding measurements occurring more frequently than expected. The tolerance to "false positive" binding outcomes was assessed by switching a subset of binding outcomes from non-binding outcomes to binding outcomes. The results of this assessment are provided in Table 3.

TABLE 3

| Censored | False Positive Rate | Number of Probes | Number of Probes Impacted | Sensitivity |
|---|---|---|---|---|
| TRUE | 0.1 | 300 | 0 | 93.32 |
| FALSE | 0.1 | 300 | 0 | 98.04 |
| TRUE | 0.1 | 300 | 1 | 92.54 |
| FALSE | 0.1 | 300 | 1 | 98.26 |
| TRUE | 0.01 | 300 | 1 | 92.74 |
| FALSE | 0.01 | 300 | 1 | 97.94 |
| TRUE | 0.001 | 300 | 1 | 92.48 |
| FALSE | 0.001 | 300 | 1 | 97.88 |
| TRUE | 0.0001 | 300 | 1 | 92.78 |
| FALSE | 0.0001 | 300 | 1 | 98.26 |
| TRUE | 0.00001 | 300 | 1 | 93.06 |
| FALSE | 0.00001 | 300 | 1 | 98.16 |
| TRUE | 0.1 | 300 | 50 | 68.2 |
| FALSE | 0.1 | 300 | 50 | 89.32 |
| TRUE | 0.01 | 300 | 50 | 91.28 |
| FALSE | 0.01 | 300 | 50 | 97.48 |
| TRUE | 0.001 | 300 | 50 | 92.66 |
| FALSE | 0.001 | 300 | 50 | 98.1 |
| TRUE | 0.0001 | 300 | 50 | 93 |
| FALSE | 0.0001 | 300 | 50 | 98.16 |
| TRUE | 0.00001 | 300 | 50 | 93.46 |
| FALSE | 0.00001 | 300 | 50 | 97.68 |
| TRUE | 0.1 | 300 | 100 | 40.98 |
| FALSE | 0.1 | 300 | 100 | 75.02 |
| TRUE | 0.01 | 300 | 100 | 88.56 |
| FALSE | 0.01 | 300 | 100 | 96.94 |
| TRUE | 0.001 | 300 | 100 | 93.34 |
| FALSE | 0.001 | 300 | 100 | 98.26 |
| TRUE | 0.0001 | 300 | 100 | 93.4 |
| FALSE | 0.0001 | 300 | 100 | 97.96 |
| TRUE | 0.00001 | 300 | 100 | 92.62 |
| FALSE | 0.00001 | 300 | 100 | 98.34 |
| TRUE | 0.1 | 300 | 200 | 14.8 |
| FALSE | 0.1 | 300 | 200 | 39.7 |
| TRUE | 0.01 | 300 | 200 | 84.56 |
| FALSE | 0.01 | 300 | 200 | 95.58 |
| TRUE | 0.001 | 300 | 200 | 92.22 |
| FALSE | 0.001 | 300 | 200 | 97.64 |
| TRUE | 0.0001 | 300 | 200 | 93.2 |
| FALSE | 0.0001 | 300 | 200 | 98.12 |
| TRUE | 0.00001 | 300 | 200 | 92.08 |
| FALSE | 0.00001 | 300 | 200 | 98.16 |
| TRUE | 0.1 | 300 | 300 | 3.46 |
| FALSE | 0.1 | 300 | 300 | 17.44 |
| TRUE | 0.01 | 300 | 300 | 79.46 |
| FALSE | 0.01 | 300 | 300 | 93.78 |
| TRUE | 0.001 | 300 | 300 | 92.52 |
| FALSE | 0.001 | 300 | 300 | 97.94 |
| TRUE | 0.0001 | 300 | 300 | 93.36 |
| FALSE | 0.0001 | 300 | 300 | 98.28 |
| TRUE | 0.00001 | 300 | 300 | 93.16 |
| FALSE | 0.00001 | 300 | 300 | 97.78 |

Figure 12:
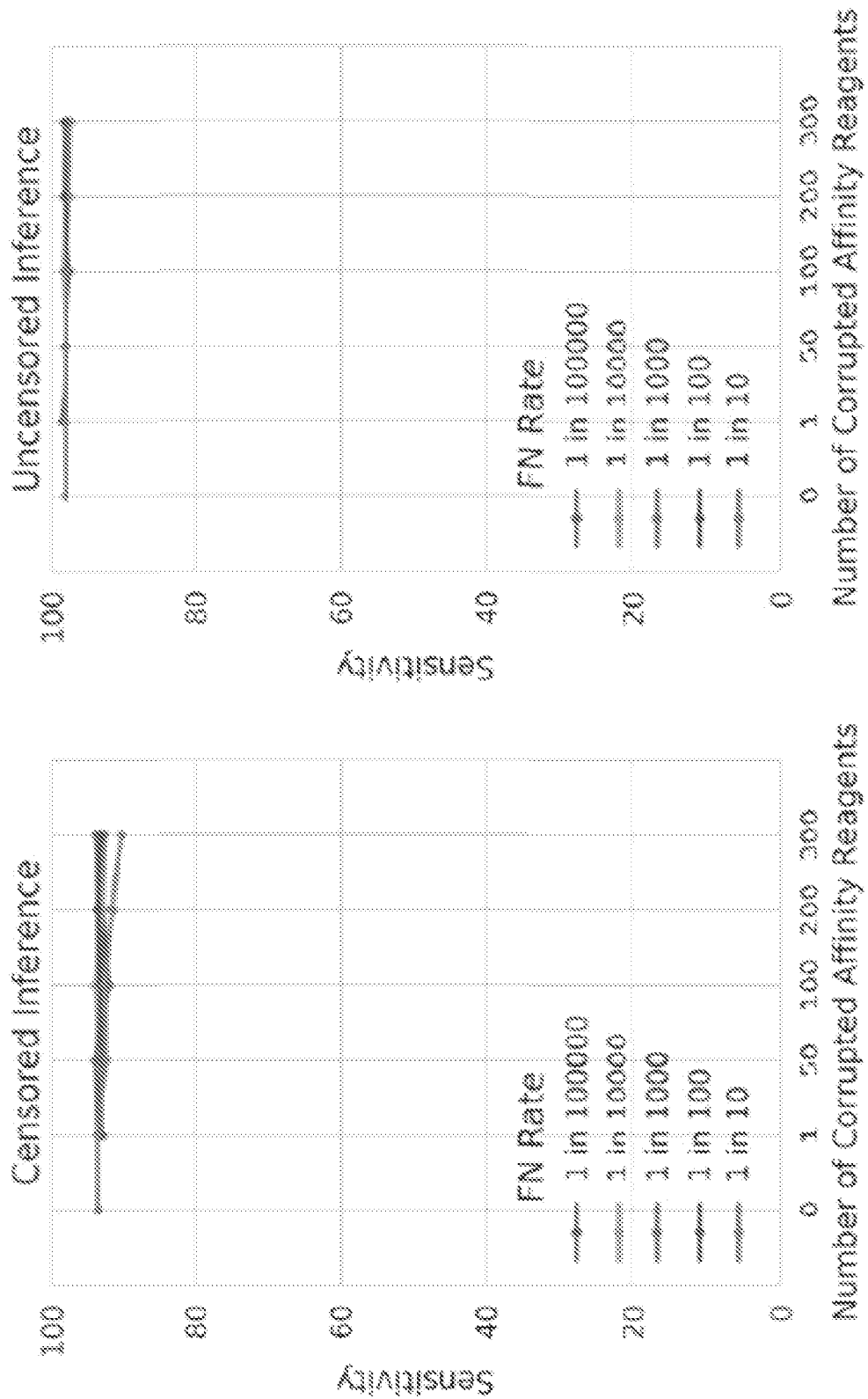
FIG. 12 illustrates the tolerance of censored protein identification and uncensored protein identification approaches to random "false negative" binding outcomes.

These results, which are plotted in FIG. 12, indicate that the performance of a censored protein identification approach degrades more rapidly than the uncensored protein identification approach with increasing incidence of random false positive measurements. However, both approaches tolerate a false positive rate of 1 in 1000 in every affinity reagent cycle or a 1 in 100 rate in a subset of the affinity reagent cycles.

Example 13: Performance of Protein Inference with Overestimated or Underestimated Affinity Reagent Binding Probabilities Protein identification sensitivity was assessed using protein identification with correctly estimated affinity reagent to trimer binding probabilities, and with overestimated or underestimated affinity reagent binding probabilities. The true binding probability was 0.25. The underestimated binding probabilities were: 0.05, 0.1, and 0.2. The overestimated binding probabilities were 0.30, 0.50, 0.75, and 0.90. In total, 300 cycles of affinity reagent measurements were acquired. None (0), all 300, or a subset (1, 50, 100, 200) of the affinity reagents had the overestimated or underestimated binding probabilities applied. All others had the correct binding probabilities (0.25) used in protein identification. The results of the analysis are provided in Table 4.

TABLE 4

| Censored | Inference Binding Probability | Number of Probes | Number of Probes Impacted | Sensitivity | True Binding Probability |
|---|---|---|---|---|---|
| TRUE | 0.05 | 300 | 0 | 93.32 | 0.25 |
| FALSE | 0.05 | 300 | 0 | 98.04 | 0.25 |
| TRUE | 0.05 | 300 | 1 | 94.04 | 0.25 |
| FALSE | 0.05 | 300 | 1 | 98.6 | 0.25 |
| TRUE | 0.1 | 300 | 1 | 93.22 | 0.25 |
| FALSE | 0.1 | 300 | 1 | 97.8 | 0.25 |
| TRUE | 0.2 | 300 | 1 | 92.64 | 0.25 |
| FALSE | 0.2 | 300 | 1 | 98.14 | 0.25 |
| TRUE | 0.25 | 300 | 1 | 93.24 | 0.25 |
| FALSE | 0.25 | 300 | 1 | 97.86 | 0.25 |
| TRUE | 0.3 | 300 | 1 | 93.3 | 0.25 |
| FALSE | 0.3 | 300 | 1 | 98.24 | 0.25 |
| TRUE | 0.5 | 300 | 1 | 93.28 | 0.25 |
| FALSE | 0.5 | 300 | 1 | 97.96 | 0.25 |
| TRUE | 0.75 | 300 | 1 | 93.38 | 0.25 |
| FALSE | 0.75 | 300 | 1 | 97.94 | 0.25 |
| TRUE | 0.9 | 300 | 1 | 92.84 | 0.25 |
| FALSE | 0.9 | 300 | 1 | 97.32 | 0.25 |
| TRUE | 0.05 | 300 | 50 | 92.22 | 0.25 |
| FALSE | 0.05 | 300 | 50 | 97.8 | 0.25 |
| TRUE | 0.1 | 300 | 50 | 93.14 | 0.25 |
| FALSE | 0.1 | 300 | 50 | 98.36 | 0.25 |
| TRUE | 0.2 | 300 | 50 | 93.5 | 0.25 |
| FALSE | 0.2 | 300 | 50 | 98.46 | 0.25 |
| TRUE | 0.25 | 300 | 50 | 92.98 | 0.25 |
| FALSE | 0.25 | 300 | 50 | 98.16 | 0.25 |
| TRUE | 0.3 | 300 | 50 | 92.42 | 0.25 |
| FALSE | 0.3 | 300 | 50 | 98.28 | 0.25 |
| TRUE | 0.5 | 300 | 50 | 93.18 | 0.25 |
| FALSE | 0.5 | 300 | 50 | 98.18 | 0.25 |
| TRUE | 0.75 | 300 | 50 | 92.98 | 0.25 |
| FALSE | 0.75 | 300 | 50 | 96.9 | 0.25 |
| TRUE | 0.9 | 300 | 50 | 92.6 | 0.25 |
| FALSE | 0.9 | 300 | 50 | 94.18 | 0.25 |
| TRUE | 0.05 | 300 | 100 | 92.7 | 0.25 |
| FALSE | 0.05 | 300 | 100 | 97.88 | 0.25 |
| TRUE | 0.1 | 300 | 100 | 93.14 | 0.25 |
| FALSE | 0.1 | 300 | 100 | 97.94 | 0.25 |
| TRUE | 0.2 | 300 | 100 | 92.94 | 0.25 |
| FALSE | 0.2 | 300 | 100 | 97.66 | 0.25 |
| TRUE | 0.25 | 300 | 100 | 92.74 | 0.25 |
| FALSE | 0.25 | 300 | 100 | 97.72 | 0.25 |
| TRUE | 0.3 | 300 | 100 | 93.06 | 0.25 |
| FALSE | 0.3 | 300 | 100 | 98.34 | 0.25 |
| TRUE | 0.5 | 300 | 100 | 92.52 | 0.25 |
| FALSE | 0.5 | 300 | 100 | 98.2 | 0.25 |
| TRUE | 0.75 | 300 | 100 | 92.26 | 0.25 |
| FALSE | 0.75 | 300 | 100 | 95.88 | 0.25 |
| TRUE | 0.9 | 300 | 100 | 91.54 | 0.25 |
| FALSE | 0.9 | 300 | 100 | 84.26 | 0.25 |
| TRUE | 0.05 | 300 | 200 | 91.6 | 0.25 |
| FALSE | 0.05 | 300 | 200 | 95.22 | 0.25 |
| TRUE | 0.1 | 300 | 200 | 93.36 | 0.25 |
| FALSE | 0.1 | 300 | 200 | 97.76 | 0.25 |
| TRUE | 0.2 | 300 | 200 | 92.96 | 0.25 |
| FALSE | 0.2 | 300 | 200 | 97.88 | 0.25 |
| TRUE | 0.25 | 300 | 200 | 93.28 | 0.25 |
| FALSE | 0.25 | 300 | 200 | 98.28 | 0.25 |
| TRUE | 0.3 | 300 | 200 | 92.7 | 0.25 |
| FALSE | 0.3 | 300 | 200 | 97.6 | 0.25 |
| TRUE | 0.5 | 300 | 200 | 92.36 | 0.25 |
| FALSE | 0.5 | 300 | 200 | 97.34 | 0.25 |
| TRUE | 0.75 | 300 | 200 | 91.22 | 0.25 |
| FALSE | 0.75 | 300 | 200 | 88.52 | 0.25 |
| TRUE | 0.9 | 300 | 200 | 90.52 | 0.25 |
| FALSE | 0.9 | 300 | 200 | 33 | 0.25 |
| TRUE | 0.05 | 300 | 300 | 91.7 | 0.25 |
| FALSE | 0.05 | 300 | 300 | 0 | 0.25 |
| TRUE | 0.1 | 300 | 300 | 92.66 | 0.25 |
| FALSE | 0.1 | 300 | 300 | 92.06 | 0.25 |
| TRUE | 0.2 | 300 | 300 | 92.78 | 0.25 |
| FALSE | 0.2 | 300 | 300 | 98.02 | 0.25 |
| TRUE | 0.25 | 300 | 300 | 93.56 | 0.25 |
| FALSE | 0.25 | 300 | 300 | 98.02 | 0.25 |
| TRUE | 0.3 | 300 | 300 | 93 | 0.25 |
| FALSE | 0.3 | 300 | 300 | 98.22 | 0.25 |
| TRUE | 0.5 | 300 | 300 | 91.6 | 0.25 |
| FALSE | 0.5 | 300 | 300 | 96.72 | 0.25 |
| TRUE | 0.75 | 300 | 300 | 90.36 | 0.25 |
| FALSE | 0.75 | 300 | 300 | 67.08 | 0.25 |
| TRUE | 0.9 | 300 | 300 | 88.72 | 0.25 |
| FALSE | 0.9 | 300 | 300 | 0.58 | 0.25 |

Figure 13:
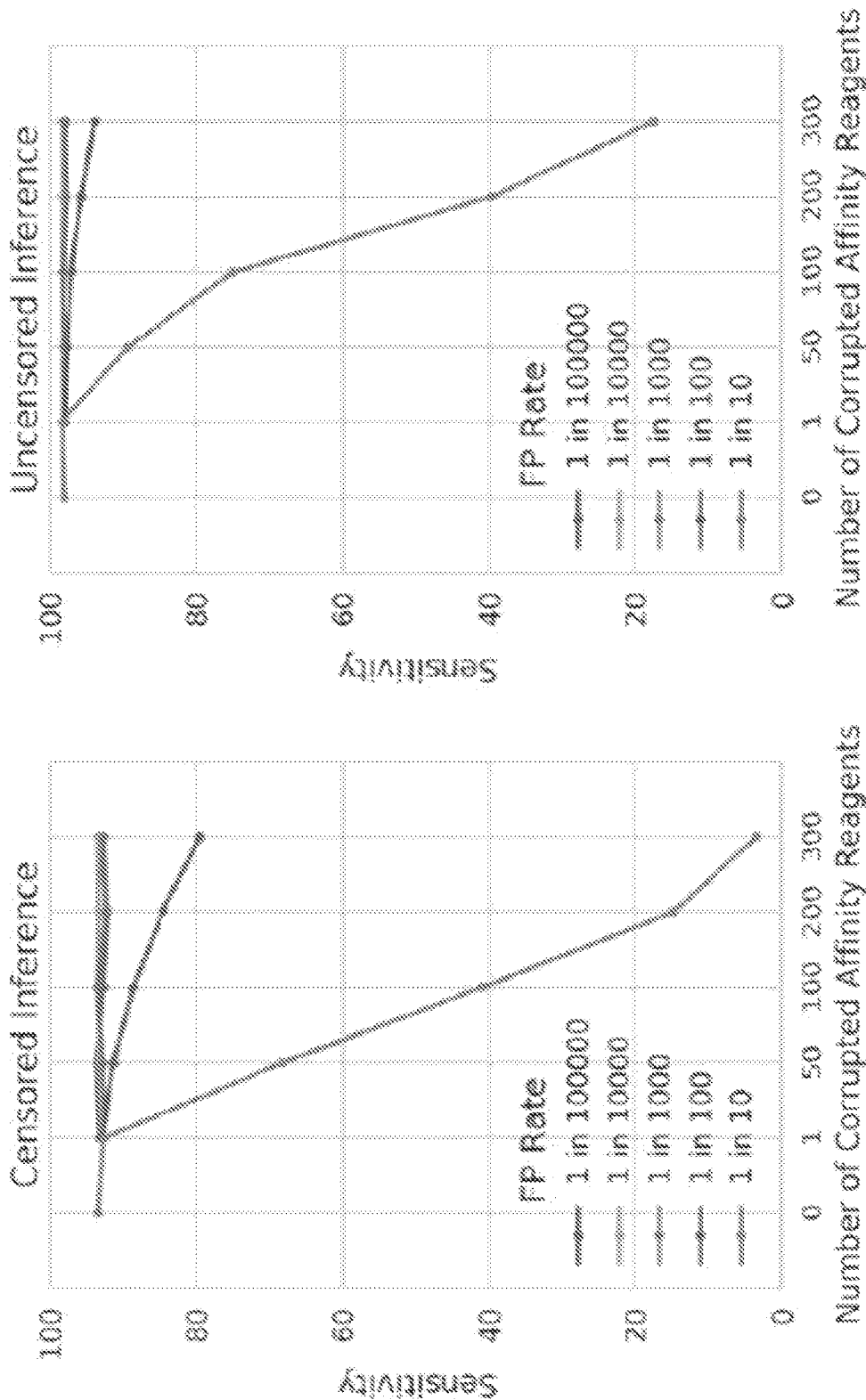
FIG. 13 illustrates the tolerance of censored protein identification and uncensored protein identification approaches to random "false positive" binding outcomes.

These results, which are plotted in FIG. 13, show that censored protein identification may be a preferred approach in some cases where binding probabilities may not be accurately estimated.

Example 14: Performance of Protein Inference Approaches Using Affinity Reagents with Unknown Binding Epitopes In some cases, affinity reagents may possess a number of binding sites (e.g., epitopes) which are unknown. The sensitivity of censored protein identification and uncensored protein identification approaches with affinity reagent binding measurements were compared using affinity reagents that each bind five trimer sites (e.g. a targeted trimer, and four random off-target sites) with probability 0.25 that are input into the protein identification algorithm. A subset of the affinity reagents (0 of 300, 1 of 300, 50 of 300, 100 of 300, 200 of 300, or 300 of 300) had either 1, 4, or 40 additional extra binding sites each against a random trimer with binding probability 0.05, 0.1 or 0.25. The results of the analysis are shown in Table 5.

TABLE 5

| Censored | Extra Sites Binding Probability | Number of Probes | Number of Probes Impacted | Sensitivity | Number of Unknown Extra Sites |
|---|---|---|---|---|---|
| TRUE | 0.05 | 300 | 0 | 93.32 | 1 |
| FALSE | 0.05 | 300 | 0 | 98.04 | 1 |
| TRUE | 0.05 | 300 | 1 | 93.14 | 1 |
| FALSE | 0.05 | 300 | 1 | 97.96 | 1 |
| TRUE | 0.05 | 300 | 1 | 92.68 | 4 |
| FALSE | 0.05 | 300 | 1 | 98.12 | 4 |
| TRUE | 0.05 | 300 | 1 | 92.32 | 40 |
| FALSE | 0.05 | 300 | 1 | 97.82 | 40 |
| TRUE | 0.1 | 300 | 1 | 92.28 | 1 |
| FALSE | 0.1 | 300 | 1 | 98.02 | 1 |

TABLE 5-continued

| Censored | Extra Sites Binding Probability | Number of Probes | Number of Probes Impacted | Sensitivity | Number of Unknown Extra Sites |
|---|---|---|---|---|---|
| TRUE | 0.1 | 300 | 1 | 92.56 | 4 |
| FALSE | 0.1 | 300 | 1 | 98.34 | 4 |
| TRUE | 0.1 | 300 | 1 | 92.64 | 40 |
| FALSE | 0.1 | 300 | 1 | 97.86 | 40 |
| TRUE | 0.25 | 300 | 1 | 93.42 | 1 |
| FALSE | 0.25 | 300 | 1 | 98.46 | 1 |
| TRUE | 0.25 | 300 | 1 | 92.94 | 4 |
| FALSE | 0.25 | 300 | 1 | 98.12 | 4 |
| TRUE | 0.25 | 300 | 1 | 92.36 | 40 |
| FALSE | 0.25 | 300 | 1 | 98.1 | 40 |
| TRUE | 0.05 | 300 | 50 | 93.16 | 1 |
| FALSE | 0.05 | 300 | 50 | 97.94 | 1 |
| TRUE | 0.05 | 300 | 50 | 92.12 | 4 |
| FALSE | 0.05 | 300 | 50 | 97.44 | 4 |
| TRUE | 0.05 | 300 | 50 | 67.5 | 40 |
| FALSE | 0.05 | 300 | 50 | 96.26 | 40 |
| TRUE | 0.1 | 300 | 50 | 92.92 | 1 |
| FALSE | 0.1 | 300 | 50 | 98.34 | 1 |
| TRUE | 0.1 | 300 | 50 | 90.64 | 4 |
| FALSE | 0.1 | 300 | 50 | 97.88 | 4 |
| TRUE | 0.1 | 300 | 50 | 34.98 | 40 |
| FALSE | 0.1 | 300 | 50 | 92.24 | 40 |
| TRUE | 0.25 | 300 | 50 | 91.52 | 1 |
| FALSE | 0.25 | 300 | 50 | 98.12 | 1 |
| TRUE | 0.25 | 300 | 50 | 83.52 | 4 |
| FALSE | 0.25 | 300 | 50 | 97 | 4 |
| TRUE | 0.25 | 300 | 50 | 2.92 | 40 |
| FALSE | 0.25 | 300 | 50 | 37.52 | 40 |
| TRUE | 0.05 | 300 | 100 | 93 | 1 |
| FALSE | 0.05 | 300 | 100 | 97.84 | 1 |
| TRUE | 0.05 | 300 | 100 | 90.3 | 4 |
| FALSE | 0.05 | 300 | 100 | 97.56 | 4 |
| TRUE | 0.05 | 300 | 100 | 28.88 | 40 |
| FALSE | 0.05 | 300 | 100 | 90.12 | 40 |
| TRUE | 0.1 | 300 | 100 | 90.86 | 1 |
| FALSE | 0.1 | 300 | 100 | 97.96 | 1 |
| TRUE | 0.1 | 300 | 100 | 88.52 | 4 |
| FALSE | 0.1 | 300 | 100 | 97.9 | 4 |
| TRUE | 0.1 | 300 | 100 | 3.14 | 40 |
| FALSE | 0.1 | 300 | 100 | 35.04 | 40 |
| TRUE | 0.25 | 300 | 100 | 88.4 | 1 |
| FALSE | 0.25 | 300 | 100 | 97.68 | 1 |
| TRUE | 0.25 | 300 | 100 | 70.06 | 4 |
| FALSE | 0.25 | 300 | 100 | 95.26 | 4 |
| TRUE | 0.25 | 300 | 100 | 0.24 | 40 |
| FALSE | 0.25 | 300 | 100 | 0.08 | 40 |
| TRUE | 0.05 | 300 | 200 | 91.68 | 1 |
| FALSE | 0.05 | 300 | 200 | 98.22 | 1 |
| TRUE | 0.05 | 300 | 200 | 86.8 | 4 |
| FALSE | 0.05 | 300 | 200 | 98.1 | 4 |
| TRUE | 0.05 | 300 | 200 | 2.14 | 40 |
| FALSE | 0.05 | 300 | 200 | 26.82 | 40 |
| TRUE | 0.1 | 300 | 200 | 89.18 | 1 |
| FALSE | 0.1 | 300 | 200 | 97.96 | 1 |
| TRUE | 0.1 | 300 | 200 | 75.24 | 4 |
| FALSE | 0.1 | 300 | 200 | 96.36 | 4 |
| TRUE | 0.1 | 300 | 200 | 0.16 | 40 |
| FALSE | 0.1 | 300 | 200 | 0.16 | 40 |
| TRUE | 0.25 | 300 | 200 | 84.8 | 1 |
| FALSE | 0.25 | 300 | 200 | 96.7 | 1 |
| TRUE | 0.25 | 300 | 200 | 30.92 | 4 |
| FALSE | 0.25 | 300 | 200 | 90.92 | 4 |
| TRUE | 0.25 | 300 | 200 | 0.02 | 40 |
| FALSE | 0.25 | 300 | 200 | 0 | 40 |
| TRUE | 0.05 | 300 | 300 | 91.72 | 1 |
| FALSE | 0.05 | 300 | 300 | 97.68 | 1 |
| TRUE | 0.05 | 300 | 300 | 79.84 | 4 |
| FALSE | 0.05 | 300 | 300 | 96.88 | 4 |
| TRUE | 0.05 | 300 | 300 | 0.64 | 40 |
| FALSE | 0.05 | 300 | 300 | 1.26 | 40 |
| TRUE | 0.1 | 300 | 300 | 88.3 | 1 |
| FALSE | 0.1 | 300 | 300 | 98.34 | 1 |
| TRUE | 0.1 | 300 | 300 | 54.92 | 4 |
| FALSE | 0.1 | 300 | 300 | 95.32 | 4 |
| TRUE | 0.1 | 300 | 300 | 0 | 40 |
| FALSE | 0.1 | 300 | 300 | 0 | 40 |
| TRUE | 0.25 | 300 | 300 | 74.6 | 1 |
| FALSE | 0.25 | 300 | 300 | 97.26 | 1 |
| TRUE | 0.25 | 300 | 300 | 6.22 | 4 |
| FALSE | 0.25 | 300 | 300 | 58.24 | 4 |
| TRUE | 0.25 | 300 | 300 | 0 | 40 |
| FALSE | 0.25 | 300 | 300 | 0 | 40 |

Figure 14:
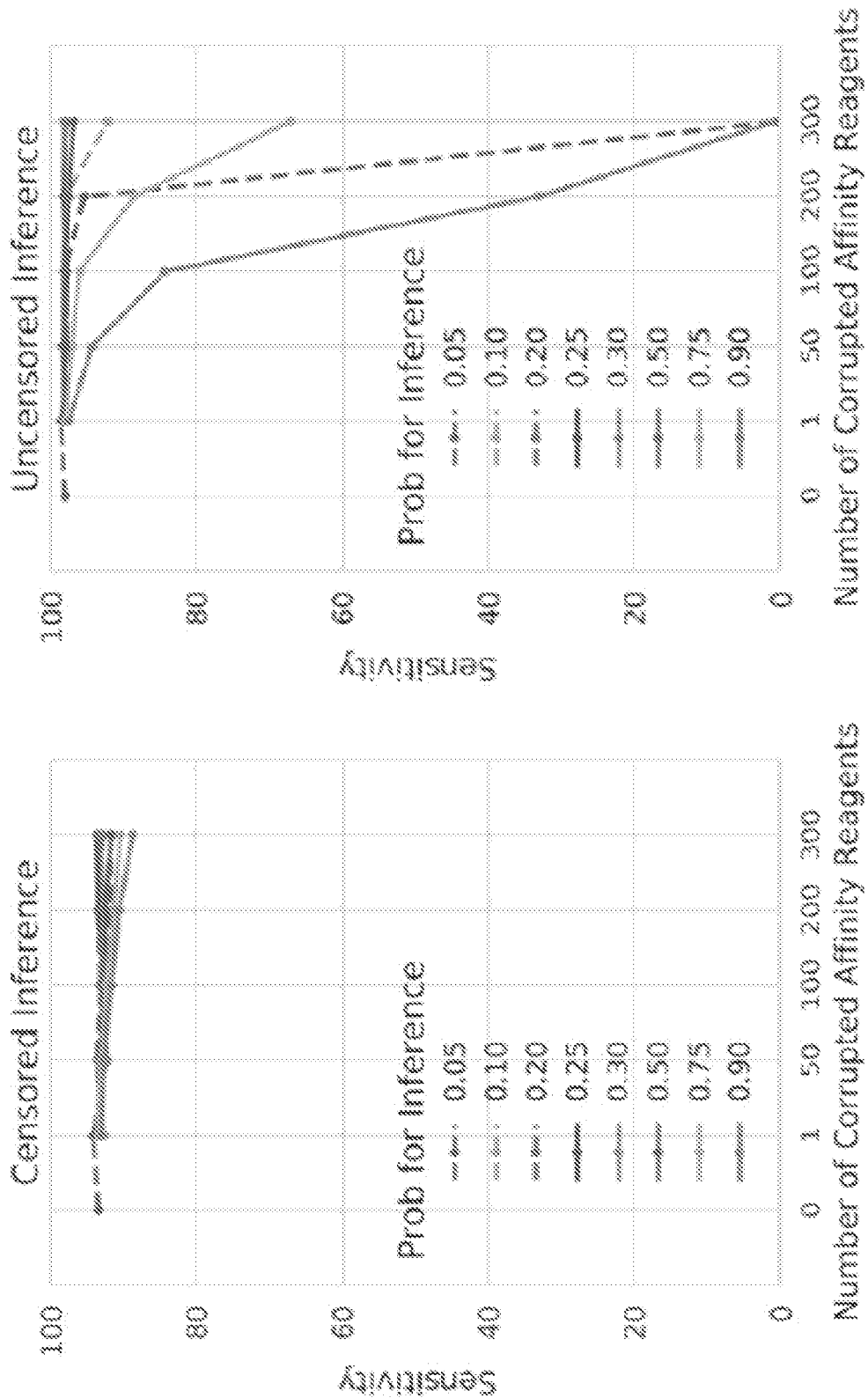
FIG. 14 illustrates the performance of censored protein identification and uncensored protein identification approaches with overestimated or underestimated affinity reagent binding probabilities.

These results, which are plotted in FIG. 14, show that uncensored inference is more tolerant to the inclusion of additional hidden binding sites, and that the performance of both inference approaches is significantly compromised when 50 of the 300 affinity reagents contain 40 additional binding sites.

Example 15: Performance of Protein Inference Approaches Using Affinity Reagents with Missing Binding Epitopes In some cases, there may be improperly characterized affinity reagents with a number of annotated binding epitopes that do not exist (e.g., extra expected binding sites). That is, the model used to generate expected binding probabilities for an affinity reagent contains extra expected sites that do not exist. The sensitivity of censored protein identification and uncensored protein identification approaches with affinity reagent binding measurements were compared using affinity reagents that each bind random trimer sites (e.g. a targeted trimer, and four random off-target sites) with probability 0.25 that are input into the protein identification algorithm. A subset of the affinity reagents (0 of 300, 1 of 300, 50 of 300, 100 of 300, 200 of 300, or 300 of 300) had either 1, 4, or 40 extra expected binding sites each against a random trimer with binding probability 0.05, 0.1 or 0.25 added to the model for the affinity reagent used by the protein inference algorithm. The results of the analysis are shown in Table 6.

TABLE 6

| Censored | Extra Sites Binding Probability | Number of Extra Sites | Number of Probes | Number of Probes Impacted | Sensitivity |
|---|---|---|---|---|---|
| TRUE | 0.05 | 1 | 300 | 0 | 93.32 |
| FALSE | 0.05 | 1 | 300 | 0 | 98.04 |
| TRUE | 0.05 | 1 | 300 | 1 | 94.06 |
| FALSE | 0.05 | 1 | 300 | 1 | 98.6 |
| TRUE | 0.05 | 4 | 300 | 1 | 93.08 |
| FALSE | 0.05 | 4 | 300 | 1 | 98.6 |
| TRUE | 0.05 | 40 | 300 | 1 | 93.38 |
| FALSE | 0.05 | 40 | 300 | 1 | 98.1 |
| TRUE | 0.1 | 1 | 300 | 1 | 92.98 |
| FALSE | 0.1 | 1 | 300 | 1 | 97.88 |
| TRUE | 0.1 | 4 | 300 | 1 | 93.54 |
| FALSE | 0.1 | 4 | 300 | 1 | 98.2 |
| TRUE | 0.1 | 40 | 300 | 1 | 93.26 |
| FALSE | 0.1 | 40 | 300 | 1 | 98.12 |
| TRUE | 0.25 | 1 | 300 | 1 | 92.98 |
| FALSE | 0.25 | 1 | 300 | 1 | 97.62 |
| TRUE | 0.25 | 4 | 300 | 1 | 92.7 |
| FALSE | 0.25 | 4 | 300 | 1 | 98.16 |
| TRUE | 0.25 | 40 | 300 | 1 | 93.06 |
| FALSE | 0.25 | 40 | 300 | 1 | 97.66 |
| TRUE | 0.05 | 1 | 300 | 50 | 92.4 |
| FALSE | 0.05 | 1 | 300 | 50 | 98.2 |
| TRUE | 0.05 | 4 | 300 | 50 | 92.66 |
| FALSE | 0.05 | 4 | 300 | 50 | 98.1 |

TABLE 6-continued

| Censored | Extra Sites Binding Probability | Number of Extra Sites | Number of Probes | Number of Probes Impacted | Sensitivity |
|---|---|---|---|---|---|
| TRUE | 0.05 | 40 | 300 | 50 | 91.14 |
| FALSE | 0.05 | 40 | 300 | 50 | 97.66 |
| TRUE | 0.1 | 1 | 300 | 50 | 93.22 |
| FALSE | 0.1 | 1 | 300 | 50 | 97.9 |
| TRUE | 0.1 | 4 | 300 | 50 | 92.04 |
| FALSE | 0.1 | 4 | 300 | 50 | 97.56 |
| TRUE | 0.1 | 40 | 300 | 50 | 87.74 |
| FALSE | 0.1 | 40 | 300 | 50 | 97.08 |
| TRUE | 0.25 | 1 | 300 | 50 | 92.28 |
| FALSE | 0.25 | 1 | 300 | 50 | 98.26 |
| TRUE | 0.25 | 4 | 300 | 50 | 91.8 |
| FALSE | 0.25 | 4 | 300 | 50 | 97.62 |
| TRUE | 0.25 | 40 | 300 | 50 | 87.16 |
| FALSE | 0.25 | 40 | 300 | 50 | 93.52 |
| TRUE | 0.05 | 1 | 300 | 100 | 91.9 |
| FALSE | 0.05 | 1 | 300 | 100 | 97.64 |
| TRUE | 0.05 | 4 | 300 | 100 | 92.74 |
| FALSE | 0.05 | 4 | 300 | 100 | 98.02 |
| TRUE | 0.05 | 40 | 300 | 100 | 84.18 |
| FALSE | 0.05 | 40 | 300 | 100 | 97.42 |
| TRUE | 0.1 | 1 | 300 | 100 | 92.82 |
| FALSE | 0.1 | 1 | 300 | 100 | 98.08 |
| TRUE | 0.1 | 4 | 300 | 100 | 92.46 |
| FALSE | 0.1 | 4 | 300 | 100 | 97.82 |
| TRUE | 0.1 | 40 | 300 | 100 | 76.28 |
| FALSE | 0.1 | 40 | 300 | 100 | 95.2 |
| TRUE | 0.25 | 1 | 300 | 100 | 91.18 |
| FALSE | 0.25 | 1 | 300 | 100 | 97.84 |
| TRUE | 0.25 | 4 | 300 | 100 | 90.38 |
| FALSE | 0.25 | 4 | 300 | 100 | 97.64 |
| TRUE | 0.25 | 40 | 300 | 100 | 60.5 |
| FALSE | 0.25 | 40 | 300 | 100 | 46.34 |
| TRUE | 0.05 | 1 | 300 | 200 | 93.32 |
| FALSE | 0.05 | 1 | 300 | 200 | 98.16 |
| TRUE | 0.05 | 4 | 300 | 200 | 90.42 |
| FALSE | 0.05 | 4 | 300 | 200 | 97.68 |
| TRUE | 0.05 | 40 | 300 | 200 | 74.82 |
| FALSE | 0.05 | 40 | 300 | 200 | 92.86 |
| TRUE | 0.1 | 1 | 300 | 200 | 93.28 |
| FALSE | 0.1 | 1 | 300 | 200 | 98.2 |
| TRUE | 0.1 | 4 | 300 | 200 | 90.62 |
| FALSE | 0.1 | 4 | 300 | 200 | 98.04 |
| TRUE | 0.1 | 40 | 300 | 200 | 55.4 |
| FALSE | 0.1 | 40 | 300 | 200 | 46.62 |
| TRUE | 0.25 | 1 | 300 | 200 | 92.14 |
| FALSE | 0.25 | 1 | 300 | 200 | 97.88 |
| TRUE | 0.25 | 4 | 300 | 200 | 85.22 |
| FALSE | 0.25 | 4 | 300 | 200 | 96.68 |
| TRUE | 0.25 | 40 | 300 | 200 | 4.92 |
| FALSE | 0.25 | 40 | 300 | 200 | 0.34 |
| TRUE | 0.05 | 1 | 300 | 300 | 92.8 |
| FALSE | 0.05 | 1 | 300 | 300 | 98.34 |
| TRUE | 0.05 | 4 | 300 | 300 | 91.04 |
| FALSE | 0.05 | 4 | 300 | 300 | 97.9 |
| TRUE | 0.05 | 40 | 300 | 300 | 53.2 |
| FALSE | 0.05 | 40 | 300 | 300 | 54.84 |
| TRUE | 0.1 | 1 | 300 | 300 | 91.28 |
| FALSE | 0.1 | 1 | 300 | 300 | 97.44 |
| TRUE | 0.1 | 4 | 300 | 300 | 85.08 |
| FALSE | 0.1 | 4 | 300 | 300 | 97.08 |
| TRUE | 0.1 | 40 | 300 | 300 | 10.66 |
| FALSE | 0.1 | 40 | 300 | 300 | 1.76 |
| TRUE | 0.25 | 1 | 300 | 300 | 90.64 |
| FALSE | 0.25 | 1 | 300 | 300 | 97.54 |
| TRUE | 0.25 | 4 | 300 | 300 | 78.6 |
| FALSE | 0.25 | 4 | 300 | 300 | 95.36 |
| TRUE | 0.25 | 40 | 300 | 300 | 0.06 |
| FALSE | 0.25 | 40 | 300 | 300 | 0 |

Figure 15:
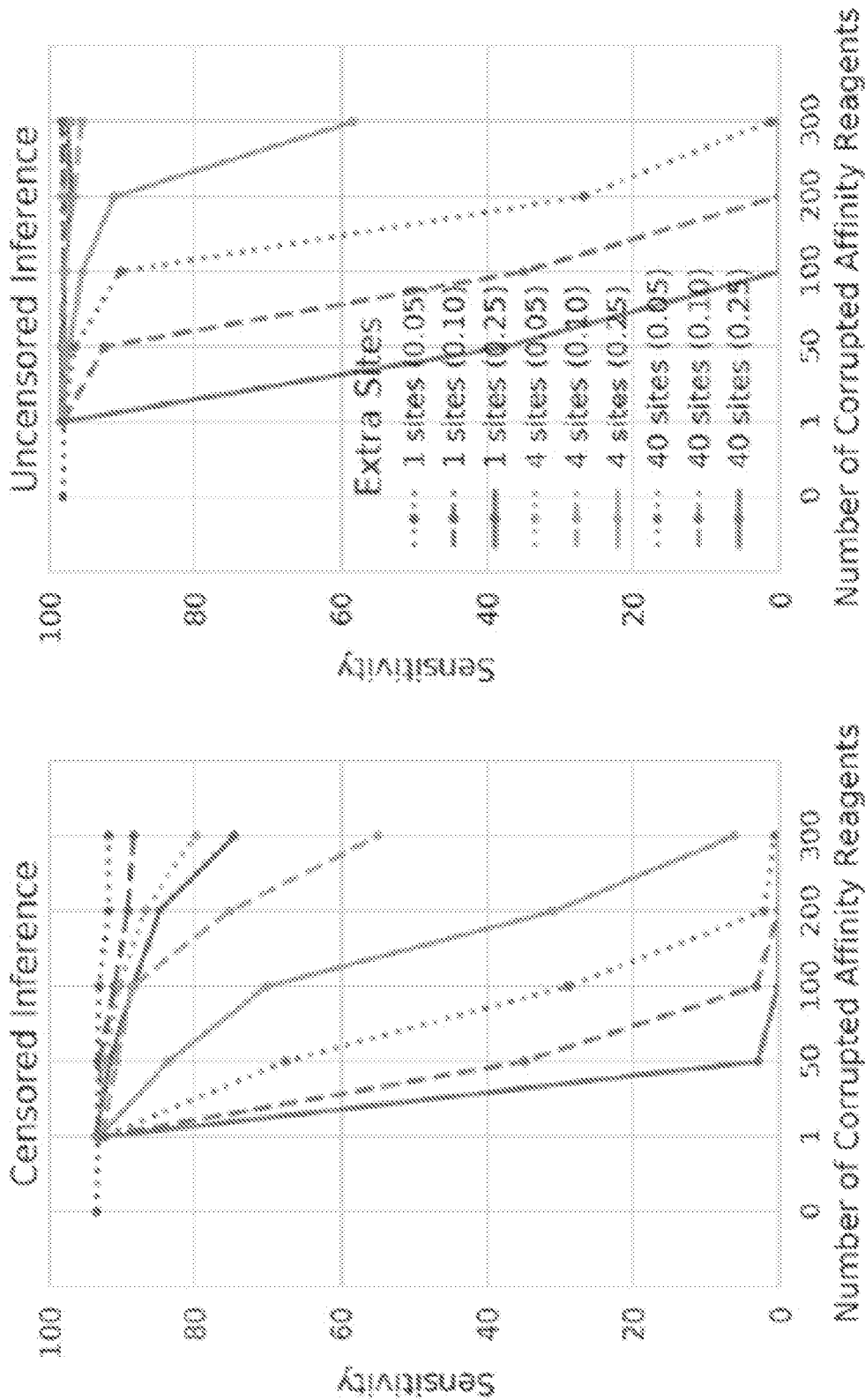
FIG. 15 illustrates the performance of censored protein identification and uncensored protein identification approaches using affinity reagents with unknown binding epitopes.

These results, which are plotted in FIG. 15, show that uncensored inference is more tolerant to the inclusion of extra expected binding sites included in the model of affinity reagent binding, and that the performance of both protein identification approaches is compromised to some degree when the majority of affinity reagents contain 40 extra expected binding sites.

Example 16: Censored Inference for Affinity Reagent Binding Analysis with an Alternative Scaling Strategy The methods described herein may be applied to infer protein identity (e.g., identify unknown proteins) using affinity reagent binding measurements in combination with various probability scaling strategies. The censored inference approach described in Example 11 scales the probability of an observed outcome for a protein based on the number of potential binding sites on the protein (protein length–2) and the number of observed binding outcomes (M):

$$SL_{Protein} = \frac{P(\text{outcome set} \mid \text{protein})}{\binom{L-2}{M}}$$

The methods described herein may be applied with alternative approaches for computing scaled likelihoods. This example applies an alternative approach for normalization that models the probability of generating N binding events for a protein of length k from the set of affinity reagents used to measure the protein, and scales based on this probability. First, for each probe, the probability of the probe binding a trimer of unknown identity in the sample is calculated:

$$P(\text{trimer bind} \mid probe_i) = \sum_{j=1}^{j=8000} P(trimer_j) P(probe_i \text{bind} \mid trimer_j)$$

where $P(trimer_j)$ is the frequency with which the trimer occurs relative to the summed count of all 8,000 trimers in the proteome. For any protein of length k, the probability of a probe i binding the protein may be given by:

$$P(\text{protein bind} \mid probe_i, k) = 1-(1-P(\text{trimer bind} \mid probe_i))^{k-2}$$

The number of successful binding events observed for a protein of length k may follow a Poisson-Binomial distribution with n trials, where n is the number of probe binding measurements made for the protein and the parameters $p_{probes,k}$ of the distribution indicate the probability of success for each trial:

$$p_{probes,k} = [P(\text{bind} \mid probe_1, k), P(\text{bind} \mid probe_2, k), P(\text{bind} \mid probe_3, k) \ldots P(\text{bind} \mid probe_n, k)].$$

The probability of generating N binding events from a protein of length k, with a particular set of probes, may be given by the probability mass function of the Poisson binomial distribution ($PMF_{PoiBin}$) parameterized by p, evaluated at N:

$$P(N \text{ binding events} \mid probes, k) = PMF_{PoiBin}(N, p_{probes}, k)$$

The scaled likelihood of a particular outcome set is computed based on this probability:

$$SL_{protein, binding events} = \frac{P(\text{outcome set} \mid \text{protein})}{P(N \text{ binding events} \mid probes, k)}$$

Example 17: Using Randomly Selected Affinity Reagents

The methods described herein may be applied to any set of affinity reagents. For example, the protein identification approach may be applied to a set of affinity reagents targeting the most abundant trimers in the proteome, or targeting random trimers. The results from a human protein inference analysis using affinity reagents targeting the top 300 least abundant trimers in the proteome, 300 randomly selected trimers in the proteome, or the 300 most abundant trimers in the proteome, are shown in Tables 7A-7C, respectively.

TABLE 7A 300 affinity reagents targeting the least-abundant trimers in the proteome

| Number of Probes | Probe Set ID | Experiment Repetition | Selection Type | Sensitivity |
|---|---|---|---|---|
| 300 | 100 | 0 | Bottom 300 | 91.9 |
| 300 | 100 | 1 | Bottom 300 | 91.24 |
| 300 | 100 | 2 | Bottom 300 | 91.74 |
| 300 | 100 | 3 | Bottom 300 | 90.9 |
| 300 | 100 | 4 | Bottom 300 | 90.46 |

TABLE 7B 300 affinity reagents targeting random trimers in the proteome

| Number of Probes | Probe Set ID | Experiment Repetition | Selection Type | Sensitivity |
|---|---|---|---|---|
| 300 | 0 | 0 | Random | 94.4 |
| 300 | 0 | 1 | Random | 94.2 |
| 300 | 0 | 2 | Random | 94.18 |
| 300 | 0 | 3 | Random | 94.64 |
| 300 | 0 | 4 | Random | 94.24 |
| 300 | 1 | 0 | Random | 94.12 |
| 300 | 1 | 1 | Random | 94.08 |
| 300 | 1 | 2 | Random | 94.12 |
| 300 | 1 | 3 | Random | 93.7 |
| 300 | 1 | 4 | Random | 93.54 |
| 300 | 2 | 0 | Random | 93.68 |
| 300 | 2 | 1 | Random | 93.68 |
| 300 | 2 | 2 | Random | 93.68 |
| 300 | 2 | 3 | Random | 93.74 |
| 300 | 2 | 4 | Random | 93.9 |
| 300 | 3 | 0 | Random | 95.12 |
| 300 | 3 | 1 | Random | 94.38 |
| 300 | 3 | 2 | Random | 94.76 |
| 300 | 3 | 3 | Random | 95.4 |
| 300 | 3 | 4 | Random | 94.6 |
| 300 | 4 | 0 | Random | 94.46 |
| 300 | 4 | 1 | Random | 94.74 |
| 300 | 4 | 2 | Random | 95.04 |
| 300 | 4 | 3 | Random | 94.66 |
| 300 | 4 | 4 | Random | 94.76 |
| 300 | 5 | 0 | Random | 94.58 |
| 300 | 5 | 1 | Random | 94.62 |
| 300 | 5 | 2 | Random | 94.48 |
| 300 | 5 | 3 | Random | 94.48 |
| 300 | 5 | 4 | Random | 95 |
| 300 | 6 | 0 | Random | 93.18 |
| 300 | 6 | 1 | Random | 93.44 |
| 300 | 6 | 2 | Random | 93.28 |
| 300 | 6 | 3 | Random | 93.8 |
| 300 | 6 | 4 | Random | 94.26 |
| 300 | 7 | 0 | Random | 95.16 |
| 300 | 7 | 1 | Random | 94.02 |
| 300 | 7 | 2 | Random | 95 |
| 300 | 7 | 3 | Random | 95.1 |
| 300 | 7 | 4 | Random | 94.86 |
| 300 | 8 | 0 | Random | 93.56 |
| 300 | 8 | 1 | Random | 95.5 |
| 300 | 8 | 2 | Random | 94.7 |
| 300 | 8 | 3 | Random | 94.72 |
| 300 | 8 | 4 | Random | 94.94 |
| 300 | 9 | 0 | Random | 94.46 |
| 300 | 9 | 1 | Random | 95.44 |
| 300 | 9 | 2 | Random | 93.98 |
| 300 | 9 | 3 | Random | 94.58 |
| 300 | 9 | 4 | Random | 94.34 |
| 300 | 10 | 0 | Random | 94.54 |
| 300 | 10 | 1 | Random | 94.56 |
| 300 | 10 | 2 | Random | 94.78 |
| 300 | 10 | 3 | Random | 94.86 |
| 300 | 10 | 4 | Random | 95.08 |
| 300 | 11 | 0 | Random | 94.36 |
| 300 | 11 | 1 | Random | 94.86 |
| 300 | 11 | 2 | Random | 95.3 |
| 300 | 11 | 3 | Random | 94.16 |
| 300 | 11 | 4 | Random | 94.9 |
| 300 | 12 | 0 | Random | 94.92 |
| 300 | 12 | 1 | Random | 94.66 |
| 300 | 12 | 2 | Random | 94.26 |
| 300 | 12 | 3 | Random | 94.58 |
| 300 | 12 | 4 | Random | 94.02 |
| 300 | 13 | 0 | Random | 94.78 |
| 300 | 13 | 1 | Random | 94.54 |
| 300 | 13 | 2 | Random | 95.02 |
| 300 | 13 | 3 | Random | 94.94 |
| 300 | 13 | 4 | Random | 94.98 |
| 300 | 14 | 0 | Random | 95.3 |
| 300 | 14 | 1 | Random | 94.36 |
| 300 | 14 | 2 | Random | 94.76 |
| 300 | 14 | 3 | Random | 95.26 |
| 300 | 14 | 4 | Random | 94.52 |
| 300 | 15 | 0 | Random | 94.48 |
| 300 | 15 | 1 | Random | 94.6 |
| 300 | 15 | 2 | Random | 94.98 |
| 300 | 15 | 3 | Random | 94.6 |
| 300 | 15 | 4 | Random | 95.8 |
| 300 | 16 | 0 | Random | 94.58 |
| 300 | 16 | 1 | Random | 92.96 |
| 300 | 16 | 2 | Random | 94.6 |
| 300 | 16 | 3 | Random | 93.84 |
| 300 | 16 | 4 | Random | 94.38 |
| 300 | 17 | 0 | Random | 94.76 |
| 300 | 17 | 1 | Random | 94.54 |
| 300 | 17 | 2 | Random | 94.72 |
| 300 | 17 | 3 | Random | 94.24 |
| 300 | 17 | 4 | Random | 94.12 |
| 300 | 18 | 0 | Random | 94.16 |
| 300 | 18 | 1 | Random | 94.1 |
| 300 | 18 | 2 | Random | 94.86 |
| 300 | 18 | 3 | Random | 93.98 |
| 300 | 18 | 4 | Random | 95.04 |
| 300 | 19 | 0 | Random | 93.58 |
| 300 | 19 | 1 | Random | 94.94 |
| 300 | 19 | 2 | Random | 95.12 |
| 300 | 19 | 3 | Random | 94.8 |
| 300 | 19 | 4 | Random | 94.8 |
| 300 | 20 | 0 | Random | 93 |
| 300 | 20 | 1 | Random | 94.22 |
| 300 | 20 | 2 | Random | 94.4 |
| 300 | 20 | 3 | Random | 93.64 |
| 300 | 20 | 4 | Random | 94.76 |
| 300 | 21 | 0 | Random | 93.68 |
| 300 | 21 | 1 | Random | 94.18 |
| 300 | 21 | 2 | Random | 94.38 |
| 300 | 21 | 3 | Random | 94.48 |
| 300 | 21 | 4 | Random | 94.68 |
| 300 | 22 | 0 | Random | 93.66 |
| 300 | 22 | 1 | Random | 94.16 |
| 300 | 22 | 2 | Random | 94.1 |
| 300 | 22 | 3 | Random | 94.16 |
| 300 | 22 | 4 | Random | 94.1 |
| 300 | 23 | 0 | Random | 93.94 |
| 300 | 23 | 1 | Random | 94.42 |
| 300 | 23 | 2 | Random | 94.24 |
| 300 | 23 | 3 | Random | 93.9 |

TABLE 7B-continued 300 affinity reagents targeting random trimers in the proteome

| Number of Probes | Probe Set ID | Experiment Repetition | Selection Type | Sensitivity |
|---|---|---|---|---|
| 300 | 23 | 4 | Random | 94.4 |
| 300 | 24 | 0 | Random | 95 |
| 300 | 24 | 1 | Random | 94.82 |
| 300 | 24 | 2 | Random | 94.16 |
| 300 | 24 | 3 | Random | 94.58 |
| 300 | 24 | 4 | Random | 94.54 |
| 300 | 25 | 0 | Random | 94.5 |
| 300 | 25 | 1 | Random | 95.1 |
| 300 | 25 | 2 | Random | 95.3 |
| 300 | 25 | 3 | Random | 94.54 |
| 300 | 25 | 4 | Random | 95.22 |
| 300 | 26 | 0 | Random | 94.22 |
| 300 | 26 | 1 | Random | 94.08 |
| 300 | 26 | 2 | Random | 94.52 |
| 300 | 26 | 3 | Random | 94.3 |
| 300 | 26 | 4 | Random | 94.6 |
| 300 | 27 | 0 | Random | 93.92 |
| 300 | 27 | 1 | Random | 94.24 |
| 300 | 27 | 2 | Random | 93.64 |
| 300 | 27 | 3 | Random | 93.84 |
| 300 | 27 | 4 | Random | 94.04 |
| 300 | 28 | 0 | Random | 94.08 |
| 300 | 28 | 1 | Random | 95.14 |
| 300 | 28 | 2 | Random | 94.82 |
| 300 | 28 | 3 | Random | 94.7 |
| 300 | 28 | 4 | Random | 94.92 |
| 300 | 29 | 0 | Random | 94.82 |
| 300 | 29 | 1 | Random | 93.76 |
| 300 | 29 | 2 | Random | 93.98 |
| 300 | 29 | 3 | Random | 93.14 |
| 300 | 29 | 4 | Random | 94.46 |
| 300 | 30 | 0 | Random | 94.6 |
| 300 | 30 | 1 | Random | 96.22 |
| 300 | 30 | 2 | Random | 95.06 |
| 300 | 30 | 3 | Random | 95.12 |
| 300 | 30 | 4 | Random | 94.82 |
| 300 | 31 | 0 | Random | 93.12 |
| 300 | 31 | 1 | Random | 93.92 |
| 300 | 31 | 2 | Random | 93.3 |
| 300 | 31 | 3 | Random | 94.7 |
| 300 | 31 | 4 | Random | 94.22 |
| 300 | 32 | 0 | Random | 93.7 |
| 300 | 32 | 1 | Random | 94.62 |
| 300 | 32 | 2 | Random | 94.12 |
| 300 | 32 | 3 | Random | 94.08 |
| 300 | 32 | 4 | Random | 94.72 |
| 300 | 33 | 0 | Random | 94.82 |
| 300 | 33 | 1 | Random | 93.44 |
| 300 | 33 | 2 | Random | 94.06 |
| 300 | 33 | 3 | Random | 94.54 |
| 300 | 33 | 4 | Random | 94.42 |
| 300 | 34 | 0 | Random | 94.16 |
| 300 | 34 | 1 | Random | 93.28 |
| 300 | 34 | 2 | Random | 94.9 |
| 300 | 34 | 3 | Random | 93.12 |
| 300 | 34 | 4 | Random | 94.3 |
| 300 | 35 | 0 | Random | 94.54 |
| 300 | 35 | 1 | Random | 93.56 |
| 300 | 35 | 2 | Random | 93.4 |
| 300 | 35 | 3 | Random | 93.78 |
| 300 | 35 | 4 | Random | 94.5 |
| 300 | 36 | 0 | Random | 94.34 |
| 300 | 36 | 1 | Random | 93.9 |
| 300 | 36 | 2 | Random | 94.7 |
| 300 | 36 | 3 | Random | 95.12 |
| 300 | 36 | 4 | Random | 94.8 |
| 300 | 37 | 0 | Random | 94.38 |
| 300 | 37 | 1 | Random | 95.22 |
| 300 | 37 | 2 | Random | 94.98 |
| 300 | 37 | 3 | Random | 94.12 |
| 300 | 37 | 4 | Random | 95.06 |
| 300 | 38 | 0 | Random | 94.34 |
| 300 | 38 | 1 | Random | 94.82 |
| 300 | 38 | 2 | Random | 93.8 |
| 300 | 38 | 3 | Random | 94.8 |
| 300 | 38 | 4 | Random | 95.1 |
| 300 | 39 | 0 | Random | 93.72 |
| 300 | 39 | 1 | Random | 93.7 |
| 300 | 39 | 2 | Random | 94.12 |
| 300 | 39 | 3 | Random | 94.04 |
| 300 | 39 | 4 | Random | 93.98 |
| 300 | 40 | 0 | Random | 94.42 |
| 300 | 40 | 1 | Random | 93.86 |
| 300 | 40 | 2 | Random | 93.46 |
| 300 | 40 | 3 | Random | 94.34 |
| 300 | 40 | 4 | Random | 94.12 |
| 300 | 41 | 0 | Random | 94.16 |
| 300 | 41 | 1 | Random | 95 |
| 300 | 41 | 2 | Random | 95.22 |
| 300 | 41 | 3 | Random | 95.38 |
| 300 | 41 | 4 | Random | 95.36 |
| 300 | 42 | 0 | Random | 93.36 |
| 300 | 42 | 1 | Random | 94.38 |
| 300 | 42 | 2 | Random | 94.28 |
| 300 | 42 | 3 | Random | 94.52 |
| 300 | 42 | 4 | Random | 93.94 |
| 300 | 43 | 0 | Random | 95.5 |
| 300 | 43 | 1 | Random | 95.04 |
| 300 | 43 | 2 | Random | 95.32 |
| 300 | 43 | 3 | Random | 94.84 |
| 300 | 43 | 4 | Random | 95.26 |
| 300 | 44 | 0 | Random | 94.74 |
| 300 | 44 | 1 | Random | 94.6 |
| 300 | 44 | 2 | Random | 93.8 |
| 300 | 44 | 3 | Random | 94.04 |
| 300 | 44 | 4 | Random | 94.22 |
| 300 | 45 | 0 | Random | 93.64 |
| 300 | 45 | 1 | Random | 93.78 |
| 300 | 45 | 2 | Random | 94.12 |
| 300 | 45 | 3 | Random | 94.48 |
| 300 | 45 | 4 | Random | 94.66 |
| 300 | 46 | 0 | Random | 94.48 |
| 300 | 46 | 1 | Random | 94.92 |
| 300 | 46 | 2 | Random | 95.04 |
| 300 | 46 | 3 | Random | 94.14 |
| 300 | 46 | 4 | Random | 94.6 |
| 300 | 47 | 0 | Random | 94.2 |
| 300 | 47 | 1 | Random | 93.56 |
| 300 | 47 | 2 | Random | 95.36 |
| 300 | 47 | 3 | Random | 95.64 |
| 300 | 47 | 4 | Random | 94.18 |
| 300 | 48 | 0 | Random | 94.38 |
| 300 | 48 | 1 | Random | 95.1 |
| 300 | 48 | 2 | Random | 94.24 |
| 300 | 48 | 3 | Random | 94.6 |
| 300 | 48 | 4 | Random | 94.76 |
| 300 | 49 | 0 | Random | 94.98 |
| 300 | 49 | 1 | Random | 95.9 |
| 300 | 49 | 2 | Random | 95.08 |
| 300 | 49 | 3 | Random | 94.72 |
| 300 | 49 | 4 | Random | 94.02 |
| 300 | 50 | 0 | Random | 94.72 |
| 300 | 50 | 1 | Random | 94.44 |
| 300 | 50 | 2 | Random | 95.84 |
| 300 | 50 | 3 | Random | 95 |
| 300 | 50 | 4 | Random | 94.62 |
| 300 | 51 | 0 | Random | 94.92 |
| 300 | 51 | 1 | Random | 94.26 |
| 300 | 51 | 2 | Random | 94.34 |
| 300 | 51 | 3 | Random | 94.66 |
| 300 | 51 | 4 | Random | 93.58 |
| 300 | 52 | 0 | Random | 94.98 |
| 300 | 52 | 1 | Random | 95.12 |
| 300 | 52 | 2 | Random | 94.88 |
| 300 | 52 | 3 | Random | 94.78 |
| 300 | 52 | 4 | Random | 94.88 |
| 300 | 53 | 0 | Random | 94.88 |
| 300 | 53 | 1 | Random | 95.04 |
| 300 | 53 | 2 | Random | 94.18 |
| 300 | 53 | 3 | Random | 94.04 |

TABLE 7B-continued 300 affinity reagents targeting random trimers in the proteome

| Number of Probes | Probe Set ID | Experiment Repetition | Selection Type | Sensitivity |
|---|---|---|---|---|
| 300 | 53 | 4 | Random | 94.56 |
| 300 | 54 | 0 | Random | 94.26 |
| 300 | 54 | 1 | Random | 94.1 |
| 300 | 54 | 2 | Random | 95.32 |
| 300 | 54 | 3 | Random | 94.44 |
| 300 | 54 | 4 | Random | 94.74 |
| 300 | 55 | 0 | Random | 94.68 |
| 300 | 55 | 1 | Random | 94.68 |
| 300 | 55 | 2 | Random | 95.52 |
| 300 | 55 | 3 | Random | 94.54 |
| 300 | 55 | 4 | Random | 95.12 |
| 300 | 56 | 0 | Random | 94.58 |
| 300 | 56 | 1 | Random | 95.14 |
| 300 | 56 | 2 | Random | 94.58 |
| 300 | 56 | 3 | Random | 95.18 |
| 300 | 56 | 4 | Random | 94.84 |
| 300 | 57 | 0 | Random | 94.54 |
| 300 | 57 | 1 | Random | 93.82 |
| 300 | 57 | 2 | Random | 94.92 |
| 300 | 57 | 3 | Random | 95.14 |
| 300 | 57 | 4 | Random | 94.26 |
| 300 | 58 | 0 | Random | 94.36 |
| 300 | 58 | 1 | Random | 94.74 |
| 300 | 58 | 2 | Random | 94.92 |
| 300 | 58 | 3 | Random | 94.36 |
| 300 | 58 | 4 | Random | 94.28 |
| 300 | 59 | 0 | Random | 94.54 |
| 300 | 59 | 1 | Random | 93.92 |
| 300 | 59 | 2 | Random | 95.04 |
| 300 | 59 | 3 | Random | 95.4 |
| 300 | 59 | 4 | Random | 93.76 |
| 300 | 60 | 0 | Random | 94.8 |
| 300 | 60 | 1 | Random | 94.74 |
| 300 | 60 | 2 | Random | 93.82 |
| 300 | 60 | 3 | Random | 94.54 |
| 300 | 60 | 4 | Random | 93.86 |
| 300 | 61 | 0 | Random | 94.5 |
| 300 | 61 | 1 | Random | 94.76 |
| 300 | 61 | 2 | Random | 94.3 |
| 300 | 61 | 3 | Random | 94.68 |
| 300 | 61 | 4 | Random | 94.42 |
| 300 | 62 | 0 | Random | 93.72 |
| 300 | 62 | 1 | Random | 94.94 |
| 300 | 62 | 2 | Random | 94.12 |
| 300 | 62 | 3 | Random | 93.86 |
| 300 | 62 | 4 | Random | 95.38 |
| 300 | 63 | 0 | Random | 95.1 |
| 300 | 63 | 1 | Random | 95.4 |
| 300 | 63 | 2 | Random | 94.94 |
| 300 | 63 | 3 | Random | 94.62 |
| 300 | 63 | 4 | Random | 94.32 |
| 300 | 64 | 0 | Random | 94.96 |
| 300 | 64 | 1 | Random | 94.02 |
| 300 | 64 | 2 | Random | 94.52 |
| 300 | 64 | 3 | Random | 93.98 |
| 300 | 64 | 4 | Random | 94.48 |
| 300 | 65 | 0 | Random | 93.6 |
| 300 | 65 | 1 | Random | 94.4 |
| 300 | 65 | 2 | Random | 93.38 |
| 300 | 65 | 3 | Random | 94.54 |
| 300 | 65 | 4 | Random | 93.14 |
| 300 | 66 | 0 | Random | 94.44 |
| 300 | 66 | 1 | Random | 94.2 |
| 300 | 66 | 2 | Random | 94.9 |
| 300 | 66 | 3 | Random | 94.68 |
| 300 | 66 | 4 | Random | 94.6 |
| 300 | 67 | 0 | Random | 94.3 |
| 300 | 67 | 1 | Random | 94.08 |
| 300 | 67 | 2 | Random | 94.56 |
| 300 | 67 | 3 | Random | 93.78 |
| 300 | 67 | 4 | Random | 94.52 |
| 300 | 68 | 0 | Random | 93.24 |
| 300 | 68 | 1 | Random | 93.76 |
| 300 | 68 | 2 | Random | 94.8 |
| 300 | 68 | 3 | Random | 94.36 |
| 300 | 68 | 4 | Random | 93.76 |
| 300 | 69 | 0 | Random | 94.58 |
| 300 | 69 | 1 | Random | 94.52 |
| 300 | 69 | 2 | Random | 94.72 |
| 300 | 69 | 3 | Random | 94.88 |
| 300 | 69 | 4 | Random | 93.38 |
| 300 | 70 | 0 | Random | 95.34 |
| 300 | 70 | 1 | Random | 94.52 |
| 300 | 70 | 2 | Random | 94.38 |
| 300 | 70 | 3 | Random | 94.94 |
| 300 | 70 | 4 | Random | 93.6 |
| 300 | 71 | 0 | Random | 93.8 |
| 300 | 71 | 1 | Random | 94.38 |
| 300 | 71 | 2 | Random | 94.32 |
| 300 | 71 | 3 | Random | 93.2 |
| 300 | 71 | 4 | Random | 94.28 |
| 300 | 72 | 0 | Random | 94.76 |
| 300 | 72 | 1 | Random | 95 |
| 300 | 72 | 2 | Random | 95.64 |
| 300 | 72 | 3 | Random | 95.28 |
| 300 | 72 | 4 | Random | 95.68 |
| 300 | 73 | 0 | Random | 94.92 |
| 300 | 73 | 1 | Random | 94.52 |
| 300 | 73 | 2 | Random | 94.36 |
| 300 | 73 | 3 | Random | 94.38 |
| 300 | 73 | 4 | Random | 94.56 |
| 300 | 74 | 0 | Random | 94.62 |
| 300 | 74 | 1 | Random | 94.18 |
| 300 | 74 | 2 | Random | 94.38 |
| 300 | 74 | 3 | Random | 94.38 |
| 300 | 74 | 4 | Random | 93.5 |
| 300 | 75 | 0 | Random | 95.32 |
| 300 | 75 | 1 | Random | 95.42 |
| 300 | 75 | 2 | Random | 94.9 |
| 300 | 75 | 3 | Random | 94.96 |
| 300 | 75 | 4 | Random | 94.1 |
| 300 | 76 | 0 | Random | 94.9 |
| 300 | 76 | 1 | Random | 95.46 |
| 300 | 76 | 2 | Random | 94.72 |
| 300 | 76 | 3 | Random | 94.54 |
| 300 | 76 | 4 | Random | 94.16 |
| 300 | 77 | 0 | Random | 94.14 |
| 300 | 77 | 1 | Random | 93.94 |
| 300 | 77 | 2 | Random | 94.28 |
| 300 | 77 | 3 | Random | 94.62 |
| 300 | 77 | 4 | Random | 94.38 |
| 300 | 78 | 0 | Random | 93.8 |
| 300 | 78 | 1 | Random | 93.84 |
| 300 | 78 | 2 | Random | 94.56 |
| 300 | 78 | 3 | Random | 94.18 |
| 300 | 78 | 4 | Random | 93.76 |
| 300 | 79 | 0 | Random | 94.28 |
| 300 | 79 | 1 | Random | 93.66 |
| 300 | 79 | 2 | Random | 93.76 |
| 300 | 79 | 3 | Random | 94.6 |
| 300 | 79 | 4 | Random | 95.76 |
| 300 | 80 | 0 | Random | 94.52 |
| 300 | 80 | 1 | Random | 94.82 |
| 300 | 80 | 2 | Random | 93.82 |
| 300 | 80 | 3 | Random | 94.9 |
| 300 | 80 | 4 | Random | 94.3 |
| 300 | 81 | 0 | Random | 94.84 |
| 300 | 81 | 1 | Random | 94.82 |
| 300 | 81 | 2 | Random | 94.76 |
| 300 | 81 | 3 | Random | 94.54 |
| 300 | 81 | 4 | Random | 94.74 |
| 300 | 82 | 0 | Random | 95.26 |
| 300 | 82 | 1 | Random | 94.32 |
| 300 | 82 | 2 | Random | 94.04 |
| 300 | 82 | 3 | Random | 94.98 |
| 300 | 82 | 4 | Random | 94.56 |
| 300 | 83 | 0 | Random | 94.9 |
| 300 | 83 | 1 | Random | 94.76 |
| 300 | 83 | 2 | Random | 94.06 |
| 300 | 83 | 3 | Random | 94.46 |

TABLE 7B-continued 300 affinity reagents targeting random trimers in the proteome

| Number of Probes | Probe Set ID | Experiment Repetition | Selection Type | Sensitivity |
|---|---|---|---|---|
| 300 | 83 | 4 | Random | 94.8 |
| 300 | 84 | 0 | Random | 93.66 |
| 300 | 84 | 1 | Random | 93.28 |
| 300 | 84 | 2 | Random | 94.64 |
| 300 | 84 | 3 | Random | 93.58 |
| 300 | 84 | 4 | Random | 93.86 |
| 300 | 85 | 0 | Random | 94.16 |
| 300 | 85 | 1 | Random | 93.06 |
| 300 | 85 | 2 | Random | 94.02 |
| 300 | 85 | 3 | Random | 93.1 |
| 300 | 85 | 4 | Random | 94.3 |
| 300 | 86 | 0 | Random | 94.18 |
| 300 | 86 | 1 | Random | 95.02 |
| 300 | 86 | 2 | Random | 93.9 |
| 300 | 86 | 3 | Random | 94.58 |
| 300 | 86 | 4 | Random | 94.8 |
| 300 | 87 | 0 | Random | 95.18 |
| 300 | 87 | 1 | Random | 95.52 |
| 300 | 87 | 2 | Random | 95.38 |
| 300 | 87 | 3 | Random | 95.7 |
| 300 | 87 | 4 | Random | 94.72 |
| 300 | 88 | 0 | Random | 94.52 |
| 300 | 88 | 1 | Random | 93.7 |
| 300 | 88 | 2 | Random | 94.36 |
| 300 | 88 | 3 | Random | 94.14 |
| 300 | 88 | 4 | Random | 95.1 |
| 300 | 89 | 0 | Random | 93.62 |
| 300 | 89 | 1 | Random | 94.8 |
| 300 | 89 | 2 | Random | 94.1 |
| 300 | 89 | 3 | Random | 94.96 |
| 300 | 89 | 4 | Random | 94.68 |
| 300 | 90 | 0 | Random | 94.6 |
| 300 | 90 | 1 | Random | 94.04 |
| 300 | 90 | 2 | Random | 94.14 |
| 300 | 90 | 3 | Random | 94.36 |
| 300 | 90 | 4 | Random | 94.24 |
| 300 | 91 | 0 | Random | 94.12 |
| 300 | 91 | 1 | Random | 94.32 |
| 300 | 91 | 2 | Random | 93.7 |
| 300 | 91 | 3 | Random | 94.56 |
| 300 | 91 | 4 | Random | 94.68 |
| 300 | 92 | 0 | Random | 95.06 |
| 300 | 92 | 1 | Random | 94.06 |
| 300 | 92 | 2 | Random | 95.48 |
| 300 | 92 | 3 | Random | 95.48 |
| 300 | 92 | 4 | Random | 95.24 |
| 300 | 93 | 0 | Random | 93.46 |
| 300 | 93 | 1 | Random | 94.4 |
| 300 | 93 | 2 | Random | 93.62 |
| 300 | 93 | 3 | Random | 94.72 |
| 300 | 93 | 4 | Random | 95.16 |
| 300 | 94 | 0 | Random | 95 |
| 300 | 94 | 1 | Random | 94.74 |
| 300 | 94 | 2 | Random | 94.1 |
| 300 | 94 | 3 | Random | 94.26 |
| 300 | 94 | 4 | Random | 95.02 |
| 300 | 95 | 0 | Random | 94.94 |
| 300 | 95 | 1 | Random | 94.6 |
| 300 | 95 | 2 | Random | 93.9 |
| 300 | 95 | 3 | Random | 95.16 |
| 300 | 95 | 4 | Random | 94.14 |
| 300 | 96 | 0 | Random | 95.08 |
| 300 | 96 | 1 | Random | 94.54 |
| 300 | 96 | 2 | Random | 94.6 |
| 300 | 96 | 3 | Random | 95.14 |
| 300 | 96 | 4 | Random | 93.88 |
| 300 | 97 | 0 | Random | 93.66 |
| 300 | 97 | 1 | Random | 94.32 |
| 300 | 97 | 2 | Random | 93.76 |
| 300 | 97 | 3 | Random | 94.1 |
| 300 | 97 | 4 | Random | 93.64 |
| 300 | 98 | 0 | Random | 95.48 |
| 300 | 98 | 1 | Random | 94.34 |
| 300 | 98 | 2 | Random | 94.96 |
| 300 | 98 | 3 | Random | 94.74 |
| 300 | 98 | 4 | Random | 95.28 |
| 300 | 99 | 0 | Random | 93.86 |
| 300 | 99 | 1 | Random | 94.2 |
| 300 | 99 | 2 | Random | 94.98 |
| 300 | 99 | 3 | Random | 94.38 |
| 300 | 99 | 4 | Random | 94.44 |

TABLE 7C 300 affinity reagents targeting the most-abundant trimers in the proteome

| Number of Probes | Probe Set ID | Experiment Repetitions | Selection Type | Sensitivity |
|---|---|---|---|---|
| 300 | 101 | 0 | Top 300 | 97.98 |
| 300 | 101 | 1 | Top 300 | 97.24 |
| 300 | 101 | 2 | Top 300 | 97.94 |
| 300 | 101 | 3 | Top 300 | 98.18 |
| 300 | 101 | 4 | Top 300 | 97.12 |

Figure 16:
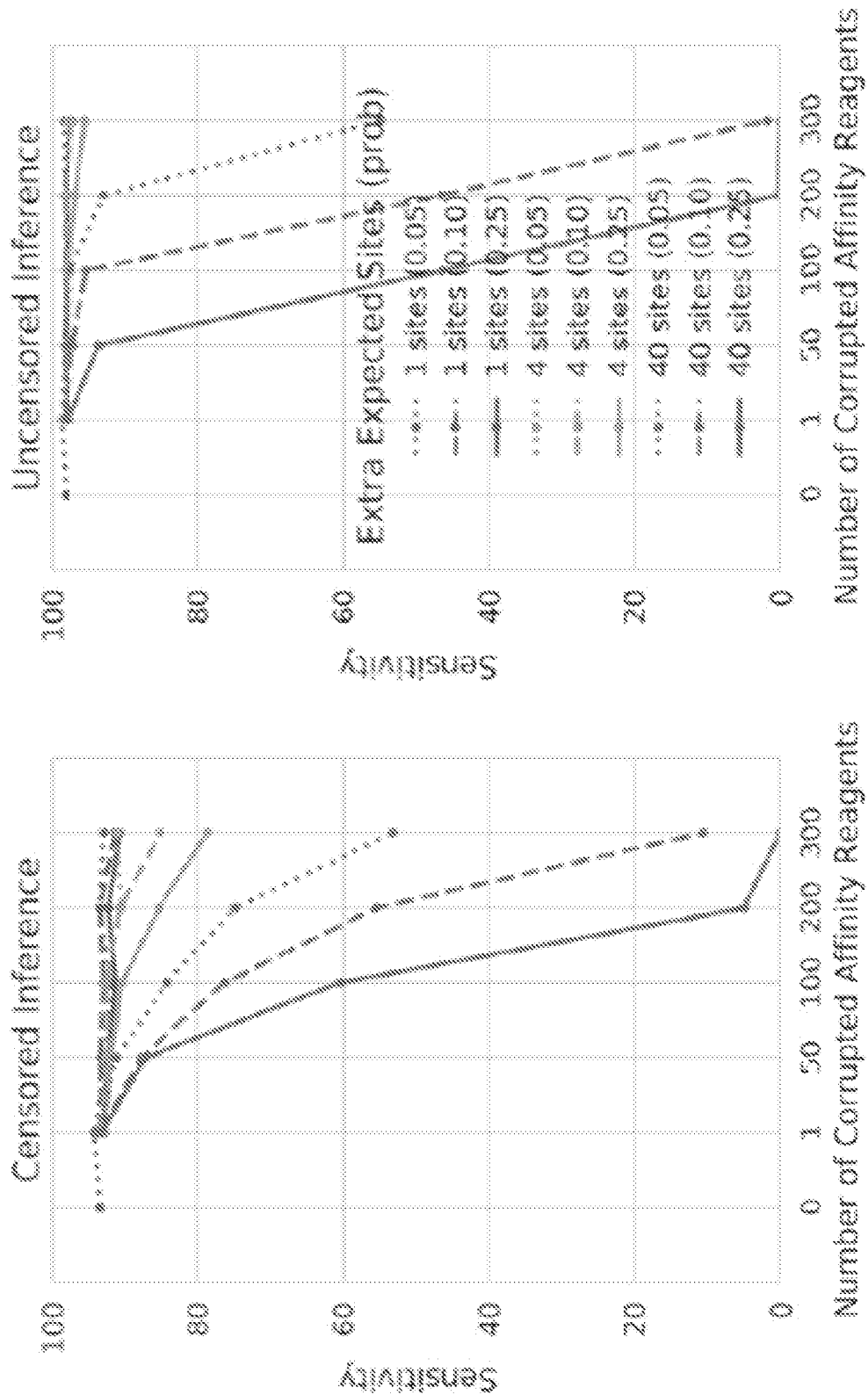
FIG. 16 illustrates the performance of censored protein identification and uncensored protein identification approaches using affinity reagents with missing binding epitopes.

These results are plotted in FIG. 16. In all cases, each affinity reagent had a binding probability of 0.25 to the targeted trimer, and a binding probability of 0.25 to 4 additional randomly selected trimers. The performance of each affinity reagent set is measured based on sensitivity (e.g., the percentage of proteins identified). Each affinity reagent set was assessed in 5 replicates, with the performance of each replicate plotted as a dot, and a vertical line connecting replicate measurements from the same set of affinity reagents. The results from the affinity reagent set consisting of the top 300 most abundant affinity reagents is in blue, the bottom 300 in green. A total of 100 different sets of 300 affinity reagents targeting random trimers were generated and assessed. Each of those sets is represented by a set of 5 grey points (one for each replicate) connected by a vertical grey line. According to the uncensored inference used in this analysis, targeting more abundant trimers improves identification performance as compared to targeting random trimers.

Example 18: Affinity Reagents with Biosimilar Off-Target Sites

The methods described herein may be applied to affinity reagent binding experiment with affinity reagents having different types of off-target binding sites (epitopes). In this example, performance with two classes of affinity reagents are compared: random, and "biosimilar" affinity reagents. The results from these assessments are shown in Tables 8A-8D.

Tables 8A-D

TABLE 8A

Performance of Censored Inference with Affinity Reagents having Biosimilar Off-Target Sites and Targeting the 300 Most-Abundant Trimers in the Proteome

| Censored | Number of Cycles | Probe Type | Sensitivity |
|---|---|---|---|
| TRUE | 100 | Biosimilar | 0.00634 |
| TRUE | 200 | Biosimilar | 31.97667 |
| TRUE | 300 | Biosimilar | 68.73336 |

TABLE 8B

Performance of Uncensored Inference with Affinity Reagents having Biosimilar Off-Target Sites and Targeting the 300 Most-Abundant Trimers in the Proteome

| Censored | Number of Cycles | Probe Type | Sensitivity |
|---|---|---|---|
| FALSE | 100 | Biosimilar | 75.67516 |
| FALSE | 200 | Biosimilar | 97.68607 |
| FALSE | 300 | Biosimilar | 99.06809 |

TABLE 8C

Performance of Censored Inference with Affinity Reagents having Random Off-Target Sites and Targeting the 300 Most-Abundant Trimers in the Proteome

| Censored | Number of Cycles | Probe Type | Sensitivity |
|---|---|---|---|
| TRUE | 100 | Random | 0.082414 |
| TRUE | 200 | Random | 74.68619 |
| TRUE | 300 | Random | 93.13427 |

TABLE 8D

Performance of Uncensored Inference with Affinity Reagents having Random Off-Target Sites and Targeting the 300 Most-Abundant Trimers in the Proteome

| Censored | Number of Cycles | Probe Type | Sensitivity |
|---|---|---|---|
| FALSE | 100 | Random | 60.02916 |
| FALSE | 200 | Random | 95.47356 |
| FALSE | 300 | Random | 98.51021 |

Figure 17:
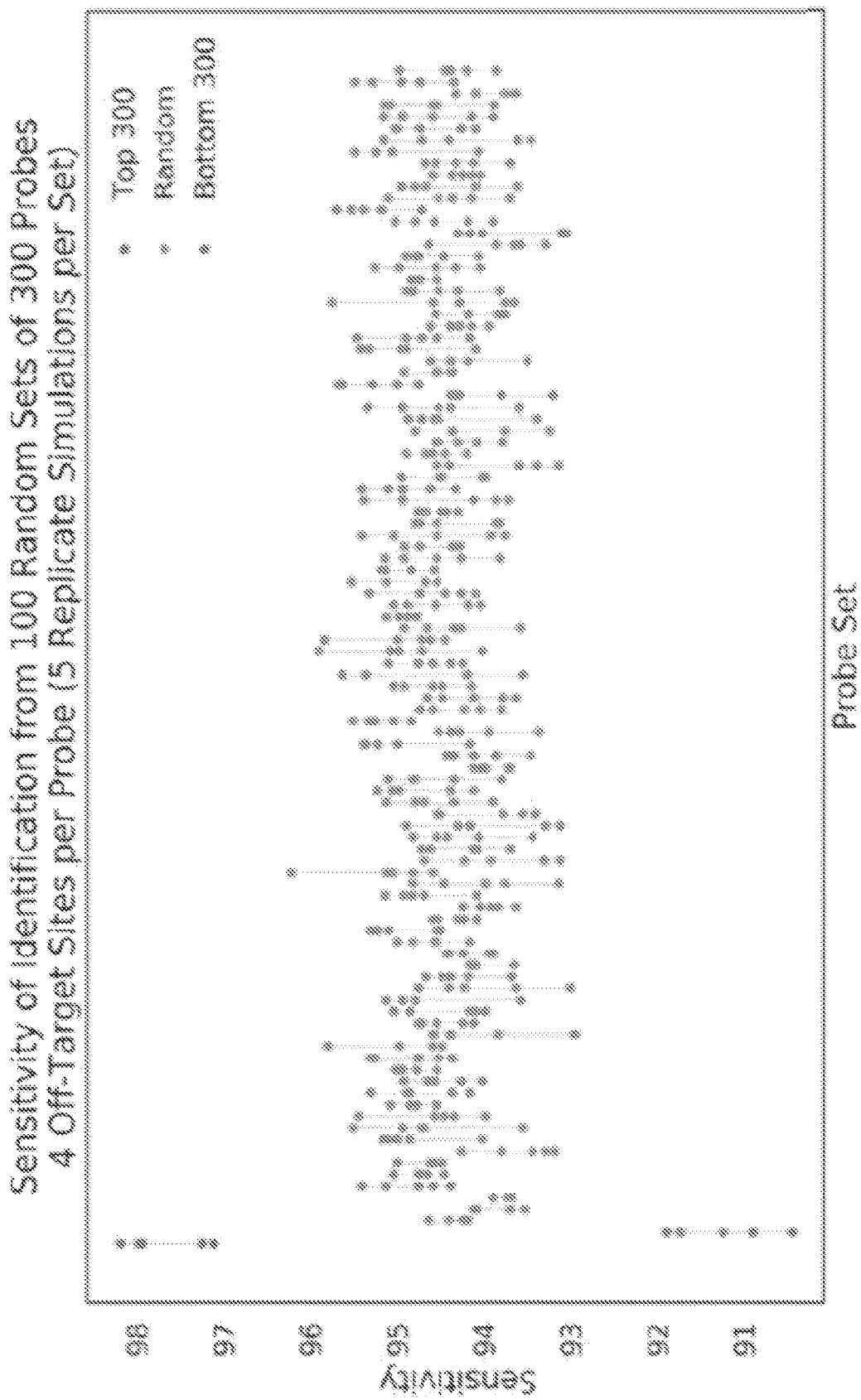
FIG. 17 illustrates the performance of censored protein identification and uncensored protein identification approaches using affinity reagents targeting the top 300 most abundant trimers in the proteome, 300 randomly selected trimers in the proteome, or the 300 least abundant trimers in the proteome.

Unlike the random affinity reagents, the biosimilar affinity reagents have off-target binding sites that are biochemically similar to the targeted epitope. Both the random and biosimilar affinity reagents recognize their target epitope (e.g., a trimer) with binding probability 0.25. Each of the random class of affinity reagents has 4 randomly selected off-target trimer binding sites with binding probability 0.25. In contrast, the 4 off-target binding sites for the "biosimilar" affinity reagents are the four trimers most similar to the trimer targeted by the affinity reagent, which are bound with probability 0.25. For these biosimilar affinity reagents, the similarity between trimer sequences is computed by summing the BLOSUM62 coefficient for the amino acid pair at each sequence location. Both the random and biosimilar affinity reagent sets target the top 300 most abundant trimers in the human proteome, where abundance is measured as the number of unique proteins containing one or more instances of the trimer. FIG. 17 shows the performance of the censored (dashed lines) and uncensored (solid lines) protein inference approaches in terms of the percent of proteins identified in a human sample when affinity reagents with random (blue) or biosimilar (orange) off-target sites are used.

In this comparison, uncensored inference outperforms censored inference, with uncensored inference performing better in the case of biosimilar affinity reagents, and censored inference performing better in the case of random affinity reagents.

Alternatively, rather than using affinity reagents targeting the most abundant trimers in the proteome, an optimal set of trimer targets may be chosen for a particular approach based on the candidate proteins that may be measured (for example, the human proteome), the type of protein inference being performed (censored or uncensored), and the type of affinity reagents being used (random or biosimilar). A "greedy" algorithm, as described below, may be used to select a set of optimal affinity reagents:

1) Initialize an empty list of selected affinity reagents (AR).
2) Initialize a set of candidate ARs (e.g., a collection of 8,000 ARs, each targeting a unique trimer with random off-target sites).
3) Select a set of protein sequences to optimize against (e.g., all human proteins in the Uniprot reference proteome).
4) Repeat the following until the desired number of ARs has been selected:
   a. For each candidate AR:
      i. Simulate binding of the candidate AR against the protein set.
      ii. Perform protein inference for each protein using the simulated binding measurements from the candidate AR and the simulated binding measurements from all previously selected ARs.
      iii. Calculate a score for the candidate AR by summing up the probability of the correct protein identification for each protein determined by protein inference.
   b. Add the AR with the highest score to the set of selected ARs, and remove it from the candidate AR list.

The greedy approach was used to select 300 optimal affinity reagents from either the collection of random affinity reagents or biosimilar affinity reagents targeting the top 4,000 most abundant trimers in the human proteome. The optimization was performed for both censored protein inference and uncensored protein inference. The results from these optimizations are provided in Tables 9A-9D.

TABLE 9A

Performance of Censored Inference with Affinity Reagents having Biosimilar Off-Target Sites and Targeting the 300 Optimal Trimers in the Proteome

| Censored | Number of Cycles | Probe Type | Sensitivity |
|---|---|---|---|
| TRUE | 100 | Biosimilar | 25.58007 |
| TRUE | 200 | Biosimilar | 87.82173 |
| TRUE | 300 | Biosimilar | 95.15025 |

TABLE 9B

Performance of Uncensored Inference with Affinity Reagents having Biosimilar Off-Target Sites and Targeting the 300 Optimal Trimers in the Proteome

| Censored | Number of Cycles | Probe Type | Sensitivity |
|---|---|---|---|
| FALSE | 100 | Biosimilar | 76.76556 |
| FALSE | 200 | Biosimilar | 97.2106 |
| FALSE | 300 | Biosimilar | 99.03005 |

TABLE 9C

Performance of Censored Inference with Affinity Reagents having Random Off-Target Sites and Targeting the 300 Optimal Trimers in the Proteome

| Censored | Number of Cycles | Probe Type | Sensitivity |
|---|---|---|---|
| TRUE | 100 | Random | 24.93343 |
| TRUE | 200 | Random | 88.06263 |
| TRUE | 300 | Random | 95.8476 |

TABLE 9D

Performance of Uncensored Inference with Affinity Reagents having Random Off-Target Sites and Targeting the 300 Optimal Trimers in the Proteome

| Censored | Number of Cycles | Probe Type | Sensitivity |
|---|---|---|---|
| FALSE | 100 | Random | 65.72841 |
| FALSE | 200 | Random | 96.38012 |
| FALSE | 300 | Random | 98.56092 |

Figure 18:
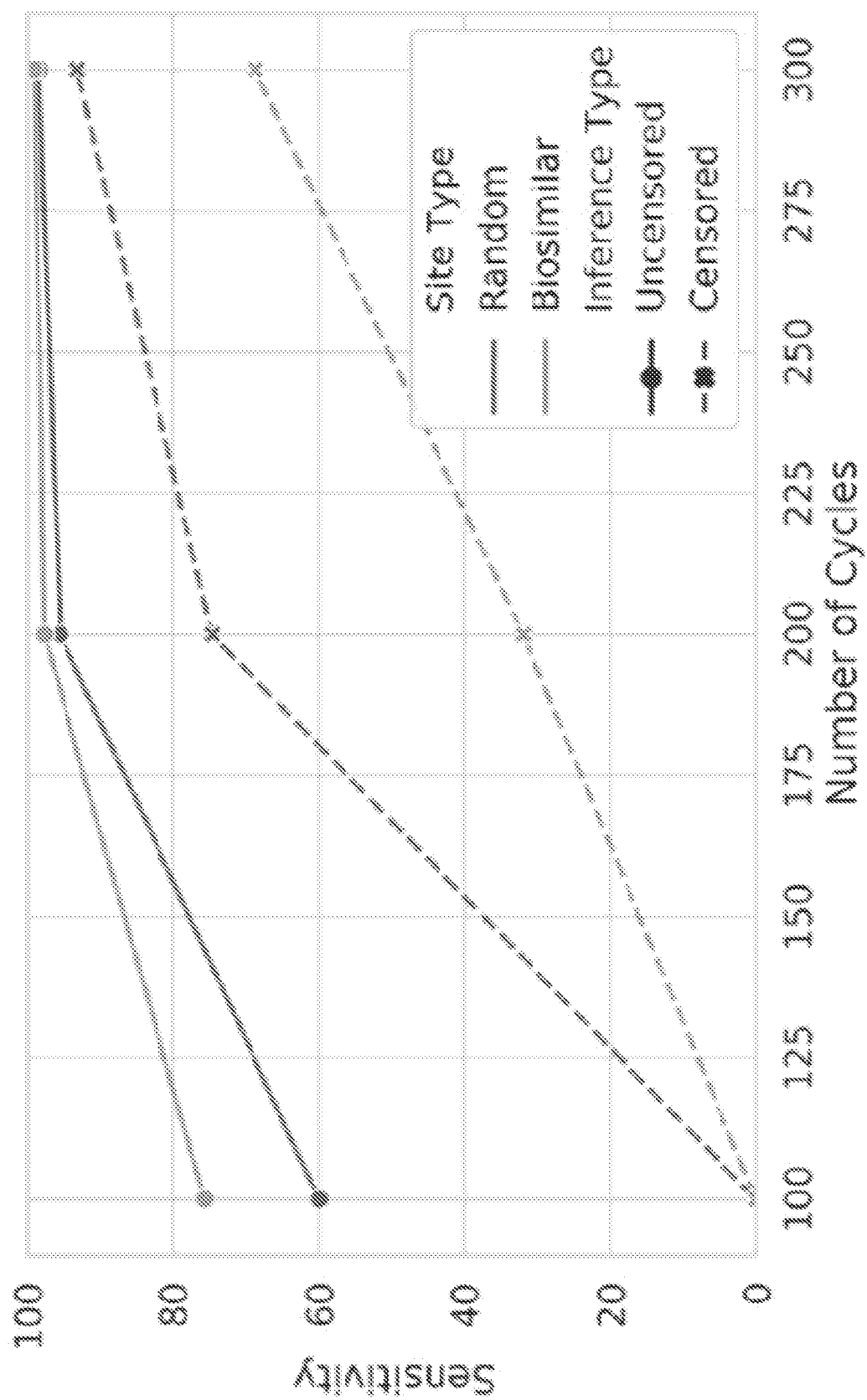
FIG. 18 illustrates the performance of censored protein identification and uncensored protein identification approaches using affinity reagents with random or biosimilar off-target sites.

The performance of the optimized probe sets for both censored protein inference and uncensored protein inference are plotted in FIG. 18.

Using the set of affinity reagents selected by the greedy optimization algorithm improves the performance of both random and biosimilar affinity reagent sets using both censored protein inference and uncensored protein inference approaches. Additionally, random affinity reagents sets perform almost identically to biosimilar affinity reagents sets when the greedy approach is used to select affinity reagents.

Example 19: Protein Inference Using Binding of Mixtures of Affinity Reagents The methods described herein may be applied to analyze and/or identify proteins that have been measured using mixtures of affinity reagents. The probability of a specific protein generating a binding outcome when assayed by a mixture of affinity reagents may be computed as follows:

1) Calculate $\overline{p_{ns}}$, the average probability of non-specific epitope binding of each affinity reagent in the mixture.
2) Calculate the number of binding sites on the protein based on the length of the protein (L) and the length of the affinity reagent epitopes (K): Num binding sites=L−K+1. The probability of no non-specific binding events occurring is $(1-\overline{p_{ns}})^{L-K+1}$.
3) For each affinity reagent in the mixture, calculate the probability of no epitope-specific binding events occurring:

$$P\_no\_spec\_bind(AR) = \prod_{epitope} (1 - epitope\ binding\ probability)^{epitope\ count\ in\ protein}$$

4) The probability of the mixture generating a non-binding outcome for the protein is:

$$P(\text{no bind} | \text{protein}) = (1 - \overline{p_{ns}})^{L-K+1} \prod_{AR} P\_no\_spec\_bind(AR)$$

5) The probability of the mixture generating a binding outcome is:

$$P(\text{bind}|\text{protein}) = 1 - P(\text{no bind}|\text{protein})$$

This approach for calculating the probability of a binding or non-binding outcome from a protein mixture was used in combination with the methods described herein to analyze the performance of mixtures of affinity reagents for protein identification. Each individual affinity reagent in the analysis binds to its targeted trimer epitope with a probability of 0.25 and the 4 most similar trimers to that epitope target with a probability of 0.25. For these affinity reagents, trimer similarity is calculated by summing the coefficients from the BLOSUM62 substitution matrix for the amino acids at each sequence location in the trimers being compared. Additionally, each affinity reagent binds 20 additional off-target sites with binding probability scaled depending on the sequence similarity between the off-target site and the targeted trimer calculated using the BLOSUM62 substitution matrix. The probability for these additional off target sites is: $0.25*1.5^{S_{OT}-S_{self}}$ where $S_{OT}$ is the BLOSUM62 similarity between the off-target site and the targeted site, and $S_{self}$ is the BLOSUM62 similarity between the targeted sequence and itself. Any off-target sites with binding probability below $2.45 \times 10^8$ are adjusted to have binding probability $2.45 \times 10^8$. The non-specific epitope binding probability is $2.45 \times 10^8$ in this example.

An optimal set of 300 mixtures of affinity reagents were generated for both censored and uncensored protein inference using a greedy approach:

1) Initialize an empty list of selected affinity reagent (AR) mixtures.
2) Initialize a list of candidate affinity reagents (in this example, consisting of the 300 most optimal computed using the greedy approach detailed in Example 18).
3) Select a set of protein sequences to optimize against (e.g., all human proteins in the Uniprot reference proteome).
4) Repeat the following until the desired number of AR mixtures has been generated:
   a. Initialize an empty mixture.
   b. For each candidate AR:
      i. Simulate binding outcomes using the current mixture with the candidate AR added to it.
      ii. Perform protein inference for each protein using the simulated binding measurements from i. and simulated binding measurements from previously generated mixtures.
      iii. Calculate a score for the mixture with this candidate AR by summing up the probability of the correct protein identification for each protein as determined by protein inference.
   c. Add the highest scoring candidate AR to the mixture.

d. For each candidate AR not already in the mixture, score the mixture with the addition of the AR, as in i-iii, and if the highest scoring candidate has a higher score than the previous candidate added to the mixture, add it to the mixture and repeat this step. The mixture is complete when the best scoring candidate AR reduces the score of the mixture relative to the previously added candidate or when all candidate ARs have been added to the mixture.

Figure 19:
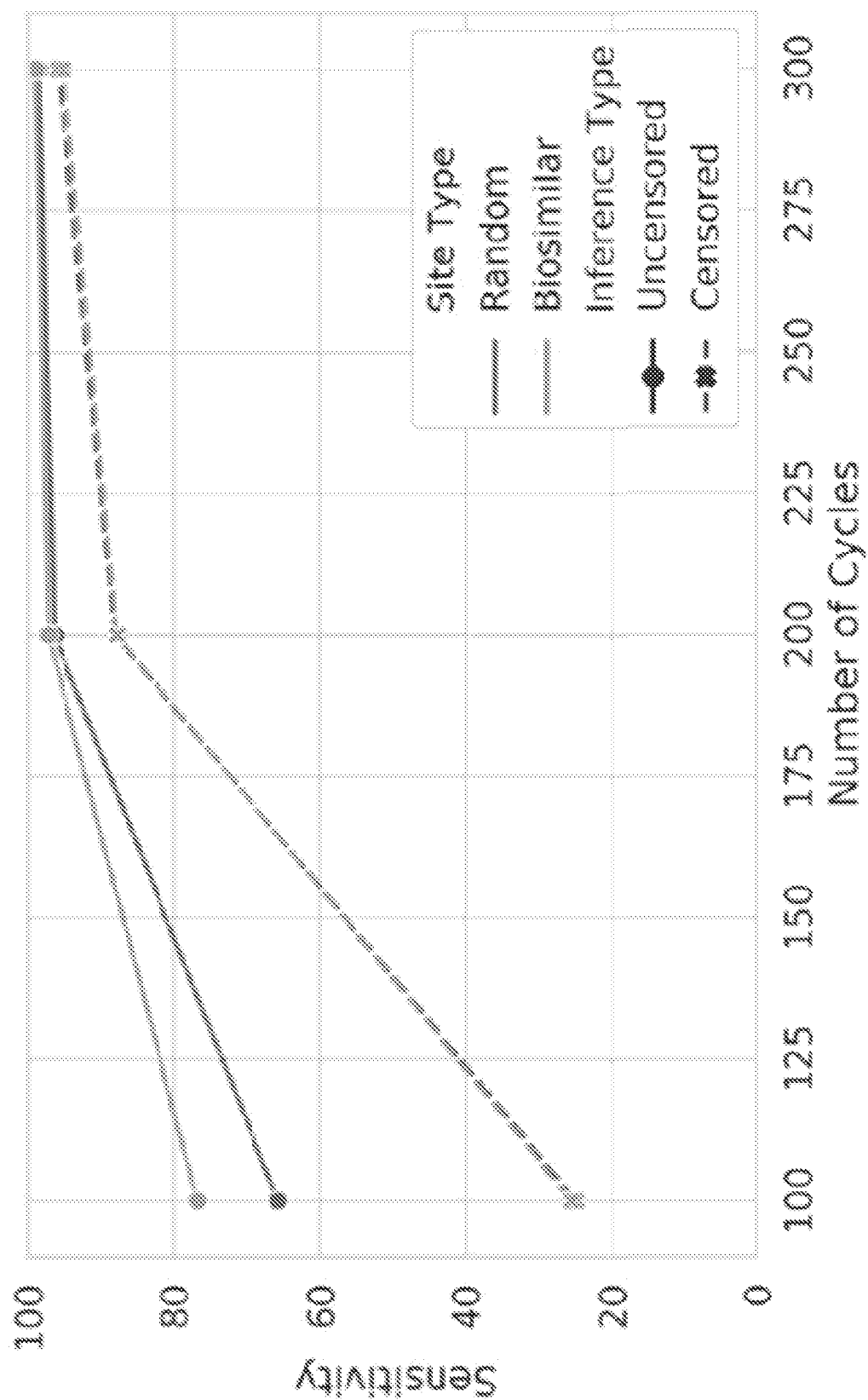
FIG. 19 illustrates the performance of censored protein identification and uncensored protein identification approaches using a set of optimal affinity reagents (probes).
Figure 20:
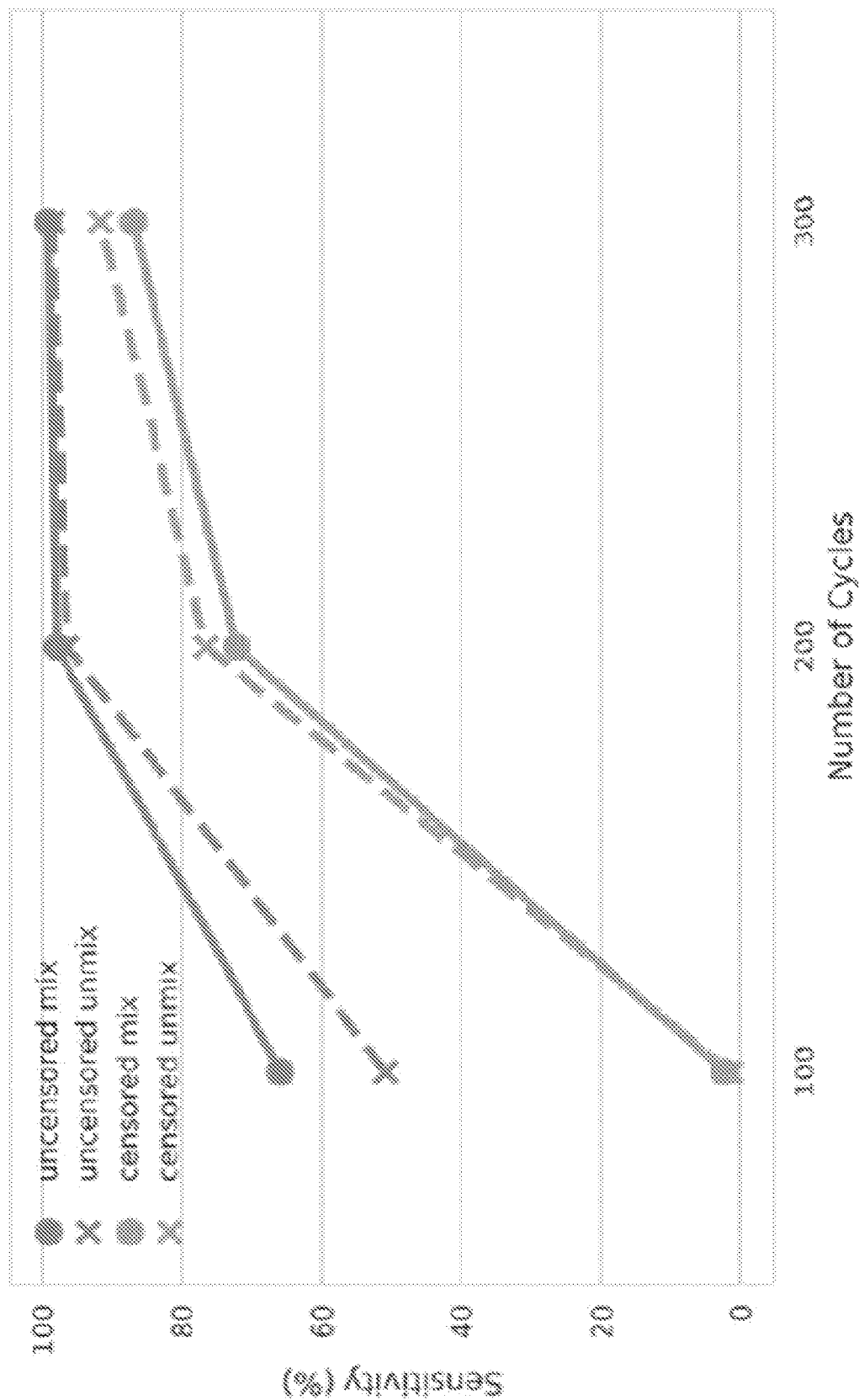
FIG. 20 illustrates the performance of censored protein identification and uncensored protein identification approaches using unmixed candidate affinity reagents and mixtures of candidate affinity reagents.

FIG. 19 shows the protein identification sensitivity when the unmixed candidate affinity reagents are used with censored protein inference and uncensored protein inference, and when mixtures are used. The data plotted in FIG. 19 is shown in Tables 10A-10B.

Tables 10A-B

TABLE 10A

Performance of Censored Inference with Measurements Made on Individual Probe Binding (unmix) or Mixtures of Probes (mix)

| Censored | Mix Type | Number of Cycles | Probe Type | Sensitivity |
|---|---|---|---|---|
| TRUE | mix | 100 | Biosimilar | 2.244199 |
| TRUE | unmix | 100 | Biosimilar | 1.363002 |
| TRUE | mix | 200 | Biosimilar | 72.16939 |
| TRUE | unmix | 200 | Biosimilar | 76.51198 |
| TRUE | mix | 300 | Biosimilar | 86.91518 |
| TRUE | unmix | 300 | Biosimilar | 91.5684 |

TABLE 10B

Performance of Uncensored Inference with Measurements Made on Individual Probe Binding (unmix) or Mixtures of Probes (mix)

| Censored | Mix Type | Number of Cycles | Probe Type | Sensitivity |
|---|---|---|---|---|
| FALSE | mix | 100 | Biosimilar | 65.76011 |
| FALSE | unmix | 100 | Biosimilar | 50.79244 |
| FALSE | mix | 200 | Biosimilar | 97.81286 |
| FALSE | unmix | 200 | Biosimilar | 96.30404 |
| FALSE | mix | 300 | Biosimilar | 99.14416 |
| FALSE | unmix | 300 | Biosimilar | 98.56726 |

The use of mixtures improves performance when uncensored inference is used but may negatively impact performance if censored inference is used.

Example 20—Glycan Identification with a Database of 7 Candidate Glycans

Consider a situation where a database contains 7 candidate glycans:

| ID | Structure |
|---|---|
| 19 | Galb1-4GlcNAcb1-6(Galb1-4GlcNAcb1-3)GalNAc |
| 52 | GlcNAcb1-2Mana1-6(GlcNAcb1-2Mana1-3)Manb1-4GlcNAcb1-4GlcNAc |
| 344 | GlcNAca1-4Galb1-3 GalNAc |
| 378 | Neu5Aca2-3Galb1-4(Fuca1-3)GlcNAcb1-3GalNAc |
| 430 | Fuca1-3GlcNAcb1-6(Galb1-4GlcNAcb1-3)Galb1-4Glc |
| 519 | GalNAca1-3(Fuca1-2)Galb1-4GlcNAcb1-6GalNAc |
| 534 | Neu5Aca2-3Galb1-4(Fuca1-3)GlcNAcb1-2Man |

Additionally, the experiment is performed with 4 affinity reagents (AR), each of which has a 25% likelihood of binding a given disaccharide. The other disaccharides these reagents bind to are not found in any glycan in the database.

A hit table is constructed for the affinity reagents to each sequence in the database (Row=affinity reagents #1 to #4, Col=SEQ TD)

| AR Target | 19 | 52 | 344 | 378 | 430 | 519 | 534 |
|---|---|---|---|---|---|---|---|
| Neu5Aca2-3Gal | | | | 1 | | | 1 |
| GlcNAcb1-2Man | | 2 | | | | | 1 |
| Fuca1-3GlcNAc | | | | 1 | 1 | | 1 |
| Galb1-4GlcNAc | 2 | | | 1 | 1 | 1 | 1 |

Notably, this information arrives incrementally, and therefore may be computed iteratively. From the hit table, P(glycan_i|AR_j) is evaluated to generate a probability matrix, as shown below. Note that for a given entry, if hit table ≥1, then use P_landing_AR_n=true landing rate=0.25; else if hit table=0, use_P(detector error)=_0.00001.

| | 19 | 52 | 344 | 378 | 430 | 519 | 534 |
|---|---|---|---|---|---|---|---|
| Neu5Aca2-3Gal | 1.00E−05 | 1.00E−05 | 1.00E−05 | 0.25 | 1.00E−05 | 1.00E−05 | 0.25 |
| GlcNAcb1-2Man | 1.00E−05 | 0.25 | 1.00E−05 | 1.00E−05 | 1.00E−05 | 1.00E−05 | 0.25 |
| Fuca1-3GlcNAc | 1.00E−05 | 1.00E−05 | 1.00E−05 | 0.25 | 0.25 | 1.00E−05 | 0.25 |
| Galb1-4GlcNAc | 0.25 | 1.00E−05 | 1.00E−05 | 0.25 | 0.25 | 0.25 | 0.25 |

Note that many of the cells contain a 0.00001 probability. This small probability accounts for possible detector error. The initial, un-normalized probability of a glycan is calculated as the product of the probabilities for each candidate glycan:

| 19 | 52 | 344 | 378 | 430 | 519 | 534 |
|---|---|---|---|---|---|---|
| 2.5E−16 | 2.5E−16 | 1E−20 | 1.5625E−07 | 6.25E−12 | 2.5E−16 | 0.00390625 |

Next, the size normalization is computed, which refers to the number of ways some number of affinity reagents may land on a given glycan, as a function of the number of potential binding sites of the glycan. The size normalization is given by the Choose(sites_i, n) term. For example, candidate ID 52 has 6 disaccharide sites and a size normalization of [6 choose 4] which is 15. If there are more binding events than the number of available disaccharide sites, the size normalization factor is set to 1. The un-normalized probabilities of each glycan are normalized to take into account this size correction by dividing by the size normalization which gives:

| 19 | 52 | 344 | 378 | 430 | 519 | 534 |
|---|---|---|---|---|---|---|
| 2.5E−16 | 1.6667E−17 | 1E−20 | 1.5625E−07 | 1.25E−12 | 2.5E−16 | 0.00390625 |

Next, the probabilities are normalized such that the entire set of probabilities over the entire database sums up to one. This is achieved by summing the size-normalized probabilities to 0.00390641 and dividing each of the size-normalized probabilities by this normalization to achieve the final balanced probabilities:

| 19 | 52 | 344 | 378 | 430 | 519 | 534 |
|---|---|---|---|---|---|---|
| 6.39974E−14 | 4.2665E−15 | 2.5599E−18 | 3.9998E−05 | 3.1999E−10 | 6.3997E−14 | 0.99996 |

Example 21: Performance of Censored Protein Identification in Samples Containing Protein Isoforms The protein identification approaches described herein may be applied to samples containing protein isoforms. An isoform of a canonical protein may refer to a variant of the canonical protein formed by alternative splicing of the same gene as the canonical protein or another gene in the same gene family as the canonical protein. A protein isoform may be structurally similar to the canonical protein, typically sharing large portions of sequence with the canonical protein.

Protein Sample and Affinity Reagents

To determine the impact of the presence of isoform sequences on protein identification, an affinity reagent binding analysis was performed on a collection of proteins consisting of 20,374 unique canonical human proteins and 21,987 unique isoforms of those canonical proteins. The canonical proteins and isoform proteins are those listed in the reference human proteome available as part of the Uniprot database. Only proteins with the "Swiss-Prot" designation, used to designate proteins that have been manually annotated and reviewed, were included in the analysis. The number of isoforms included for each individual canonical protein ranged from 0 to 36 isoforms. The mean number of isoforms for a canonical protein in this set is 1.08. The sample was analyzed using 384 affinity reagent cycles, each cycle measuring binding outcomes of a unique affinity reagent to each of the proteins in the sample. Each affinity reagent binds a targeted trimer with a probability of 0.25, and to the four trimers most similar to the targeted trimer with a probability of 0.25. Other off-target trimers are bound with a probability of the greater of the quantities $2.45 \times 10^{-8}$ and $0.25 \cdot 1.5^{-x}$ where x is the similarity of the off-target trimer to the trimer target subtracted from the similarity of the targeted trimer to itself. The similarity between trimer sequences can be computed by, for example, summing the BLOSUM62 coefficient for the amino acid pair at each of the three sequence locations. Affinity reagent trimer targets were selected using a greedy approach, as described in Example 18, to optimize against the human proteome.

Protein Identification Performance Using Unknown Isoform Sequences

Censored protein inference was performed on the binding outcomes from the sample using a database containing only the sequences for the 20,374 canonical proteins in the protein sample. Because the database used for protein inference is missing the sequences of the 21,987 protein isoforms in the sample, the results of this analysis indicate performance when the sequences of potential protein isoforms in a sample are not known. With protein inference performed in this manner, the correct protein family is identified for 83.9% of the proteins in the sample with a false discovery rate of 1%. The term "protein family," as used herein, generally refers to a set of sequences including a canonical protein sequence and all isoforms of that canonical protein sequence. The correct protein family for a protein is identified if the inferred protein identity is within the same protein family as the protein being analyzed.

Protein Identification Performance Using Known Isoform Sequences

When protein inference was performed using a sequence database consisting of all of the protein sequences in the sample (both canonical protein sequences and isoform protein sequences), the correct protein sequence was identified for 60.9% of the proteins in the sample with a false discovery rate of 1%. The correct protein sequence is identified for a protein if the exact sequence for the protein is identified. Further, the correct protein family is identified for 89.8% of the proteins in the sample. The discrepancy between the identification rate of protein families and of exact protein sequences may arise due to the difficulty of resolving the identity of a protein between multiple isoform candidates having similar sequences.

Protein Identification Performance Using Protein Families Defined a Priori

When the grouping of canonical protein sequences and isoform protein sequences into protein families is known a priori, the identification rate for protein families may be improved by calculating protein family probabilities directly. For an individual protein being measured, the probability of the protein being a member of the protein family may be calculated by summing each of the probabilities of the individual protein sequences comprising the family. The protein family with the highest probability for the protein being analyzed is assigned as the protein family identification. When protein family probabilities are calculated in this manner, the correct protein family is identified for 97.2% of the proteins in the sample at 1% false discovery rate. In comparison, the correct protein family is identified for 89.8% of the proteins in the sample at 1% false discovery rate, when the protein family probabilities are not directly calculated.

Example 22: Performance of Censored Protein Identification in Samples Containing Proteins with Single Amino Acid Variants (SAVs)

The protein identification approaches described herein may be applied to samples containing proteins with single amino acid variants. A single amino acid variant (SAV) of a canonical protein, as used herein, generally refers to a variant of the canonical protein which differs by a single amino acid. Single amino acid variant proteins may typically arise from missense single nucleotide polymorphisms (SNPs) in the gene encoding the protein.

Protein Sample and Affinity Reagents

To determine the impact of the presence of SAV proteins on protein identification, an affinity reagent binding analysis was performed on a collection of proteins consisting of 20,374 unique canonical human proteins and 12,827 unique SAVs of those canonical proteins. The canonical proteins are those listed in the reference human proteome available as part of the Uniprot database. For each canonical protein, if one or more SAVs for the protein exist in the SAV database, a randomly chosen SAV is included in the sample. The SAV database used is the Uniprot human polymorphisms and disease mutations index. Only proteins with the "Swiss-Prot" designation, used to designate proteins that have been manually annotated and reviewed, were included in the analysis. The sample was analyzed using 384 affinity reagent cycles, each cycle measuring binding outcomes of a unique affinity reagent to each of the proteins in the sample. Each affinity reagent binds a targeted trimer with a probability of 0.25, and to the four trimers most similar to the targeted trimer with a probability of 0.25. Other off-target trimers are bound with a probability of the greater of the quantities $2.45 \times 10^{-8}$ and $0.25 * 1.5^{-x}$ where x is the similarity of the off-target trimer to the trimer target subtracted from the similarity of the targeted trimer to itself. The similarity between trimer sequences may be computed by, for example, summing the BLOSUM62 coefficient for the amino acid pair at each of the three sequence locations. Affinity reagent trimer targets were selected using a greedy approach, as described in Example 18, to optimize against the human proteome.

Protein Identification Performance Using Known SAV Sequences

Censored protein inference was performed on the binding outcomes from the sample using a database containing only the sequences for the 20,374 canonical proteins in the protein sample. Because the database used for protein inference is missing the sequences of the 12,827 SAV proteins in the sample, the results of this analysis indicate performance when the sequences of all potential SAVs in a sample are not known. With protein inference performed in this manner, the correct SAV protein family is identified for 96.0% of the proteins in the sample with a false discovery rate of 1%. The term "SAV protein family," as used herein, generally refers to set of sequences including a canonical protein sequence and all SAVs of that canonical protein sequence. The correct SAV protein family for a protein is identified if the inferred protein identity is within the same SAV protein family as the protein being analyzed.

Protein Identification Performance Using Known SAV Sequences

When protein inference was performed using a sequence database consisting of all of the protein sequences in the sample (both canonical protein sequences and SAV protein sequences), the correct protein sequence was identified for 27.1% of the proteins in the sample with a false discovery rate of 1%. The correct protein sequence is identified for a protein if the exact sequence for the protein is identified. Further, the correct SAV protein family is identified for 96.1% of the proteins in the sample. The discrepancy between the identification rate of SAV protein families and of exact protein sequences may arise due to the difficulty of resolving between the identities of a canonical protein sequence and of an extremely similar SAV sequence.

Protein Identification Performance Using SAV Protein Families Defined a Priori

The identification rate for SAV protein families may be improved by calculating SAV protein family probabilities directly. For an individual protein being measured, the probability of the protein being a member of a SAV protein family may be calculated by summing each of the probabilities of the individual protein sequences comprising the family. The SAV protein family with the highest probability for the protein being analyzed is assigned as the SAV protein family identification. When SAV protein family probabilities are calculated in this manner, the correct SAV protein family is identified for 96.5% of the proteins in the sample at 1% false discovery rate. In comparison, the correct SAV protein family is identified for 96.1% of the proteins in the sample at 1% false discovery rate when the protein family probabilities are not directly calculated.

Example 23: Performance of Censored Protein Inference on a Sample Containing Proteins from a Mixture of Species In some cases, a protein sample may comprise proteins from each of a plurality of species. A protein sample may contain proteins arising from external sources such as fossils. In some embodiments, a protein sample may contain proteins that are synthesized, modified, or engineered, such as a recombinant protein, or a protein synthesized by in-vitro transcription and translation. In some embodiments, synthesized, modified, or engineered proteins may contain non-natural sequences (e.g., arising from CRISPR-Cas9 modification or other artificial gene constructs). Each of the species may be, for example, an animal such as a mammal (e.g., human, mouse, rat, primate, or simian), farm animals (production cattle, dairy cattle, poultry, horses, pigs, and the like), sport animals, companion animals (e.g., pet or support animals); a plant, a protist, a bacterium, a virus, or an archeon.

In this example, a sample from a mouse tumor xenograft model may comprise substantial amounts of proteins of both mouse and human origin. To determine the performance of protein inference on a sample having proteins from a mixture of species on protein inference, an affinity reagent binding analysis was performed on a collection of proteins consisting of 2,000 unique mouse proteins and 2,000 unique human proteins. Both the human proteins and the mouse proteins were randomly selected from the collection of canonical Swiss-Prot sequence entries in the Uniprot reference proteome of the respective species. The sample was analyzed using 384 affinity reagent cycles, each cycle measuring binding outcomes of a unique affinity reagent to each of the proteins in the sample. Each affinity reagent binds a targeted trimer with a probability of 0.25, and to the four trimers most similar to the targeted trimer with a probability of 0.25. Other off-target trimers are bound with probability the greater of the quantities $2.45 \times 10^{-8}$ and $0.25*1.5^{-x}$ where x is the similarity of the off-target trimer to the trimer target subtracted from the similarity of the targeted trimer to itself. The similarity between trimer sequences may be computed by, for example, summing the BLOSUM62 coefficient for the amino acid pair at each of the three sequence locations. Affinity reagent trimer targets were selected using a greedy approach, as described in Example 18, to optimize against the human proteome.

When protein inference was performed on the mixture sample using a database containing only the sequences for the candidate proteins from the human proteome (canonical Swiss-Prot sequence entries in the Uniprot human reference proteome), the results showed no identifications of proteins in the sample (e.g., an identification rate of 0%) below a 1% false discovery rate threshold. In comparison, when protein inference was performed on the mixture sample using a database containing the sequences for the candidate proteins from both the human proteome and the mouse proteome, 85.3% of the proteins in the sample were identified below a 1% false discovery rate threshold. This discrepancy in performance indicates that for a sample containing proteins from multiple species (e.g., a mixture sample), protein identification performance is significantly improved when protein inference analysis is performed using a database containing the sequences for the candidate proteins from all of the species represented in the mixture sample.

Example 24: Design of an Affinity Reagent Set Against a Targeted Panel of Proteins A set of affinity reagents may be designed that is optimized for identification of a specific subset of proteins in a sample. For example, an optimal collection of affinity reagents can be used to identify a specific set of target proteins in fewer affinity reagent binding cycles as compared to using a set optimized for identification of the entire proteome. In this example, a set of affinity reagents is generated for optimal identification of 25 human proteins, which are potential biomarkers for clinical response to cancer immunotherapy treatment. The proteins in the targeted panel are listed in Table 11.

TABLE 11

Proteins Included in the Targeted Panel for Response to Cancer Immunotherapy

| Category | Gene | Uniprot Accessions |
|---|---|---|
| T cell surface markers | CD8A | P01732 |
| | CD3 | P07766; P09693; P20963; P04234 |
| | CD2 | P06729 |
| | CD38 | P28907 |
| Cytotoxic factors | PRF1 | P14222 |
| | GZMB | P10144 |
| Tissue rejection-related cytokines and chemokines | CXCL9 | Q07325 |
| | CXCL10 | P02778 |
| | CXCL2 | P19875 |
| | CXCL11 | O14625 |
| | CCL4 | P13236 |
| | CCL5 | P13501 |
| | GZMK | P49863 |
| PD-1/immune checkpoints | PD-L1 | Q9NZQ7 |
| | JAK2 | O60674 |
| | PD-L2 | Q9BQ51 |

TABLE 11-continued

Proteins Included in the Targeted Panel for Response to Cancer Immunotherapy

| Category | Gene | Uniprot Accessions |
|---|---|---|
| | PD-1 | Q15116 |
| | CTLA4 | P16410 |
| Increased type 1 immunity & cytotoxic cell activity | IFNG | P01579 |
| Interleukins | IL-12 | P29459; P29460 |
| | IL-2 | P60568 |

To generate a set of affinity reagents optimized for identification of the complete proteome, a greedy selection approach, as described in Example 18, was applied. This set of affinity reagents can be referred to as the "proteome-optimized" affinity reagent set. To generate a set of affinity reagents optimized for identification of the proteins in Table 11, a modified version of step 4) i) in Example 18 is performed, in which, rather than calculating the score for the candidate affinity reagent by summing each of the probabilities of the correct protein identification for each protein determined by protein inference, the score for the candidate affinity reagent is calculated by summing each of the probabilities of the correct protein identification for only the proteins in the targeted panel. This affinity reagent set can be referred to as the "panel-optimized" affinity reagent set. The performance of the proteome-optimized and panel-optimized affinity reagent sets were tested on a human proteome sample containing every unique, canonical protein in the Swiss-Prot human reference proteome from Uniprot (20,374 proteins). This sample includes all 25 of the proteins in the target panel. Both affinity reagents sets were used to analyze the protein sample, and censored inference used to generate protein identifications for every protein in the sample.

The number of targeted panel proteins identified by the proteome-optimized and panel-optimized affinity reagent sets is indicated in Table 12. For a targeted panel protein to be counted as a successful identification, it must be present in the list of all proteins identified in the sample at a false discovery rate below 1%. Identification was performed with varying number of affinity reagent cycles. For example, 150 affinity reagent cycles indicates that protein inference was performed on a dataset comprising analysis with the first 150 affinity reagents from either the proteome-optimized or panel-optimized set, with each affinity reagent analyzed in an individual cycle.

TABLE 12

Protein Identification Performance for Target Panel of 25 Target Proteins

| Number of Affinity Reagent Cycles | Target Panel Proteins Identified (Proteome-Optimized Reagents) | Target Panel Proteins Identified (Panel-Optimized Reagents) |
|---|---|---|
| 50 | 0 | 0 |
| 100 | 1 | 3 |
| 150 | 10 | 9 |
| 200 | 18 | 19 |
| 250 | 19 | 24 |
| 300 | 20 | 24 |
| 350 | 22 | 24 |
| 384 | 23 | 24 |

The results shown in Table 12 indicate that application of the panel-optimized affinity reagents successfully increased the identification rate of the targeted panel proteins. The percentage of all proteins identified at a false discovery rate below 1% for both the panel-optimized and proteome-optimized affinity reagent sets are indicated in Table 13.

TABLE 13

Protein Identification Performance for All Proteins in the Sample

| Number of Affinity Reagent Cycles | % of Proteins Identified in Sample (Proteome-Optimized Reagents) | % of Proteins Identified in Sample (Panel-Optimized Reagents) |
| --- | --- | --- |
| 50 | 0 | 0 |
| 100 | 3.1 | 0.1 |
| 150 | 43.4 | 4.7 |
| 200 | 78.9 | 34.4 |
| 250 | 89.2 | 65.6 |
| 300 | 93.0 | 77.5 |
| 350 | 94.8 | 84.2 |
| 384 | 95.7 | 87.0 |

The results shown in Table 13 indicate that a panel-optimized affinity reagent set can be generated to improve the performance of identifying a set of proteins in a specific targeted panel. However, a tradeoff may be encountered, wherein the resulting panel-optimized affinity reagent set may be sub-optimal for identifying proteins outside of the targeted panel, as indicated by the decreased overall protein identification rate of the panel-optimized reagents in Table 13.

Example 25: Performance of Protein Inference Using Detection of Presence, Count, or Order of Individual Amino Acids The protein inference approach described herein may be applied to measurements of specific amino acids in proteins and peptides. For example, measurements on a protein may be made which indicate the presence or absence of an amino acid in a protein or peptide (binary), the count of an amino acid in a protein or peptide (count), or the order of amino acids in a protein (order). In this example, proteins are modified by a series of reactions which each selectively modify a particular amino acid. Each reaction of the series of reactions has a reaction efficiency between 0 and 1, indicating the probability of the reaction successfully modifying any single amino acid substrate within the protein. After performing such modification reactions on the protein sample, the presence or absence of a selectively-modified amino acid may be detected, the count of a selectively-modified amino acid may be detected, and/or the order of a particular set of selectively-modified amino acids within the protein may be detected.

Detections from Presence and Absence Measurements of Amino Acids

To generate protein identifications from a sequence of binary measurements indicating presence or absence of amino acids, the probability Pr(amino acid detected present|protein) can be expressed as $1-(1-R_{aa})^{Caa}$ where $R_{aa}$ is the reaction efficiency for the amino acid and Caa is the count of the number of times the amino acid occurs in the protein. The probability Pr(amino acid not detected present|protein) can be expressed as 1−Pr(amino acid detected present|protein). If a sequence of multiple amino acid detection measurements is made, the probabilities may be multiplied to determine the probability of the complete set of N measurements given a candidate protein, as expressed by:

Pr(outcome set|protein)=Pr(measurement outcome for amino acid 1|protein)*Pr(measurement outcome for amino acid 2|protein)* . . . Pr(measurement outcome for amino acid N|protein).

The probability of a particular candidate protein being the correct identification for the protein being measured can be expressed as $$\frac{Pr(\text{outcome set} \mid \text{candidate protein})}{\sum_{i=1}^{P} Pr(\text{outcome set} \mid protein_i)}$$

where $\sum_{i=1}^{P} Pr(\text{outcome set}|protein_i)$ is the sum of the probabilities of the outcome set for each possible protein in the protein sequence database consisting of P proteins.

Detections from Count Measurements of Amino Acids

To generate protein identifications from a sequence of count measurements of amino acids, the probability Pr(amino acid count measurement|protein) can be expressed as $$(R_{aa})^M * (1 - R_{aa})^{Caa-M} * \binom{Caa}{M}$$

where $R_{aa}$ is the reaction efficiency for the amino acid, Caa is the count of the number of times the amino acid occurs in the protein, and M is the measured count for the amino acid in the protein. If M>Caa, a probability of 0 is returned. If a sequence of multiple amino acid count measurements is made, the probabilities may be multiplied to determine the probability of the complete set of N measurements given a candidate protein, as expressed by:

Pr(outcome set|protein)=Pr(measurement outcome for amino acid 1|protein)*Pr(measurement outcome for amino acid 2|protein)* . . . Pr(measurement outcome for amino acid N|protein).

The probability of a particular candidate protein being the correct identification for the protein being measured can be expressed as $$\frac{Pr(\text{outcome set} \mid \text{candidate protein})}{\sum_{i=1}^{P} Pr(\text{outcome set} \mid protein_i)}$$

where $\sum_{i=1}^{P} Pr(\text{outcome set}|protein_i)$ is the sum of the probabilities of the outcome set for each possible protein in the protein sequence database consisting of P proteins.

Detections from Order Measurements of Amino Acids

In some embodiments, an order of selectively-modified amino acids in a protein may be measured. For example, a protein with sequence TINYPRTEIN may generate a measurement outcome ININ if amino acids I and N are modified and measured. Similarly, the same protein may generate a measurement outcome INN, or IIN, in cases where a subset of amino acid modifications and/or measurements is not successful. The probability Pr(measurement outcome|protein) can be expressed as Pr(aa_counts protein)*NUMORDER. The Pr(aa_counts protein)=$\Pi_{i=1}^{i=L}(R_{aai})^{Mi}*(1-R_{aai})^{Caai-Mi}$ where $R_{aai}$ is the reaction efficiency for amino acid i, $M_i$ is the number of times the amino acid i was measured (e.g., in a measurement outcome of INN, N was measured 2 times), $C_{aai}$ is the number of times amino acid i occurs in the sequence of the candidate protein, and amino acids 1 to L are all unique amino acids measured in the protein (e.g., I and N, for measurement outcome ININ). If the number of counts measured for any particular amino acid is greater than the number of times that amino acid occurs in the protein candidate sequence, then the probability Pr(aa_counts protein) is set to zero. NUMORDER is the number of ways a particular outcome can be generated from the protein sequence. For example, the measurement outcome of IN can be generated from the protein TINYPRTEIN in the following ways:
{T<u>IN</u>YPRTEIN, TINYPRTE<u>IN</u>, TINYPRTE<u>IN</u>}, so NUMORDER is 3 for this particular outcome and protein sequence. Note that NUMORDER has a value of zero in cases where it is not possible to generate a particular outcome from a protein (for example, the measurement outcome of INNI cannot be generated from the protein TINYPRTEIN). The probability of a particular candidate protein being the correct identification for the protein being measured can be expressed as $$\frac{Pr(\text{measurement outcome} \mid \text{candidate protein})}{\sum_{i=1}^{P} Pr(\text{measurement outcome} \mid \text{protein}_i)}$$

where $\sum_{i=1}^{P} Pr(\text{measurement outcome}|\text{protein}_i)$ is the sum of the probabilities of the measurement outcome for each possible protein in the protein sequence database consisting of P proteins. In cases where $\sum_{i=1}^{P} Pr(\text{measurement outcome}|\text{protein}_i)$ is equal to zero, the probability of the candidate protein is set to zero.

Figure 22:
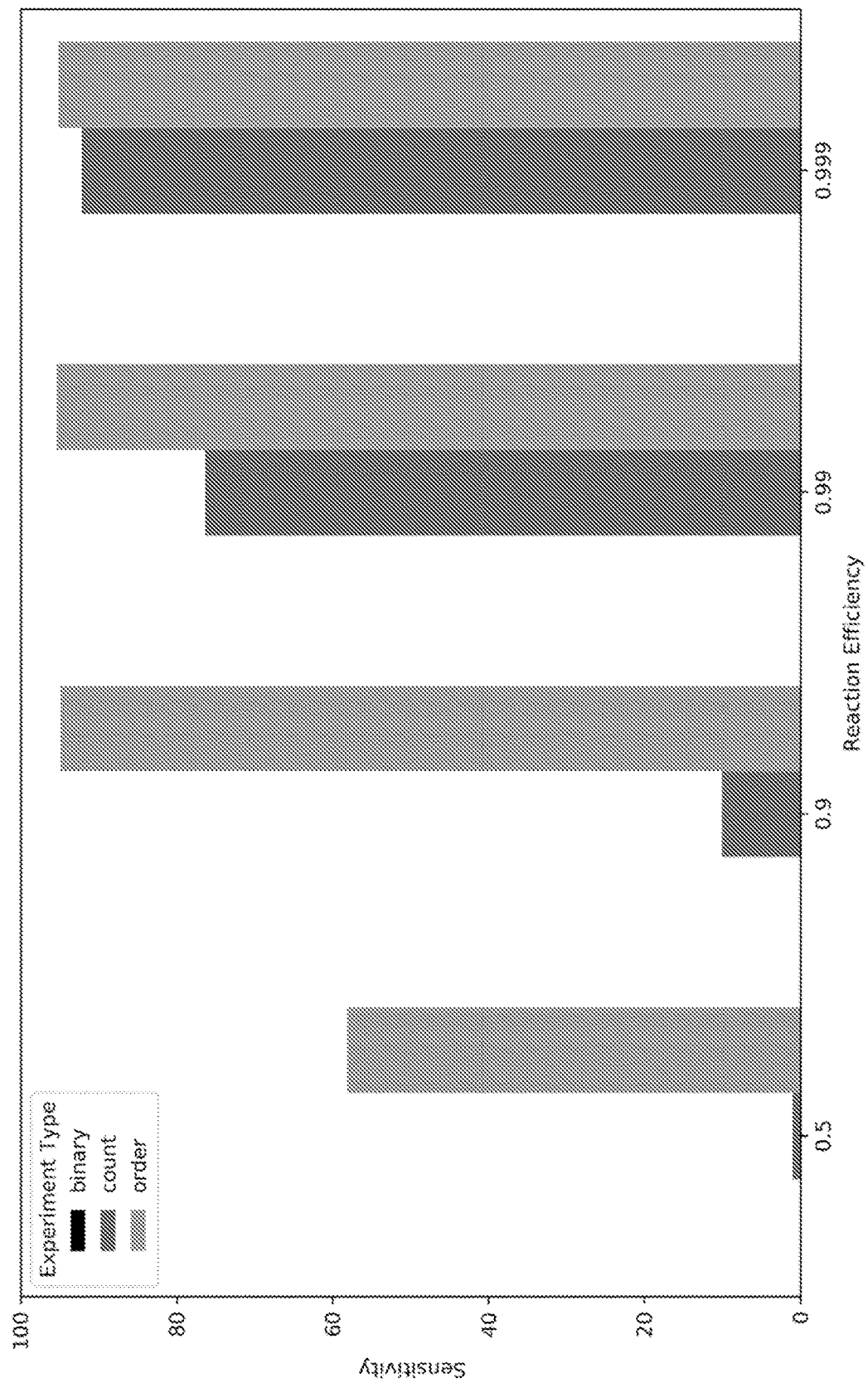
FIG. 22 illustrates the performance of protein identification using a collection of reagents for selective modification and detection of 4 amino acids (K, D, C, and W), in accordance with some embodiments.

The performance of protein identification using a collection of reagents for selective modification and detection of amino acids K, D, C, and W is illustrated in FIG. 22 and Table 14. The reactions are performed with varying efficiency, as indicated on the x-axis. The detection modality (either "binary," "count," or "order," indicating detection of presence or absence of amino acids, counts of amino acids, or order of amino acids, respectively) is indicated by the shade of each bar. The height of each bar indicates the percent of proteins in the sample identified with a false discovery rate below 1%. The sample measured was a human protein sample containing 1,000 proteins. The results indicate that a substantial number of proteins can be identified using measurements of order of amino acids with a reaction efficiency of 0.9 or higher. If measurements of counts of amino acids are used, a substantial number of proteins can be identified with a reaction efficiency of 0.99 or higher. In none of the tested scenarios was measurement of presence or absence of amino acids sufficient to generate protein detections.

TABLE 14

Protein Identification Performance using Selective Modification and Detection of 4 Amino Acids (K, D, C, and W)

| Experiment Name | Experiment Type | Sensitivity | Reaction Efficiency |
|---|---|---|---|
| KDWC Binary 0.5 | binary | 0 | 0.5 |
| KDWC Count 0.5 | count | 1 | 0.5 |
| KDWC Order 0.5 | order | 58.1 | 0.5 |
| KDWC Binary 0.9 | binary | 0 | 0.9 |
| KDWC Count 0.9 | count | 10.1 | 0.9 |
| KDWC Order 0.9 | order | 94.9 | 0.9 |
| KDWC Binary 0.99 | binary | 0 | 0.99 |
| KDWC Count 0.99 | count | 76.4 | 0.99 |
| KDWC Order 0.99 | order | 95.4 | 0.99 |
| KDWC Binary 0.999 | binary | 0 | 0.999 |
| KDWC Count 0.999 | count | 92.2 | 0.999 |

TABLE 14-continued

Protein Identification Performance using Selective Modification and Detection of 4 Amino Acids (K, D, C, and W)

| Experiment Name | Experiment Type | Sensitivity | Reaction Efficiency |
|---|---|---|---|
| KDWC Order 0.999 | order | 95.2 | 0.999 |

Figure 23:
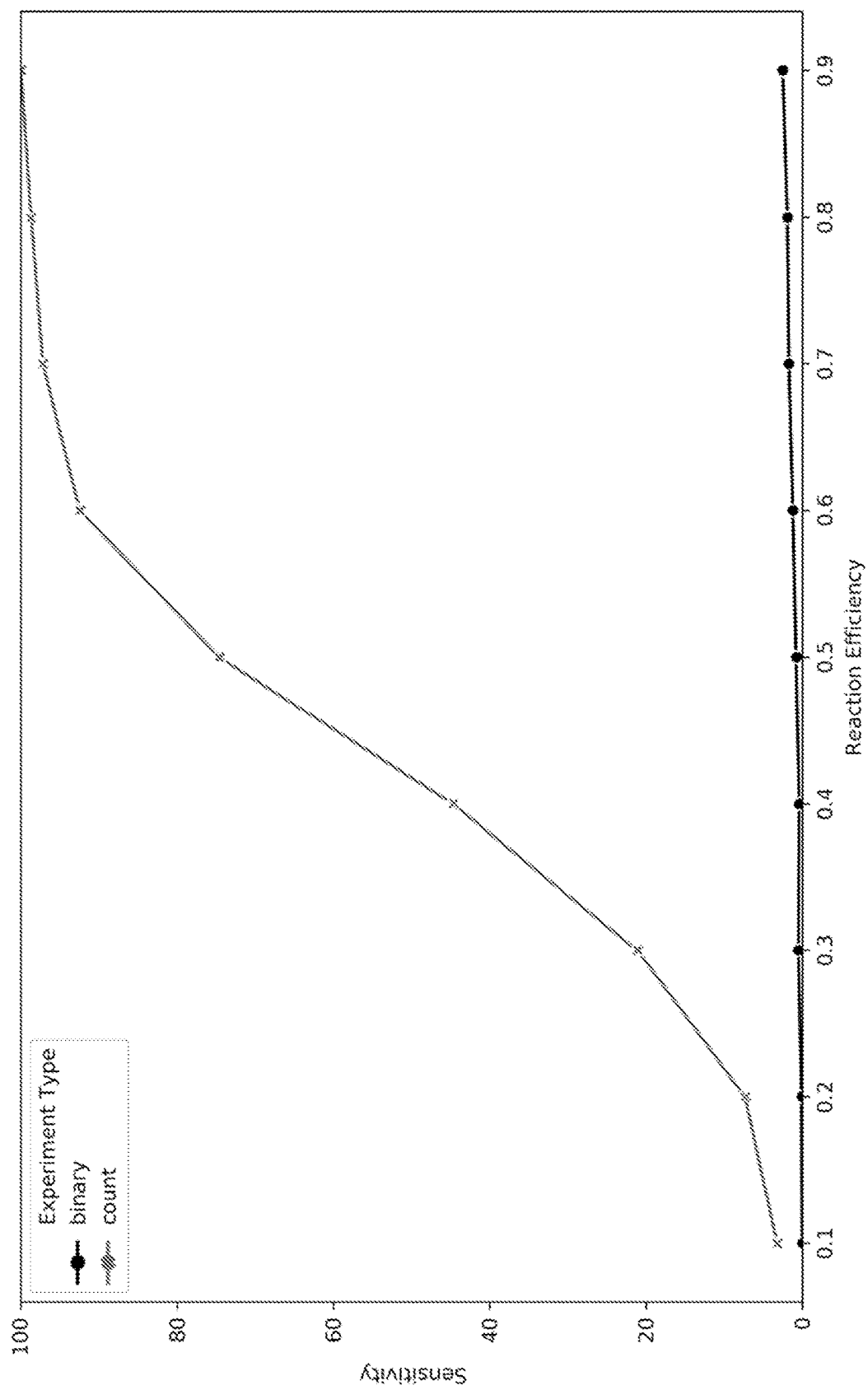
FIG. 23 illustrates the performance of protein identification using a collection of reagents for selective modification and detection of 20 amino acids (R, H, K, D, E, S, T, N, Q, C, G, P, A, V, I, L, M, F, Y, and W), in accordance with some embodiments.

As shown in FIG. 23, the collection of reagents for selective modification and detection of amino acids was expanded to include the 20 amino acids R, H, K, D, E, S, T, N, Q, C, G, P, A, V, I, L, M, F, Y, and W. The detection modality is indicated by the line shade, and the reaction efficiency is indicated on the x-axis. The y-axis indicates the percent of proteins identified with a false discovery rate below 1% in the sample.

The results shown in FIG. 23 and Table 15 indicate that such a collection of reagents is very effective at protein identification if reaction efficiency is greater than about 0.6 and measurements of counts of amino acids are used. However, only a small percentage of proteins is ever identified if measurements of presence or absence of amino acids are used instead of measurements of counts of amino acids.

TABLE 15

Protein Identification Performance using Selective Modification and Detection of 20 Amino Acids (R, H, K, D, E, S, T, N, Q, C, G, P, A, V, I, L, M, F, Y, and W)

| Experiment Name | Experiment Type | Sensitivity | Reaction Efficiency |
|---|---|---|---|
| All Res Binary 0.1 | binary | 0 | 0.1 |
| All Res Count 0.1 | count | 3.2 | 0.1 |
| All Res Binary 0.2 | binary | 0.1 | 0.2 |
| All Res Count 0.2 | count | 7.3 | 0.2 |
| All Res Binary 0.3 | binary | 0.5 | 0.3 |
| All Res Count 0.3 | count | 21.1 | 0.3 |
| All Res Binary 0.4 | binary | 0.4 | 0.4 |
| All Res Count 0.4 | count | 44.7 | 0.4 |
| All Res Binary 0.5 | binary | 0.8 | 0.5 |
| All Res Count 0.5 | count | 74.6 | 0.5 |
| All Res Binary 0.6 | binary | 1.2 | 0.6 |
| All Res Count 0.6 | count | 92.4 | 0.6 |
| All Res Binary 0.7 | binary | 1.7 | 0.7 |
| All Res Count 0.7 | count | 97.1 | 0.7 |
| All Res Binary 0.8 | binary | 1.9 | 0.8 |
| All Res Count 0.8 | count | 98.6 | 0.8 |
| All Res Binary 0.9 | binary | 2.5 | 0.9 |
| All Res Count 0.9 | count | 99.9 | 0.9 |

Figure 24:
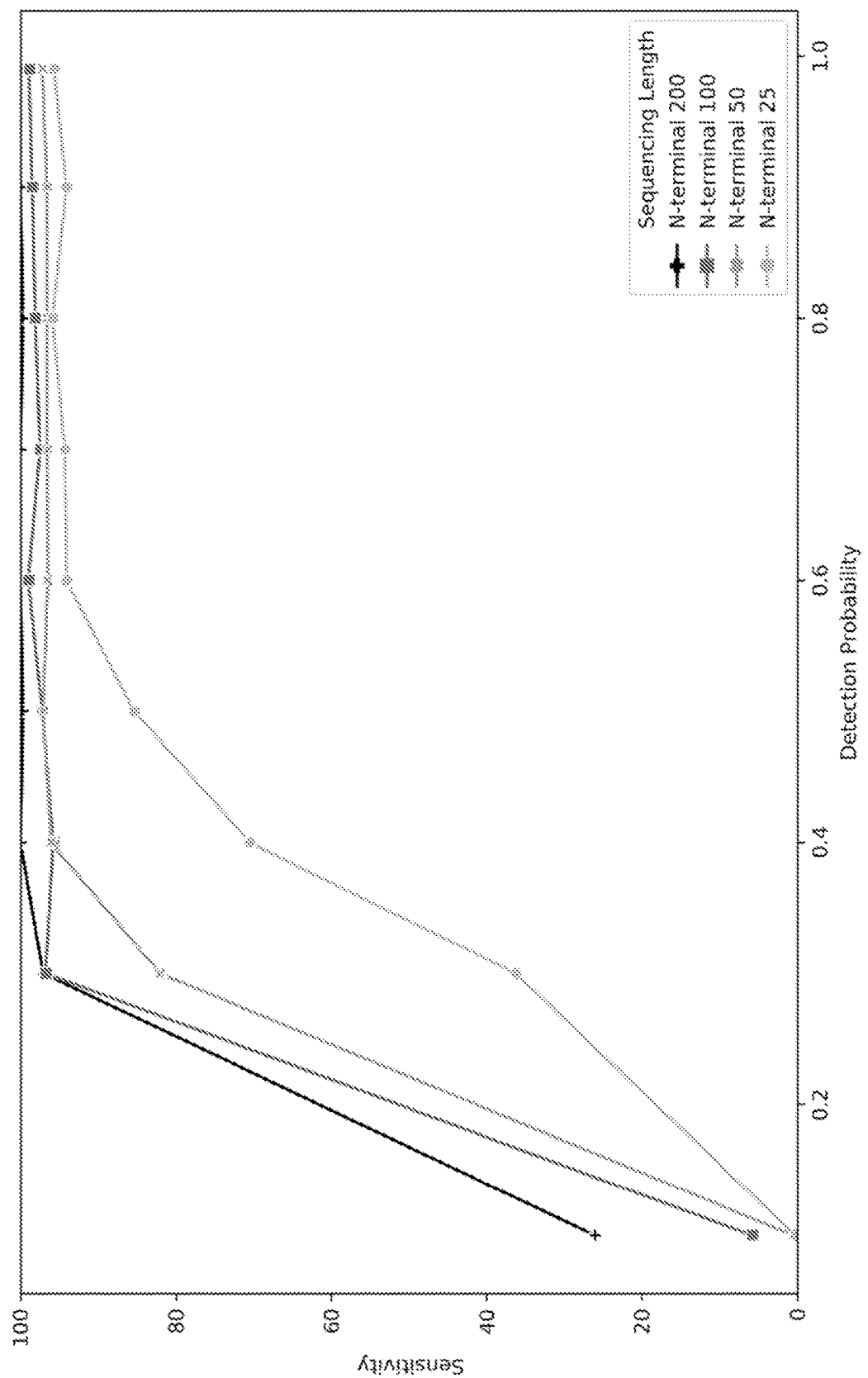
FIG. 24 illustrates the performance of protein identification using measurements of order of amino acids, where all amino acids are measured with a detection probability (equal to reaction efficiency) indicated on the x-axis, and the y-axis indicates the percent of proteins in the sample identified with a false discovery rate below 1%, in accordance with some embodiments.

FIG. 24 illustrates the performance of protein identification using measurements of order of amino acids, where amino acids are measured with a detection probability (equal to reaction efficiency) indicated on the x-axis. The y-axis indicates the percent of proteins in the sample identified with a false discovery rate below 1%. The experiment was performed with measurements of order of amino acids measured at the N-terminal 25, 50, 100, or 200 amino acids of each protein, and the candidate protein sequence database consisted of the first 25, 50, 100, or 200 amino acids, respectively, of each canonical protein sequence in the Uniprot reference human protein database.

The performance illustrated in FIG. 24 and Table 16 indicates that, with detection probability of about 0.3, it is optimal to sequence at least the first 100 amino acids of each protein. Above a detection probability of about 0.6, sequencing the first 25 amino acids or more appears to be sufficient.

TABLE 16

Protein Identification Performance using Measurements of Order of Amino Acids

| Experiment Name | Experiment Type | Sensitivity | Detection Probability | Sequencing Length |
|---|---|---|---|---|
| Sample Order N term 25 (Prob 0.1) | order | 0.2 | 0.1 | N-terminal 25 |
| Sample Order N term 50 (Prob 0.1) | order | 0.5 | 0.1 | N-terminal 50 |
| Sample Order N term 100 (Prob 0.1) | order | 5.8 | 0.1 | N-terminal 100 |
| Sample Order N term 200 (Prob 0.1) | order | 26 | 0.1 | N-terminal 200 |
| Sample Order N term 25 (Prob 0.3) | order | 36.2 | 0.3 | N-terminal 25 |
| Sample Order N term 50 (Prob 0.3) | order | 82.1 | 0.3 | N-terminal 50 |
| Sample Order N term 100 (Prob 0.3) | order | 96.8 | 0.3 | N-terminal 100 |
| Sample Order N term 200 (Prob 0.3) | order | 97.1 | 0.3 | N-terminal 200 |
| Sample Order N term 25 (Prob 0.4) | order | 70.5 | 0.4 | N-terminal 25 |
| Sample Order N term 50 (Prob 0.4) | order | 96.1 | 0.4 | N-terminal 50 |
| Sample Order N term 100 (Prob 0.4) | order | 95.8 | 0.4 | N-terminal 100 |
| Sample Order N term 200 (Prob 0.4) | order | 100 | 0.4 | N-terminal 200 |
| Sample Order N term 25 (Prob 0.5) | order | 85.4 | 0.5 | N-terminal 25 |
| Sample Order N term 50 (Prob 0.5) | order | 97.1 | 0.5 | N-terminal 50 |
| Sample Order N term 100 (Prob 0.5) | order | 97.2 | 0.5 | N-terminal 100 |
| Sample Order N term 200 (Prob 0.5) | order | 99.7 | 0.5 | N-terminal 200 |
| Sample Order N term 25 (Prob 0.6) | order | 94.1 | 0.6 | N-terminal 25 |
| Sample Order N term 50 (Prob 0.6) | order | 96.5 | 0.6 | N-terminal 50 |
| Sample Order N term 100 (Prob 0.6) | order | 99 | 0.6 | N-terminal 100 |
| Sample Order N term 200 (Prob 0.6) | order | 100 | 0.6 | N-terminal 200 |
| Sample Order N term 25 (Prob 0.7) | order | 94.3 | 0.7 | N-terminal 25 |
| Sample Order N term 50 (Prob 0.7) | order | 96.6 | 0.7 | N-terminal 50 |
| Sample Order N term 100 (Prob 0.7) | order | 97.5 | 0.7 | N-terminal 100 |
| Sample Order N term 200 (Prob 0.7) | order | 100 | 0.7 | N-terminal 200 |

FIG. 25 illustrates the performance of various approaches on a tryptic digest of a sample consisting of 1,000 unique human proteins. The sample contains all fully tryptic peptides of length greater than 12 with no missed cleavages arising from these proteins. The dark lines indicate performance when protein identification is performed using measurements of the order of all amino acids, which are measured at varying detection probability (equivalent to reaction efficiency). The light lines indicate performance when only the order of amino acids K, D, W, and C are measured at varying detection probability (equivalent to reaction efficiency). The sequence database used for inference contains the sequences of every fully tryptic peptide with length greater than 12 with no missed cleavages arising from these proteins, derived from every canonical protein sequence in the human reference proteome database downloaded from Uniprot. The solid lines indicate the percentage of peptides in the sample identified at a false discovery rate below 1%. The dashed lines indicate the percentage of proteins in the sample identified at a false discovery rate below 1%. A protein is identified if a peptide with sequence unique to that protein is identified at a false discovery rate below 1%. These results indicate that measuring the order of just amino acids K, D, W, and C may not be sufficient for protein detection from a tryptic digest sample. Further, measuring the order of all amino acids with a detection probability (equivalent to reaction efficiency) at or above about 0.5 is sufficient to identify the majority of proteins in a tryptic digest.

Computer Control Systems

The present disclosure provides computer control systems that are programmed to implement methods of the disclosure. FIG. 10 shows a computer system 1001 that is programmed or otherwise configured to: receive information of empirical measurements of unknown proteins in a sample, compare information of empirical measurements against a database comprising a plurality of protein sequences corresponding to candidate proteins, generate probabilities of a candidate protein generating the observed measurement outcome set, and/or generate probabilities that candidate proteins are correctly identified in the sample.

The computer system 1001 can regulate various aspects of methods and systems of the present disclosure, such as, for example, receiving information of empirical measurements of unknown proteins in a sample, comparing information of empirical measurements against a database comprising a plurality of protein sequences corresponding to candidate proteins, generating probabilities of a candidate protein generating the observed measurement outcome set, and/or generating probabilities that candidate proteins are correctly identified in the sample.

The computer system 1001 can be an electronic device of a user or a computer system that is remotely located with respect to the electronic device. The electronic device can be a mobile electronic device. The computer system 1001 includes a central processing unit (CPU, also "processor" and "computer processor" herein) 1005, which can be a single core or multi core processor, or a plurality of processors for parallel processing. The computer system 1001 also includes memory or memory location 1010 (e.g., random-access memory, read-only memory, flash memory), electronic storage unit 1015 (e.g., hard disk), communication interface 1020 (e.g., network adapter) for communicating with one or more other systems, and peripheral devices 1025, such as cache, other memory, data storage and/or electronic display adapters. The memory 1010, storage unit 1015, interface 1020 and peripheral devices 1025 are in communication with the CPU 1005 through a communication bus (solid lines), such as a motherboard. The storage unit 1015 can be a data storage unit (or data repository) for storing data. The computer system 1001 can be operatively coupled to a computer network ("network") 1030 with the aid of the communication interface 1020. The network 1030 can be the Internet, an internet and/or extranet, or an intranet and/or extranet that is in communication with the Internet. The network 1030 in some cases is a telecommunication and/or data network. The network 1030 can include one or more computer servers, which can enable distributed computing, such as cloud computing. For example, one or more computer servers may enable cloud computing over the network 1030 ("the cloud") to perform various aspects of analysis, calculation, and generation of the present disclosure, such as, for example, receiving information of empirical measurements of unknown proteins in a sample, comparing information of empirical measurements against a database comprising a plurality of protein sequences corresponding to candidate proteins, generating probabilities of a candidate protein generating the observed measurement outcome set, and/or generating probabilities that candidate proteins are correctly identified in the sample. Such cloud computing may be provided by cloud computing platforms such as, for example, Amazon Web Services (AWS), Microsoft Azure, Google Cloud Platform, and IBM cloud. The network 1030, in some cases with the aid of the computer system 1001, can implement a peer-to-peer network, which may enable devices coupled to the computer system 1001 to behave as a client or a server.

The CPU 1005 can execute a sequence of machine-readable instructions, which can be embodied in a program or software. The instructions may be stored in a memory location, such as the memory 1010. The instructions can be directed to the CPU 1005, which can subsequently program or otherwise configure the CPU 1005 to implement methods of the present disclosure. Examples of operations performed by the CPU 1005 can include fetch, decode, execute, and writeback.

The CPU 1005 can be part of a circuit, such as an integrated circuit. One or more other components of the system 1001 can be included in the circuit. In some cases, the circuit is an application specific integrated circuit (ASIC).

The storage unit 1015 can store files, such as drivers, libraries and saved programs. The storage unit 1015 can store user data, e.g., user preferences and user programs. The computer system 1001 in some cases can include one or more additional data storage units that are external to the computer system 1001, such as located on a remote server that is in communication with the computer system 1001 through an intranet or the Internet.

The computer system 1001 can communicate with one or more remote computer systems through the network 1030. For instance, the computer system 1001 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1001 via the network 1030.

Methods as described herein can be implemented by way of machine (e.g., computer processor) executable code stored on an electronic storage location of the computer system 1001, such as, for example, on the memory 1010 or electronic storage unit 1015. The machine executable or machine readable code can be provided in the form of software. During use, the code can be executed by the processor 1005. In some cases, the code can be retrieved from the storage unit 1015 and stored on the memory 1010 for ready access by the processor 1005. In some situations, the electronic storage unit 1015 can be precluded, and machine-executable instructions are stored on memory 1010.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 1001, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (TR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1001 can include or be in communication with an electronic display 1035 that comprises a user interface (UI) 1040 for providing, for example, user selection of algorithms, binding measurement data, candidate proteins, and databases. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 1005. The algorithm can, for example, receive information of empirical measurements of unknown proteins in a sample, compare information of empirical measurements against a database comprising a plurality of protein sequences corresponding to candidate proteins, generate probabilities of a candidate protein generating the observed measurement outcome set, and/or generate probabilities that candidate proteins are correctly identified in the sample.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for identifying at least one candidate protein of a sample, the method comprising:
   (a) obtaining a series of empirical measurements from a series of covalent amino acid modification reactions performed serially on each protein of a plurality of proteins from the sample, the series of empirical measurements performed while the plurality of proteins of the sample is attached to a substrate, the series of empirical measurements indicating an order of covalently modified amino acids in individual proteins from the plurality of proteins from the sample, wherein the obtaining of the series of empirical measurements comprises:
       (i) for each protein of the plurality of proteins, performing a covalent amino acid modification in the series of covalent amino acid modification reactions on the protein, wherein the covalent amino acid modification selectively modifies a particular amino acid of the protein,
       (ii) detecting the presence or absence of the selectively modified amino acid of the protein, and
       (iii) repeating (i) and (ii) to perform at least one additional covalent amino acid modification in the series of covalent amino acid modification reactions on the protein and to detect the presence or absence of another selectively modified amino acid of the protein, wherein the at least one additional covalent amino acid modification reaction selectively modifies the particular amino acid of the protein;
   (b) comparing, by a computer, the series of empirical measurements to measurement outcomes for a plurality of candidate proteins; and
   (c) based at least in part on the comparing in (b), identifying, by the computer, the at least one candidate protein in the sample, at least in part by applying a trained algorithm to the series of empirical measurements to determine a probability that the at least one candidate protein of the sample generates the series of empirical measurements.

2. The method of claim 1, wherein the detecting comprises detecting fluorescence produced by the covalent amino acid modification reactions.

3. The method of claim 1, wherein (c) comprises identifying, by the computer, the at least one candidate protein in the sample based at least in part on:
   (i) the probability that the at least one candidate protein of the sample generates the series of empirical measurements, and
   (ii) a probability that the series of empirical measurements is not observed given that the at least one candidate protein of the sample is present in the sample.

4. The method of claim 1, wherein the measurement outcomes are derived from a database of previous measurements of the plurality of candidate proteins.

5. The method of claim 1, wherein the measurement outcomes are calculated completely in silico.

6. The method of claim 1, wherein the measurement outcomes are derived from features of an amino acid sequence of the at least one candidate protein of the sample.

7. The method of claim 1, wherein the series of empirical measurements comprise binding measurements of affinity reagent probes configured to bind the at least one candidate protein of the sample.

8. The method of claim 1, further comprising generating, for the at least one candidate protein of the sample, a confidence level that the at least one candidate protein of the sample matches a protein from the plurality of proteins from the sample.

9. The method of claim 1, wherein (c) further comprises determining the probability that the at least one candidate protein of the sample generates the series of empirical measurements at least in part according to:

$$Pr(\text{measurement outcome} \mid \text{protein}) =$$
$$Pr(\text{aa\_counts} \mid \text{protein}) * NUMORDER$$

wherein NUMORDER is a number of ways the measurement outcomes can be generated, wherein $$Pr(\text{aa\_counts} \mid \text{protein}) = \prod_{i=1}^{i=1} (R_{eai})^{Mi} * (1 - R_{asi})^{Caai-Mi}$$

wherein Raai is an efficiency for a selective amino acid modification reaction that selectively modifies an amino acid i, wherein Mi is a number of times the amino acid i is measured in the protein, and wherein Caai is a number of times the amino acid i occurs in a candidate protein.

10. The method of claim 9, wherein (c) further comprises determining the probability that the at least one candidate protein of the sample generates the series of empirical measurements at least in part according to:

$$\frac{Pr(\text{measurement outcome} \mid \text{candidate protein})}{\sum_{i=1}^{P} Pr(\text{measurement outcome} \mid protein_i)}$$

wherein $\Sigma_{i=1}^{P}$ Pr(measurement outcome|$protein_i$) is a sum of probabilities of the measurement outcomes for a set of P proteins.

11. The method of claim 1, wherein each protein of the plurality of proteins from the sample is associated with a unique spatial address.

12. The method of claim 11, wherein each protein from the plurality of proteins from the sample is optically resolvable from each other protein from the plurality of proteins from the sample.

13. The method of claim 12, wherein the plurality of proteins from the sample is conjugated to the substrate at a plurality of spatially separate locations.

14. The method of claim 1, wherein the series of empirical measurements is obtained using an optical detector.

15. The method of claim 1, wherein the series of empirical measurements is obtained using a magnetic detector.

16. The method of claim 1, wherein the series of empirical measurements is obtained using an electrostatic detector or an electrochemical detector.

17. The method of claim 1, wherein the probability that at least one candidate protein of the sample generates the series of empirical measurements is determined using a plurality of measurement outcomes.

18. The method of claim 1, wherein the probability that at least one candidate protein of the sample generates the series of empirical measurements is determined using a product of probabilities for the measurement outcomes of the at least one candidate protein of the sample.

19. The method of claim 1, wherein the at least one candidate protein of the sample comprises at least 10 different candidate proteins.

20. The method of claim 1, wherein the trained algorithm comprises a probabilistic model that is iteratively improved by performing an expectation maximization algorithm on the series of empirical measurements.

21. The method of claim 1, wherein the series of empirical measurements from the series of covalent amino acid modification reactions comprise selective modification and detection of lysine amino acids.

22. The method of claim 1, wherein the series of empirical measurements from the series of covalent amino acid modification reactions comprise selective modification and detection of cysteine amino acids.

23. The method of claim 1, wherein the plurality of proteins comprises at least 1,000 proteins from a human protein sample.

24. The method of claim 1, wherein the series of covalent amino acid modification reactions comprise modification reactions performed on 25 N-terminal amino acids of each protein of the plurality of proteins from the sample.

25. The method of claim 1, wherein performing the series of covalent amino acid modification reactions on the protein of the plurality of proteins from the sample is by way of direct functionalization of amino acids, wherein each of the series of covalent amino acid modification reactions selectively and covalently modifies a particular amino acid in the protein of the plurality of proteins from the sample.

26. The method of claim 1, further comprising, prior to (ii), attaching the plurality of proteins to the substrate.

* * * * *